US012788821B2

(12) United States Patent
Zhou et al.

(10) Patent No.: US 12,788,821 B2
(45) Date of Patent: Nov. 10, 2026

(54) MODIFIED BINDING POLYPEPTIDES FOR OPTIMIZED DRUG CONJUGATION

(71) Applicant: GENZYME CORPORATION, Cambridge, MA (US)

(72) Inventors: Qun Zhou, Cambridge, MA (US); Sunghae Park, Cambridge, MA (US); Huawei Qiu, Cambridge, MA (US); Marie-Priscille Brun, Paris (FR); Francis Duffieux, Paris (FR)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 18/534,085

(22) Filed: Dec. 8, 2023

(65) Prior Publication Data

US 2024/0218051 A1 Jul. 4, 2024

Related U.S. Application Data

(62) Division of application No. 17/187,039, filed on Feb. 26, 2021, now Pat. No. 11,879,004.

(60) Provisional application No. 62/982,943, filed on Feb. 28, 2020.

(51) Int. Cl.

| | |
|---|---|
| ***A61K 47/60*** | (2017.01) |
| ***A61K 47/68*** | (2017.01) |
| ***C07K 16/00*** | (2006.01) |

(52) U.S. Cl.

CPC .......... *A61K 47/60* (2017.08); *A61K 47/6803* (2017.08); *C07K 16/00* (2013.01); *C07K 2317/14* (2013.01); *C07K 2317/52* (2013.01); *C07K 2317/56* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 4,975,278 A | 12/1990 | Senter et al. | |
| 5,202,238 A | 4/1993 | Fell, Jr. et al. | |
| 5,204,244 A | 4/1993 | Fell, Jr. et al. | |
| 5,208,020 A | 5/1993 | Chari et al. | |
| 5,225,539 A | 7/1993 | Winter | |
| 5,530,101 A | 6/1996 | Queen et al. | |
| 5,565,332 A | 10/1996 | Hoogenboom et al. | |
| 5,585,089 A | 12/1996 | Queen et al. | |
| 5,648,260 A | 7/1997 | Winter et al. | |
| 5,739,277 A | 4/1998 | Presta et al. | |
| 5,834,250 A | 11/1998 | Wells et al. | |
| 5,837,821 A | 11/1998 | Wu | |
| 5,869,046 A | 2/1999 | Presta et al. | |
| 5,989,830 A | 11/1999 | Davis et al. | |
| 6,096,871 A | 8/2000 | Presta et al. | |
| 6,121,022 A | 9/2000 | Presta et al. | |
| 6,193,980 B1 | 2/2001 | Efstathiou et al. | |
| 6,194,551 B1 | 2/2001 | Idusogie et al. | |
| 6,242,195 B1 | 6/2001 | Idusogie et al. | |
| 6,277,375 B1 | 8/2001 | Ward | |
| 6,528,624 B1 | 3/2003 | Idusogie et al. | |
| 6,538,124 B1 | 3/2003 | Idusogie et al. | |
| 6,737,056 B1 | 5/2004 | Presta | |
| 6,821,505 B2 | 11/2004 | Ward | |
| 6,998,253 B1 | 2/2006 | Presta et al. | |
| 7,083,784 B2 | 8/2006 | Dall'Acqua et al. | |
| 7,521,541 B2 | 4/2009 | Eigenbrot et al. | |
| 7,612,181 B2 | 11/2009 | Wu et al. | |
| 8,163,881 B2 | 4/2012 | Ober | |
| 8,524,865 B2 * | 9/2013 | Ebens, Jr. | C07K 16/3061 530/387.3 |
| 10,160,812 B2 | 12/2018 | Li et al. | |
| 10,744,204 B2 | 8/2020 | Gao et al. | |
| 11,879,004 B2 | 1/2024 | Zhou et al. | |
| 2002/0102208 A1 | 8/2002 | Chinn et al. | |
| 2004/0110226 A1 | 6/2004 | Lazar et al. | |
| 2007/0092940 A1 * | 4/2007 | Eigenbrot | A61P 35/00 435/456 |
| 2008/0050310 A1 | 2/2008 | Ebens, Jr. et al. | |
| 2009/0258420 A1 | 10/2009 | Van Vlijmen et al. | |
| 2010/0226923 A1 | 9/2010 | Rao et al. | |
| 2012/0213705 A1 | 8/2012 | Dimasi et al. | |
| 2012/0251541 A1 | 10/2012 | Baurin et al. | |
| 2013/0295097 A1 | 11/2013 | Orengo et al. | |
| 2016/0008485 A1 * | 1/2016 | Marquette | C07K 16/30 424/1.49 |

(Continued)

FOREIGN PATENT DOCUMENTS

| | | |
|---|---|---|
| CN | 106459205 A | 2/2017 |
| EP | 0239400 A2 | 9/1987 |
| EP | 0592106 A1 | 4/1994 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Poosarla et al., Biotechn. Bioeng., 114(6): 1331-1342 (Year: 2017).*
Piche-Nicholas et al., MABS 10(1): 81-94 (Year: 2018).*
Zhou et al., Pharamceuticals 14 (672): 1-17 (Year: 2021).*
Almagro, et al., "Humanization of Antibodies", Frontiers in Bioscience, 2008, vol. 13, pp. 1619-1633.

(Continued)

*Primary Examiner* — Phuong Huynh

(74) *Attorney, Agent, or Firm* — LATHROP GPM LLP; James H. Velema, Esq.

(57) ABSTRACT

Engineered antibodies that are stable and can be conjugated to a ligand or drug at a ligand/drug to antibody ratio of above 3, making these conjugates suitable for treatment of a variety of indications, are provided. Methods of producing these engineered antibodies are also provided.

34 Claims, 26 Drawing Sheets

(56) References Cited

U.S. PATENT DOCUMENTS

| | | | | |
|---|---|---|---|---|
| 2016/0067351 | A1* | 3/2016 | Geierstanger | A61K 47/68031 435/69.6 |
| 2017/0021033 | A1* | 1/2017 | Geierstanger | A61K 47/68031 |
| 2017/0291955 | A1* | 10/2017 | Li | C07K 16/30 |
| 2018/0169255 | A1* | 6/2018 | Gao | A61K 47/6817 |
| 2019/0099499 | A1 | 4/2019 | Katragadda et al. | |
| 2021/0292391 | A1 | 9/2021 | Zhou et al. | |
| 2022/0249679 | A1* | 8/2022 | Coronella | A61K 47/6849 |
| 2023/0391849 | A1 | 12/2023 | Zhou et al. | |
| 2024/0218051 | A1 | 7/2024 | Zhou | |

FOREIGN PATENT DOCUMENTS

| | | | |
|---|---|---|---|
| EP | 0125023 | B2 | 3/2002 |
| EP | 0519596 | B1 | 2/2005 |
| RU | 2658491 | C2 | 6/2018 |
| WO | WO 1981/001145 | A1 | 4/1981 |
| WO | WO 1988/007089 | A1 | 9/1988 |
| WO | WO 1988/007378 | A1 | 10/1988 |
| WO | WO 1991/009967 | A1 | 7/1991 |
| WO | WO 1994/009817 | A1 | 5/1994 |
| WO | WO 1994/011026 | A2 | 5/1994 |
| WO | WO 1996/002576 | A1 | 2/1996 |
| WO | WO 1996/014339 | A1 | 5/1996 |
| WO | WO 1998/005787 | A1 | 2/1998 |
| WO | WO 1998/023289 | A1 | 6/1998 |
| WO | WO 1999/051642 | A1 | 10/1999 |
| WO | WO 1999/058572 | A1 | 11/1999 |
| WO | WO 2000/009560 | A2 | 2/2000 |
| WO | WO 2000/032767 | A1 | 6/2000 |
| WO | WO 2000/042072 | A2 | 7/2000 |
| WO | WO 2002/002781 | A1 | 1/2002 |
| WO | WO 2002/044215 | A2 | 6/2002 |
| WO | WO 2002/060919 | A2 | 8/2002 |
| WO | WO 2003/074569 | A2 | 9/2003 |
| WO | WO 2004/016750 | A2 | 2/2004 |
| WO | WO 2004/029207 | A2 | 4/2004 |
| WO | WO 2004/035752 | A2 | 4/2004 |
| WO | WO 2004/063351 | A2 | 7/2004 |
| WO | WO 2004/074455 | A2 | 9/2004 |
| WO | WO 2004/099249 | A2 | 11/2004 |
| WO | WO 2005/040217 | A2 | 5/2005 |
| WO | WO 2005/047327 | A2 | 5/2005 |
| WO | WO 2005/070963 | A1 | 8/2005 |
| WO | WO 2005/077981 | A2 | 8/2005 |
| WO | WO 2005/092925 | A2 | 10/2005 |
| WO | WO 2005/123780 | A2 | 12/2005 |
| WO | WO 2006/019447 | A1 | 2/2006 |
| WO | WO 2006/034488 | A2 | 3/2006 |
| WO | WO 2006/047350 | A2 | 5/2006 |
| WO | WO 2006/085967 | A2 | 8/2006 |
| WO | WO 2009/012268 | A1 | 1/2009 |
| WO | WO 2009/032661 | A1 | 3/2009 |
| WO | WO 2009/080253 | A1 | 7/2009 |
| WO | WO 2015/143091 | A1 | 9/2015 |
| WO | WO 2015/157595 | A1 | 10/2015 |
| WO | WO 2017/021033 | A1 | 2/2017 |
| WO | WO 2019/099499 | A1 | 5/2019 |
| WO | WO 2020/132100 | A1 | 6/2020 |

OTHER PUBLICATIONS

Banik, et al., "Lysosome-Targeting Chimaeras for Degradation of Extracellular Proteins", Nature, 2020, vol. 584, No. 7820, pp. 291-297.

Chen, et al., "In Vivo Targeting of B-Cell Lymphoma with Glycan Ligands of CD22", Blood, Jun. 10, 2010, vol. 115, No. 23, pp. 4778-4786.

Chen, et al., "Targeting B Lymphoma with Nanoparticles Bearing Glycan Ligands of CD22", Leukemia & Lymphoma. Feb. 1, 2012, vol. 53, No. 2, pp. 208-210.

Cobos-Correa, et al., "Membrane-Bound FRET Probe Visualizes MMP12 Activity in Pulmonary Inflammation", Nature Chemical Biology, Sep. 1, 2009, vol. 5, No. 9, pp. 628-663.

Dennler et al., "Antibody Conjugates: From Heterogeneous Populations to Defined Reagents", 2015, 4: 197-224.

Dimitrov, Antony S., "Therapeutic Antibodies Methods and Protocols", Springer Science, 2009, vol. 525, 445 Pages.

Ganesan, et al., "Rapid and Efficient Clearance of Blood-borne Virus by Liver Sinusoidal Endothelium", PLoS Pathogens, Sep. 29, 2011, vol. 7, No. 9, e1002281, pp. 1-11.

Gauthier, et al., "Multifunctional Natural Killer Cell Engagers Targeting NKp46 Trigger Protective Tumor Immunity", Cell, Jun. 13, 2019, vol. 177, No. 7, pp. 1701-1713.

Gehrig, et al., "Spatially Resolved Monitoring of Neutrophil Elastase Activity with Ratiometric Fluorescent Reporters", Angewandte Chemie International Edition, May 3, 2012, vol. 51, No. 25, pp. 6258-6261.

Guan, et al., "Homogeneous Immunoconjugates for Boron Neutron-capture Therapy: Design, Synthesis, and Preliminary Characterization", Proceedings of the National Academy of Sciences, Oct. 2, 1998, vol. 95, No. 22, pp. 13206-13210.

Hatakeyama, et al., "Targeted Drug Delivery to Tumor Vasculature by A Carbohydrate Mimetic Peptide", Proceedings of the National Academy of Sciences, Dec. 6, 2011, vol. 108, No. 49, pp. 19587-19592.

Hong, et al., "β-Glucan Functions as an Adjuvant for Monoclonal Antibody Immunotherapy by Recruiting Tumoricidal Granulocytes as Killer Cells", Cancer Research, Dec. 15, 2003, vol. 63, No. 24, pp. 9023-9031.

International Search Report and Written Opinion for PCT International Patent Application No. PCT/US2021/019958, mailed Jun. 11, 2021.

Jespers, et al., "Guiding the Selection of Human Antibodies from Phage Display Repertoires to a Single Epitope of An Antigen", Bio/Technology, 1994, Nature Publishing Company, vol. 12, No. 9, pp. 899-903.

Jones, Elizabeth W., "Proteinase Mutants of *Saccharomyces cerevisiae*", Genetics, 1977, vol. 85, No. 1, pp. 23-33.

Kawasaki, et al., "Targeted Delivery of Lipid Antigen to Macrophages via the CD169/sialoadhesin Endocytic Pathway Induces Robust Invariant Natural Killer T Cell Activation", Proceedings of the National Academy of Sciences, May 7, 2013, vol. 110, No. 19, pp. 7826-7831.

Kingsman, et al., "Replication in *Saccharomyces cerevisiae* of Plasmid pBR313 Carrying DNA From the Yeast trpl Region", Gene, 1979, vol. 7, No. 2, pp. 141-152.

Lin et al., "Redox-based reagents for chemoselective methionine bioconjugation", Science, Feb. 10, 2017, 355(6325): 597-602.

Maneiro, et al., "Antibody-PROTAC Conjugates Enable HER2-Dependent Targeted Protein Degradation of BRD4", ACS Chemical Biology, 2020, vol. 15, No. 6, pp. 1306-1312.

Medina, et al., "N-Acetylgalactosamine-Functionalized Dendrimers as Hepatic Cancer Cell-Targeted Carriers", Biomaterials, Jun. 1, 2011, vol. 32, No. 17, pp. 4118-4129.

Monnier, et al., "Glucosepane: A Poorly Understood Advanced Glycation End Product of Growing Importance for Diabetes and its Complications", Clinical Chemistry and Laboratory Medicine, 2014, vol. 52, No. 1, pp. 21-32.

Pettersson, et al., "PROteolysis TArgeting Chimeras (PROTACs)—Past, present and future", Drug Discovery Today: Technologies, Apr. 2019, vol. 31, pp. 15-27.

Puthenveetil et al., "Multivalent peptidic linker enables identification of preferred sites of conjugation for a potent thialanstatin antibody drug conjugate", PLOS ONE, May 30, 2017, 12(5): e0178452.

Remington, et al., Remington's Pharmaceutical Sciences, 15th Edition, pp. 1035-1038.

Remington, et al., Remington's Pharmaceutical Sciences, 15th Edition, pp. 1570-1580.

Ridgway, Anthony A.G., "Introduction of Vector into Host Cells", Mammalian Expression Vectors, 1988, Chapter 24.2, pp. 470-472.

Roitt et al., "Molecules which Recognize Antigen", Immunology 2nd Ed., Gower Medical Publishing, pp. 5.8-5.9.

Roux, et al., "Comparisons of the Ability of Human IgG3 Hinge Mutants, IgM, IgE, and IgA2, to Form Small Immune Complexes:

(56) References Cited

OTHER PUBLICATIONS

A Role for Flexibility and Geometry", Journal of Immunology, Oct. 15, 1998, vol. 161, No. 8, pp. 4083-4090.
Schaefer, et al., "Immunoglobulin Domain Crossover as a Generic Approach for the Production of Bispecific IgG Antibodies", Proceedings of the National academy of Sciences, Jul. 5, 2011, vol. 108, No. 27, pp. 11187-11192.
Sochaj, et al., "Current methods for the synthesis of homogeneous antibody-drug conjugates", Biotechnology Advances, Nov. 1, 2015, vol. 33, Issue 6, Part 1, pp. 775-784.
Stinchcomb, et al., "Isolation and Characterisation Of a Yeast Chromosomal Replicator", Nature, Nov. 1, 1979, vol. 282, No. 5734, pp. 39-43.
Strop et al., "Location matters: site of conjugation modulates stability and pharmacokinetics of antibody drug conjugates", Chemistry and Biology, Feb. 21, 2013, 20(2): 161-167.
Thompson et al., "Rational design, biophysical and biological characterization of site-specific antibody-tubulysin conjugates with improved stability, efficacy and pharmacokinetics", Journal of Controlled Release, Jun. 18, 2016, 236: 100-116.
Tschumper, et al., "Sequence of A Yeast DNA Fragment Containing a Chromosomal Replicator and The TRP1 Gene", Gene, Jul. 1, 1980, vol. 10, No. 2, pp. 157-166.
Zhang et al., "Dysfunctional Antibodies in the Tumor Microenvironment Associate with Impaired Anticancer Immunity", Clinical Cancer Res., 2015, 21(23): 5380-5390.
U.S. Appl. No. 17/187,039 2021/0292391 U.S. Pat. No. 11,879,004, filed Feb. 26, 2021 Sep. 23, 2021, Jan. 23, 2024, Qun Zhou, Modified Binding Polypeptides For Optimized Drug Conjugation.
U.S. Appl. No. 18/303,353 2023/0391849, filed Apr. 19, 2023 Dec. 7, 2023, Qun Zhou, Modified Binding Polypeptides For Optimized Drug Conjugation.
Edwards et al., The remarkable flexibility of the human antibody repertoire; isolation of over one thousand different antibodies to a single protein, BLyS, J Mol Biol, 2003, 334: 103-118.
Lloyd et al., Modelling the human immune response: performance of a $10^{11}$ human antibody repertoire against a broad panel of therapeutically relevant antigens, Protein Engineering, Design & Selection, 2009, 22: 159-168.
Martin, "Expression of the 17-1A antigen in gastric and gastro-oesophageal junction adenocarcinomas: a potential immunotherapeutic target?", J Clin Pathol., 1999, 52: 701-704.
Piche-Nicholas et al., "Changes in complementarity-determining regions significantly alter IgG binding to the neonatal Fc receptor (FcRn) and pharmacokinetics", MAbs, 2018, 10(1): 81-94.
Poosarla et al., "Computational De Novo Design of Antibodies Binding to a Peptide With High Affinity", Biotech. Bioeng., 2017, 114(6): 1331-1342.

* cited by examiner

Fig. 2

| # | Mutant | $Tm_1$ | $Tm_2$ |
|---|---|---|---|
| ***1*** | ***Y300C*** | ***62.7*** | ***82.6*** |
| 2 | D413C | 69.9 | 83.3 |
| 3 | A339C | 68.0 | 83.1 |
| 4 | Q418C | 70.2 | 83.4 |
| 5 | A118N | 70.4 | 83.3 |
| 6 | A431C | 67.0 | 83.2 |
| 7 | K414C | 71.7 | 84.0 |
| 8 | Q386C | 70.9 | 83.3 |
| 9 | K274C | 71.9 | 83.7 |
| 10 | G385C | 69.7 | 82.0 |
| 11 | V422C | 68.3 | 81.9 |
| 12 | T437C | 67.9 | 82.1 |
| 13 | K360C | 70.1 | 82.1 |
| 14 | N384C | 68.7 | 81.8 |
| 15 | S440C | 69.4 | 81.9 |
| 16 | S442C | 68.4 | 81.9 |
| 17 | S415C | 68.7 | 82.0 |
| 18 | S383C | 68.8 | 81.9 |
| ***19*** | ***E380C*** | ***63.3*** | ***81.8*** |
| 20 | S239C | 69.8 | 81.8 |
| 21 | K326C | 66.5 | 81.8 |
| 22 | K290C | 72.2 | 82.0 |
| 23 | Q295C | 71.2 | 82.2 |
| 24 | Y296C | 70.6 | 81.9 |
| ***25*** | ***N297C*** | ***57.6*** | ***81.6*** |
| 26 | S298C | 72.0 | 82.6 |
| ***27*** | ***T299C*** | ***61.2*** | ***82.4*** |
| ***28*** | ***R301C*** | ***62.3*** | ***82.5*** |
| ***29*** | ***A118N NNAS*** | ***60.0*** | ***81.0*** |
| 30 | WT | 68.8 | 81.8 |

Fig. 4

| Mutants | Mono-PEGylated | Multi-PEGylated | Un-PEGylated | PAR | Notes/issues mAb |
|---|---|---|---|---|---|
| **A339C** | 77.6% | 11.7% | 10.7% | 2.1 | |
| A431C | 21.4% | 6.6% | 72.0% | 0.7 | |
| D413C | 53.2% | 12.5% | 34.3% | 1.6 | |
| E380C | 60.2% | 24.4% | 15.4% | 2.4 | Some free HL |
| **G385C** | 68.2% | 18.6% | 13.2% | 2.2 | Significant HMWS |
| **K274C** | 72.4% | 18.6% | 9.0% | 2.3 | |
| **K290C** | 72.6% | 8.9% | 18.5% | 1.9 | |
| K326C | 64.6% | 20.3% | 15.1% | 2.2 | |
| K360C | 65.0% | 15.1% | 19.9% | 2.0 | |
| K414C | 59.7% | 19.1% | 21.2% | 2.1 | |
| N297C | 73.1% | 5.5% | 21.4% | 1.7 | Significant free HL |
| N384C | 68.2% | 16.1% | 15.7% | 2.1 | |
| Q295C | 56.1% | 9.2% | 34.7% | 1.5 | |
| Q386C | 63.7% | 18.8% | 17.5% | 2.2 | Some HMWS |
| **Q418C** | 66.9% | 12.2% | 20.9% | 1.9 | Significant HMWS |
| R301C | 36.0% | 11.6% | 52.5% | 1.2 | Some free HL |
| S239C | 49.9% | 13.9% | 36.3% | 1.6 | |
| **S298C** | 76.6% | 5.9% | 17.5% | 1.8 | Significant free HL |
| S383C | 37.4% | 14.9% | 47.7% | 1.4 | |
| S415C | 60.1% | 22.7% | 17.3% | 2.3 | |
| **S440C** | 73.3% | 17.3% | 9.5% | 2.3 | |
| **S442C** | 72.4% | 16.2% | 11.4% | 2.2 | |
| T299C | 48.7% | 23.0% | 28.4% | 2.0 | |
| T437C | 66.1% | 17.8% | 16.1% | 2.2 | Some free HL |
| **V422C** | 71.9% | 18.7% | 9.4% | 2.3 | Some HMWS |
| Y296C | 50.7% | 4.8% | 44.5% | 1.0 | |
| Y300C | 43.9% | 18.9% | 37.2% | 1.7 | |

| | |
|---|---|
| 1 | Protein MW std |
| 2 | K290C+G385C |
| 3 | K290C+V422C |
| 4 | K290C+S440C |
| 5 | K290C+S442C |
| 6 | A339C+N384C |
| 7 | A339C+G385C |
| 8 | A339C+V422C |
| 9 | A339C+S442C |
| 10 | S442C+V422C |
| 11 | S440C+N384C |
| 12 | A118C+N384C |
| 13 | A118C+S440C |
| 14 | A118C+K274C |
| 15 | A118C+K360C |

Fig. 8

| Ab # | Antibody Mutations | nanoDSF Tm1 (°C) | nanoDSF Tm2 (°C) |
|---|---|---|---|
| 1 | WT parental antibody | 68.5 | 81.6 |
| 2 | K290C + G385C | 74.1 | 81.9 |
| 3 | K290C + V422C | 72.9 | 81.8 |
| 4 | K290C + S440C | 74.2 | 81.7 |
| 5 | K290C + S442C | 73.3 | 81.7 |
| **6** | **A339C + N384C** | **66.0** | **81.7** |
| **7** | **A339C + G385C** | **65.0** | **81.6** |
| **8** | **A339C + V422C** | **65.9** | **81.5** |
| **9** | **A339C + S442C** | **65.5** | **81.8** |
| 10 | S442C + V422C | 69.5 | 82.2 |
| 11 | S440C + N384C | 70.2 | 82.0 |
| 12 | A118C + N384C | 67.7 | 82.6 |
| 13 | A118C + G385C | 68.2 | 82.7 |
| 14 | A118C + V422C | 67.9 | 82.5 |
| 15 | A118C + S440C | 69.8 | 82.5 |
| 16 | A118C + S442C | 68.3 | 82.6 |
| 17 | A118C + K274C | 69.3 | 82.4 |

| Ab # | Antibody Mutations | nanoDSF Tm1 (°C) | nanoDSF Tm2 (°C) |
|---|---|---|---|
| **18** | **A118C + A339C** | **58.8** | **81.1** |
| 19 | A118C +K360C | 68.3 | 82.9 |
| 20 | A118C + Q418C | 69.0 | 82.8 |
| 21 | K274C + N384C | 69.6 | 81.8 |
| 22 | K274C + G385C | 70.8 | 81.7 |
| 23 | K274C + V422C | 69.9 | 81.7 |
| 24 | K274C + S440C | 71.7 | 81.7 |
| 25 | K274C + S442C | 69.5 | 81.9 |
| 26 | K274C + K360C | 70.4 | 82.2 |
| **27** | **K274C + A339C** | **66.4** | **81.8** |
| 28 | K274C + K414C | 72.3 | 82.2 |
| 29 | K360C + V422C | 68.6 | 81.8 |
| 30 | K360C + S440C | 69.3 | 82.0 |
| 31 | K360C + S442C | 69.0 | 82.0 |
| 32 | K360C + N384C | 69.0 | 82.2 |
| 33 | K360C + G385C | 68.3 | 81.9 |
| 34 | K360C + A339C | 66.9 | 82.0 |
| 35 | K360C + K290C | 72.5 | 82.5 |

Fig. 11

| Mutants | PAR | % Un-PEG | % Mono-&di-PEG | % Multi-PEG | SUM (% Mono-&di-PEG - % Un-PEGy - % Multi-PEG) |
|---|---|---|---|---|---|
| K360C + A339C | **3.95** | 5.02% | 81.63% | 13.35% | 0.633 |
| K274C + V422C | **3.68** | 0.82% | 91.98% | 7.21% | 0.840 |
| K274C + K360C | **3.60** | 4.11% | 85.73% | 10.16% | 0.715 |
| A339C +S440C | **3.54** | 2.60% | 87.92% | 9.48% | 0.76 |
| K274C + A339C | **3.50** | 2.03% | 90.80% | 7.16% | 0.816 |
| K274C + S440C | **3.49** | 1.47% | 94.03% | 4.50% | 0.881 |
| A118C + V422C | **3.49** | 2.33% | 92.35% | 5.32% | 0.847 |
| A118C + K274C | **3.48** | 2.47% | 92.80% | 4.73% | 0.856 |
| A339C + V422C | **3.46** | 2.00% | 92.88% | 5.12% | 0.858 |
| K274C + G385C | **3.45** | 2.36% | 92.92% | 4.60% | 0.860 |
| A339C + G385C | **3.44** | 2.55% | 91.98% | 5.48% | 0.840 |
| A118C + A339C | **3.43** | 5.44% | 85.53% | 9.02% | 0.71 |
| A339C + K290C | **3.42** | 4.09% | 87.02% | 9.00% | 0.74 |
| K274C + N384C | **3.41** | 2.76% | 92.10% | 5.14% | 0.842 |
| A118C + G385C | **3.39** | 3.70% | 90.86% | 5.44% | 0.817 |
| K290C + N384C | **3.38** | 4.39% | 87.16% | 8.46% | 0.74 |
| A118C + S440C | **3.38** | 3.03% | 92.98% | 3.99% | 0.860 |
| A339C + N384C | **3.37** | 3.22% | 91.87% | 4.91% | 0.837 |
| A118C + N384C | **3.35** | 3.42% | 91.99% | 4.58% | 0.840 |

Fig. 17

| Mutants | Mono-PEGylated | Multi-PEGylated | Un-PEGylated | PAR |
|---|---|---|---|---|
| A339C | 78.34% | 4.17% | 17.50% | 1.76 |
| A431C | 24.03% | 2.00% | 73.97% | 0.56 |
| D413C | 52.81% | 4.63% | 42.56% | 1.27 |
| E380C | 64.11% | 5.44% | 30.45% | 1.54 |
| G385C | 74.23% | 4.97% | 20.80% | 1.71 |
| K274C | 77.06% | 4.20% | 18.74% | 1.74 |
| K290C | 59.05% | 5.52% | 35.44% | 1.44 |
| K326C | 80.64% | 7.44% | 11.92% | 1.97 |
| K360C | 50.57% | 4.41% | 45.01% | 1.22 |
| K414C | 70.93% | 2.04% | 27.04% | 1.50 |
| N297C | 63.21% | 4.38% | 32.40% | 1.46 |
| N384C | 57.63% | 33.07% | 9.30% | 2.77 |
| Q295C | 55.17% | 7.07% | 31.67% | 1.42 |
| Q386C | 73.46% | 6.52% | 20.03% | 1.79 |
| Q418C | 58.19% | 1.85% | 39.96% | 1.24 |
| R301C | 68.76% | 7.48% | 23.76% | 1.74 |
| S239C | 54.74% | 5.10% | 40.17% | 1.33 |
| S298C | 80.44% | 3.58% | 15.98% | 1.77 |
| S383C | 27.32% | 1.51% | 71.17% | 0.61 |
| S415C | 67.77% | 1.86% | 30.37% | 1.43 |
| S440C | 68.15% | 4.86% | 26.99% | 1.59 |
| S442C | 57.40% | 4.30% | 38.30% | 1.35 |
| T299C | 78.87% | 11.54% | 9.59% | 2.14 |
| T437C | 54.15% | 4.58% | 41.27% | 1.30 |
| V422C | 64.16% | 2.22% | 33.62% | 1.37 |
| Y296C | 54.16% | 6.37% | 35.92% | 1.37 |
| Y300C | 71.52% | 5.97% | 22.52% | 1.72 |

Fig. 25

| Double cysteine mutants | PAR | % un-PEGylated | %mono- & di-PEGylated | % Multi- PEGylated | Selectivity ( % mono- & di-PEG - % un-PEG - % Multi-PEG) |
|---|---|---|---|---|---|
| A114C + A339C | GREEN | YELLOW | GREEN | GREEN | YELLOW |
| A114C + G385C | GREEN | GREEN | GREEN | GREEN | GREEN |
| A114C + K274C | GREEN | GREEN | GREEN | GREEN | GREEN |
| A114C + K290C | YELLOW | RED | GREEN | GREEN | YELLOW |
| A114C + K360C | YELLOW | GREEN | GREEN | GREEN | GREEN |
| A114c + N384C | YELLOW | GREEN | GREEN | GREEN | GREEN |
| A114C + Q418C | YELLOW | YELLOW | GREEN | GREEN | GREEN |
| A114C + S440C | GREEN | GREEN | GREEN | GREEN | GREEN |
| A114C + S442C | YELLOW | YELLOW | GREEN | GREEN | GREEN |
| A114C + V422C | GREEN | GREEN | GREEN | GREEN | GREEN |
| A339C + G385C | GREEN | GREEN | GREEN | GREEN | GREEN |
| A339C + K290C | GREEN | GREEN | GREEN | GREEN | YELLOW |
| A339C + N384C | GREEN | GREEN | GREEN | GREEN | GREEN |
| A339C + S442C | YELLOW | YELLOW | GREEN | GREEN | GREEN |
| A339C + V422C | GREEN | GREEN | GREEN | GREEN | GREEN |
| A339C +S440C | GREEN | GREEN | GREEN | GREEN | GREEN |
| K274C + A339C | GREEN | GREEN | GREEN | GREEN | GREEN |
| K274C + G385C | GREEN | GREEN | GREEN | GREEN | GREEN |
| K274C + K360C | GREEN | GREEN | GREEN | YELLOW | YELLOW |
| K274C + K414C | YELLOW | YELLOW | GREEN | GREEN | GREEN |
| K274C + N384C | YELLOW | GREEN | GREEN | GREEN | GREEN |
| K274C + S440C | GREEN | GREEN | GREEN | GREEN | GREEN |
| K274C + S442C | YELLOW | GREEN | GREEN | GREEN | GREEN |
| K274C + V442C | GREEN | GREEN | GREEN | GREEN | GREEN |
| K290C + G385C | YELLOW | GREEN | GREEN | GREEN | GREEN |
| K290C + N384c | GREEN | GREEN | GREEN | GREEN | YELLOW |
| K290C + S440C | YELLOW | GREEN | GREEN | GREEN | GREEN |
| K290C + S442C | YELLOW | YELLOW | GREEN | GREEN | GREEN |
| K290C + V422C | YELLOW | GREEN | GREEN | GREEN | GREEN |
| K360C + A339C | GREEN | GREEN | GREEN | YELLOW | YELLOW |
| K360C + G385C | YELLOW | YELLOW | GREEN | GREEN | GREEN |
| K360C + K290C | YELLOW | RED | YELLOW | GREEN | RED |
| K360C + N384C | YELLOW | YELLOW | GREEN | GREEN | YELLOW |
| K360C + S440C | YELLOW | GREEN | GREEN | GREEN | GREEN |
| K360C + S442C | YELLOW | RED | GREEN | GREEN | YELLOW |
| K360C + V422C | YELLOW | YELLOW | GREEN | GREEN | GREEN |
| S440C + N384C | YELLOW | YELLOW | GREEN | GREEN | GREEN |
| S442C + V422C | RED | RED | RED | GREEN | RED |

PAR: > 3.4 “Green” < 4; > 2.5 “Yellow” < 3.3;> 0 “Red” < 2.4

Mono-&di-PEGylated: > 85% “Green” < 100%; > 30% “Yellow” < 84.9%; > 5% “Red” < 29.9%

Multi-PEGylated: < 10% “Green” > 0%; > 10.1% “Yellow” <20%; > 20.1% “Red” < 100%

Un-PEGylated: < 6% “Green” > 0%; > 6.1% “Yellow” < 10%; > 10.1% “Red” < 100%

Selectivity: > 0.7 “Green” <1.0, > 0.51 “yellow” < 0.69, > 0 “red” < 0.5

MODIFIED BINDING POLYPEPTIDES FOR OPTIMIZED DRUG CONJUGATION

CROSS-REFERENCE TO RELATED APPLICATIONS

This application is a division of U.S. patent application Ser. No. 17/187,039, filed Feb. 26, 2021, now U.S. Pat. No. 11,879,004, which claims the benefit of U.S. Provisional Application Ser. No. 62/982,943, filed Feb. 28, 2020, the entire disclosures of which are hereby incorporated herein by reference.

FIELD OF THE INVENTION

This disclosure relates to compositions and methods of making double-engineered antigen-binding proteins for ligand conjugation.

BACKGROUND

The use of specific antigen-binding proteins, or antibodies, to treat people and other animals is a powerful tool that has been very effective in treating many conditions and disorders. However, there is great demand for more effective targeted therapeutics, especially target-specific therapies with higher efficacy and a greater therapeutic window. One of these target-specific treatments employs antibody-ligand conjugates in which a specific antibody is directed to a desired treatment site to deliver a ligand targeted to that site. This ligand can be a drug, such as a biologically active cytotoxic payload. The advantage of using antibody-ligand-conjugated molecules is that they can be designed to discriminate between healthy and diseased tissue. Indeed, such molecules have shown an improved therapeutic index, i.e., higher efficacy and/or lower toxicity profiles than un-targeted antibodies in a clinical setting. However, development of such therapeutics can be challenging, as many factors, including the antibody itself and linkage stability, can have significant impact on disease target (e.g., tumor) specificity, thereby reducing efficacy. Antibody-ligand conjugates demonstrating high non-specific binding and low stability in circulation are cleared while in transit through normal tissue, even before they reach the target site. Moreover, antibody-ligand conjugates with significant subpopulations of high drug load can generate aggregates that are eliminated by macrophages, leading to shorter half-life. Thus, there is an increasing need for critical process control and improvement of antibody-ligand conjugates, as well as preventing complications such as product aggregation and nonspecific toxicity.

A few antibody-ligand conjugates specific for certain indications have been approved in the United States. Examples are: brentuximab vedotin for relapsed or refractory Hodgkin lymphoma and systemic anaplastic large cell lymphoma (ALCL); trastuzumab emtansine for HER2+ breast cancer; inotuzumab ozogamicin for acute lymphoblastic leukemia (ALL); and gemtuzumab ozogamicin for relapsed acute myeloid leukemia (AML). However, there is still a need for antibody-ligand conjugates that are stable, can carry a high payload, i.e. a high ligand/drug to antibody ratio, and can be used for a variety of indications.

Herein, we disclose engineered antibodies that are stable and can be conjugated to a ligand or drug at a ligand/drug to antibody ratio of above 3, making these conjugates suitable for treatment of a variety of indications.

SUMMARY

The present disclosure provides an antigen-binding protein or a fragment thereof.

In one aspect, the disclosure provides an antigen-binding protein or fragment thereof, comprising an antibody heavy chain constant ($C_H$) domain comprising an engineered reactive amino acid residue at a first position and an engineered reactive amino acid residue at a second position; wherein, according to the numbering of the EU index of Kabat, the first position is position 274 and the second position is selected from the group consisting of: 339, 360, 384, 385, 422, 440, and any combination thereof.

In certain embodiments, the first position is position 274 and the second position is 339, according to the numbering of the EU index of Kabat. In certain embodiments, the first position is position 274 and the second position is 360, according to the numbering of the EU index of Kabat. In certain embodiments, the first position is position 274 and the second position is 384, according to the numbering of the EU index of Kabat. In certain embodiments, the first position is position 274 and the second position is 385, according to the numbering of the EU index of Kabat. In certain embodiments, the first position is position 274 and the second position is 422, according to the numbering of the EU index of Kabat. In certain embodiments, the first position is position 274 and the second position is 440, according to the numbering of the EU index of Kabat.

In certain embodiments, the antigen-binding protein or fragment thereof comprises a K274C amino acid substitution at the first position and a A339C amino acid substitution at the second position, according to the numbering of the EU index of Kabat. In certain embodiments, the antigen-binding protein or fragment thereof comprises a K274C amino acid substitution at the first position and a K360C amino acid substitution at the second position, according to the numbering of the EU index of Kabat. In certain embodiments, the antigen-binding protein or fragment thereof comprises a K274C amino acid substitution at the first position and a N384C amino acid substitution at the second position, according to the numbering of the EU index of Kabat. In certain embodiments, the antigen-binding protein or fragment thereof comprises a K274C amino acid substitution at the first position and a G385C amino acid substitution at the second position, according to the numbering of the EU index of Kabat. In certain embodiments, the antigen-binding protein or fragment thereof comprises a K274C amino acid substitution at the first position and a V422C amino acid substitution at the second position, according to the numbering of the EU index of Kabat. In certain embodiments, the antigen-binding protein or fragment thereof comprises a K274C amino acid substitution at the first position and a S440C amino acid substitution at the second position, according to the numbering of the EU index of Kabat.

In another aspect, the disclosure provides an antigen-binding protein or fragment thereof, comprising an antibody heavy chain constant ($C_H$) domain comprising an engineered reactive amino acid residue at a first position and an engineered reactive amino acid residue at a second position; wherein, according to the numbering of the EU index of Kabat, the first position is position 339 and the second position is selected from the group consisting of: 290, 360, 384, 385, 422, 440, and any combination thereof.

In certain embodiments, the first position is position 339 and the second position is 290, according to the numbering of the EU index of Kabat. In certain embodiments, the first position is position 339 and the second position is 360, according to the numbering of the EU index of Kabat. In certain embodiments, the first position is position 339 and the second position is 384, according to the numbering of the EU index of Kabat. In certain embodiments, the first position is position 339 and the second position is 385, according to the numbering of the EU index of Kabat. In certain embodiments, the first position is position 339 and the second position is 422, according to the numbering of the EU index of Kabat. In certain embodiments, the first position is position 339 and the second position is 440, according to the numbering of the EU index of Kabat.

In certain embodiments, the antigen-binding protein or fragment thereof comprises a A339C amino acid substitution at the first position and a K360C amino acid substitution at the second position, according to the numbering of the EU index of Kabat. In certain embodiments, the antigen-binding protein or fragment thereof comprises a A339C amino acid substitution at the first position and a N384C amino acid substitution at the second position, according to the numbering of the EU index of Kabat. In certain embodiments, the antigen-binding protein or fragment thereof comprises a A339C amino acid substitution at the first position and a G385C amino acid substitution at the second position, according to the numbering of the EU index of Kabat. In certain embodiments, the antigen-binding protein or fragment thereof comprises a A339C amino acid substitution at the first position and a V422C amino acid substitution at the second position, according to the numbering of the EU index of Kabat. In certain embodiments, the antigen-binding protein or fragment thereof comprises a A339C amino acid substitution at the first position and a S440C amino acid substitution at the second position, according to the numbering of the EU index of Kabat.

In another aspect, the disclosure provides an antigen-binding protein or fragment thereof, comprising an antibody heavy chain constant ($C_H$) domain comprising an engineered reactive amino acid residue at a first position and an engineered reactive amino acid residue at a second position; wherein, according to the numbering of the EU index of Kabat, the first position is position 118 and the second position is selected from the group consisting of: 274, 339, 384, 385, 422, 440, and any combination thereof.

In certain embodiments, the first position is position 118 and the second position is 274, according to the numbering of the EU index of Kabat. In certain embodiments, the first position is position 118 and the second position is 339, according to the numbering of the EU index of Kabat. In certain embodiments, the first position is position 118 and the second position is 384, according to the numbering of the EU index of Kabat. In certain embodiments, the first position is position 118 and the second position is 385, according to the numbering of the EU index of Kabat. In certain embodiments, the first position is position 118 and the second position is 422, according to the numbering of the EU index of Kabat. In certain embodiments, the first position is position 118 and the second position is 440, according to the numbering of the EU index of Kabat.

In certain embodiments, the antigen-binding protein or fragment thereof comprises a A118C amino acid substitution at the first position and a K274C amino acid substitution at the second position, according to the numbering of the EU index of Kabat. In certain embodiments, the antigen-binding protein or fragment thereof comprises a A118C amino acid substitution at the first position and a A339C amino acid substitution at the second position, according to the numbering of the EU index of Kabat. In certain embodiments, the antigen-binding protein or fragment thereof comprises a A118C amino acid substitution at the first position and a N384C amino acid substitution at the second position, according to the numbering of the EU index of Kabat. In certain embodiments, the antigen-binding protein or fragment thereof comprises a A118C amino acid substitution at the first position and a G385C amino acid substitution at the second position, according to the numbering of the EU index of Kabat. In certain embodiments, the antigen-binding protein or fragment thereof comprises a A118C amino acid substitution at the first position and a V422C amino acid substitution at the second position, according to the numbering of the EU index of Kabat. In certain embodiments, the antigen-binding protein or fragment thereof comprises a A118C amino acid substitution at the first position and a S440C amino acid substitution at the second position, according to the numbering of the EU index of Kabat.

In another aspect, the disclosure provides an antigen-binding protein or fragment thereof, comprising an antibody heavy chain constant ($C_H$) domain comprising an engineered reactive amino acid residue at a first position and an engineered reactive amino acid residue at a second position; wherein, according to the numbering of the EU index of Kabat, the first position is position 384 and the second position is selected from the group consisting of: 118, 274, 290, 339, and any combination thereof.

In certain embodiments, the first position is position 384 and the second position is 118, according to the numbering of the EU index of Kabat. In certain embodiments, the first position is position 384 and the second position is 274, according to the numbering of the EU index of Kabat. In certain embodiments, the first position is position 384 and the second position is 290, according to the numbering of the EU index of Kabat. In certain embodiments, the first position is position 339 and the second position is 118, according to the numbering of the EU index of Kabat.

In certain embodiments, the antigen-binding protein or fragment thereof comprises a N384C amino acid substitution at the first position and a A118C amino acid substitution at the second position, according to the numbering of the EU index of Kabat. In certain embodiments, the antigen-binding protein or fragment thereof comprises a N384C amino acid substitution at the first position and a K274C amino acid substitution at the second position, according to the numbering of the EU index of Kabat. In certain embodiments, the antigen-binding protein or fragment thereof comprises a N384C amino acid substitution at the first position and a K290C amino acid substitution at the second position, according to the numbering of the EU index of Kabat. In certain embodiments, the antigen-binding protein or fragment thereof comprises a N384C amino acid substitution at the first position and a A339C amino acid substitution at the second position, according to the numbering of the EU index of Kabat.

In certain embodiments, the engineered reactive amino acid residue is selected from the group consisting of: cysteine, lysine, histidine, serine, methionine, tryptophan, tyrosine, aspartate, glutamate, and arginine. In certain embodiments, the engineered reactive amino acid residue is cysteine. In certain embodiments, the engineered reactive amino acid residue is lysine.

In certain embodiments, the engineered reactive amino acid residue is conjugated to a ligand via a reactive moiety. In certain embodiments, the antigen-binding protein or fragment thereof further comprises a linker conjugating the engineered reactive amino acid residue to the ligand. In certain embodiments, the linker is cleavable. In certain embodiments, the linker is non-cleavable.

In certain embodiments, the antigen-binding protein or fragment thereof comprises a ligand to antibody ratio (LAR) of at least 3.0. In certain embodiments, the LAR is at least 3.4.

In certain embodiments, the ligand is a detection probe. In certain embodiments, the detection probe is selected from the group consisting of: a biotin, polyethylene glycol (PEG), fluorescent tag, visualization peptide, and a combination thereof. In certain embodiments, the detection probe is PEG.

In certain embodiments, the ligand is a targeting moiety. In certain embodiments, the targeting moiety is selected from the group consisting of: a protein, nucleic acid, lipid, carbohydrate, and a combination thereof.

In certain embodiments, the ligand is a drug.

In certain embodiments, the antigen-binding protein or fragment comprises a drug to antibody ratio (DAR) of at least 3.0. In certain embodiments, the DAR is at least 3.4.

In certain embodiments, the drug is a prodrug selected from the group consisting of: a phosphate-containing prodrug, amino acid-containing prodrug, thiophosphate-containing prodrug, sulfate-containing prodrug, peptide-containing prodrug, β-lactam-containing prodrug, phenoxyacetamide-containing prodrug, phenylacetamide-containing prodrug, 5-fluorocytosine prodrug, 5-fluorouridine prodrug, and any combination thereof.

In certain embodiments, the drug is selected from the group consisting of: an anti-cancer therapeutic agent, anti-inflammatory therapeutic agent, anti-infective therapeutic agent, anesthetic therapeutic agent, cytotoxic therapeutic agent, radionuclide, immunomodulator, cell signaling peptide, growth factor, enzyme, oligonucleotide, photoactive therapeutic agent, and any combination thereof.

In certain embodiments, the anti-cancer therapeutic agent is selected from the group consisting of: a cytostatic, cytotoxic nucleoside, tubulin binding agent, hormone and hormone antagonist, anti-angiogenesis agent, enzyme inhibitor, gene regulator, proteasome inhibitor, pteridine, diynene, podophyllotoxin, auristatin, geldanamycin, calicheamicin, gramicidin D, maytansanoids, neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, maytansine derivative, anthracycline derivative, bisphosphonate derivative, leptomycin derivative, streptonigrin derivative, auristatine derivative, duocarmycin derivative, and any combination thereof.

In certain embodiments, the cytostatic is selected from the group consisting of: an anthracine, DNA synthesis inhibitor, DNA-intercalator, DNA-RNA transcription regulator, ansamycin benzoquinone, quinonoid derivative, busulfan, ifosfamide, mechlorethamine, triaziquone, diaziquone, carbazilquinone, indoloquinone E09, diaziridinyl-benzoquinone methyl DZQ, triethylenephosphoramide, nitrosourea compound, and any combination thereof.

In certain embodiments, the cytotoxic nucleoside is selected from the group consisting of: adenosine arabinoside, cytarabine, cytosine arabinoside, 5-fluorouracil, fludarabine, floxuridine, ftorafur, 6-mercaptopurine, and any combination thereof.

In certain embodiments, the tubulin binding agent is selected from the group consisting of: taxoid, nocodazole, rhizoxin, dolastatin, colchicine, colchicinoid, combretastatin, vinca alkaloid, and any combination thereof.

In certain embodiments, the hormone and hormone antagonist is selected from the group consisting of: corticosteroid, progestin, estrogen, antiestrogen, androgen, aromatase inhibitor, 17-(allylamino)-17-demethoxygeldanamycin, 4-amino-I, 8-naphthalimide, apigenin, brefeldin A, cimetidine, dichloromethylene-diphosphonic acid, leuprolide, luteinizing hormone-releasing hormone, pifithrin-a, rapamycin, sex hormone-binding globulin, thapsigargin, and any combination thereof.

In certain embodiments, the anti-angiogenesis agent is selected from the group consisting of: Angiostatin Kl-3, DL-a-difluoromethyl-ornithine, endostatin, fumagillin, genistein, minocycline, staurosporine, (+)-thalidomide, and any combination thereof.

In certain embodiments, the enzyme inhibitor is selected from the group consisting of: S(+)-camptothecin, curcumin, (−)-deguelin, 5,6-diChlorobenz-imidazole I-β-D-ribofuranoside, etoposide, formestane, fostriecin, hispidin, 2-imino-1-imidazolidineacetic acid, mevinolin, trichostatin A, tyrphostin AG 34, tyrphostin AG 879, and any combination thereof.

In certain embodiments, the gene regulator is selected from the group consisting of: 5-aza-2'-deoxycytidine, 5-azacytidine, cholecalciferol, 4-hydroxytamoxifen, melatonin, mifepristone, raloxifene, trans-retinal, retinoic acid, vitamin A acid, 9-cis-retinoic acid, 13-cis-retinoic acid, retinol, tamoxifen, troglitazone, and any combination thereof.

In certain embodiments, the antigen-binding protein or fragment thereof further comprises an antibody heavy chain variable ($V_H$) domain.

In certain embodiments, the antigen-binding protein or fragment thereof further comprises an antibody light chain variable ($V_L$) domain.

In certain embodiments, the antigen-binding protein is a chimeric or humanized antibody. In certain embodiments, the antigen-binding protein is a human antibody. In certain embodiments, the antigen-binding protein is a monoclonal antibody.

In certain embodiments, the antigen-binding protein comprises one or more full-length antibody heavy chains comprising an Fc region. In certain embodiments, the Fc region is a human IgG1 Fc region.

In another aspect, the disclosure provides a method of producing an antigen-binding protein or fragment thereof, comprising an engineered reactive amino acid residue at a first position and an engineered reactive amino acid residue at a second position, the method comprising: (a) producing a first library of engineered parental antigen-binding proteins or fragments thereof, wherein each parental antigen-binding protein or fragment thereof comprises a first engineered reactive amino acid residue; (b) producing a second library of ligand-conjugated engineered parental antigen-binding proteins or fragments thereof by conjugating a ligand to the first engineered reactive amino acid residue of each engineered parental antigen-binding protein or fragment thereof in the first library; (c) producing a third library of engineered positions by screening the second library for a ligand to antibody ratio (LAR) above 1.7, wherein the positions at which the engineered parental antigen-binding proteins or fragments thereof with an LAR above 1.7 have an engineered reactive amino acid residue comprise the third library of engineered positions; (d) producing a fourth library of antigen-binding proteins or fragments thereof, wherein each antigen-binding protein or fragment thereof comprises an engineered reactive amino acid residue at a first position selected from the third library of engineered positions and an engineered reactive amino acid residue at a second position selected from the third library of engineered positions; (e) producing a fifth library of ligand-conjugated double-engineered antigen-binding proteins or fragments thereof by conjugating a ligand to the engineered reactive amino acid residue at the first position and the engineered reactive amino acid residue at the second position; and (f) producing a sixth library of double-engineered antigen-binding proteins or fragments thereof by screening the fifth library for an LAR above 3.4.

In certain embodiments, the method of producing an antigen-binding protein or fragment thereof further comprises producing a third library of engineered positions by screening the second library for conjugation of 60% or above of one ligand per single-engineered parental antigen-binding protein or fragment thereof, conjugation of 20% or below of multiple ligands per single-engineered parental antigen-binding protein or fragment thereof, and conjugation of 20% or below of no ligand per single-engineered parental antigen-binding protein or fragment thereof.

In certain embodiments, the method of producing an antigen-binding protein or fragment thereof further comprises producing a sixth library of double-engineered antigen-binding proteins or fragments thereof by screening the fifth library for conjugation of 80% or above of one or two ligands per double-engineered antigen-binding protein or fragment thereof, conjugation of 10% or below of multiple ligands per double-engineered antigen-binding protein or fragment thereof, and conjugation of 5% or below of no ligand per double-engineered antigen-binding protein or fragment thereof.

In certain embodiments, the method of producing an antigen-binding protein or fragment thereof further comprises conjugating a ligand to the engineered reactive amino acid residues of the double-engineered antigen-binding proteins or fragments thereof comprising the sixth library.

In certain embodiments, the engineered reactive amino acid residue is selected from the group consisting of: cysteine, lysine, histidine, serine, methionine, tryptophan, tyrosine, aspartate, glutamate, and arginine. In certain embodiments, the engineered reactive amino acid residue is cysteine. In certain embodiments, the engineered reactive amino acid residue is lysine. In certain embodiments, the engineered reactive amino acid residue is conjugated to a ligand via a reactive moiety.

In certain embodiments, the method of producing an antigen-binding protein or fragment thereof further comprises a linker conjugating the engineered reactive amino acid residue to the ligand. In certain embodiments, the linker is cleavable. In certain embodiments, the linker is non-cleavable.

In certain embodiments, the LAR is at least 3.0. In certain embodiments, the LAR is at least 3.4.

In certain embodiments, the ligand is a detection probe. In certain embodiments, the detection probe is selected from the group consisting of: a biotin, polyethylene glycol (PEG), fluorescent tag, visualization peptide, and a combination thereof. In certain embodiments, the detection prove is PEG.

In certain embodiments, the ligand is a targeting moiety. In certain embodiments, the targeting moiety is selected from the group consisting of: a protein, nucleic acid, lipid, carbohydrate, and a combination thereof.

In certain embodiments, the ligand is a drug.

In certain embodiments, the method of producing an antigen-binding protein or fragment thereof comprises a drug to antibody ratio (DAR) of at least 3.0. In certain embodiments, the DAR is at least 3.4

In certain embodiments, the drug is a prodrug selected from the group consisting of: a phosphate-containing prodrug, amino acid-containing prodrug, thiophosphate-containing prodrug, sulfate-containing prodrug, peptide-containing prodrug, β-lactam-containing prodrug, phenoxyacetamide-containing prodrug, phenylacetamide-containing prodrug, 5-fluorocytosine prodrug, 5-fluorouridine prodrug, and a combination thereof.

In certain embodiments, the drug is selected from the group consisting of: an anti-cancer therapeutic agent, anti-inflammatory therapeutic agent, anti-infective therapeutic agent, anesthetic therapeutic agent, cytotoxic therapeutic agent, radionuclide, immunomodulator, cell signaling peptide, growth factor, enzyme, oligonucleotide, photoactive therapeutic agent, and a combination thereof.

In certain embodiments, the anti-cancer therapeutic agent is selected from the group consisting of: a cytostatic, cytotoxic nucleoside, tubulin binding agent, hormone and hormone antagonist, anti-angiogenesis agent, enzyme inhibitor, gene regulator, proteasome inhibitor, pteridine, diynene, podophyllotoxin, auristatin, geldanamycin, calicheamicin, gramicidin D, maytansanoids, neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, maytansine derivative, anthracycline derivative, bisphosphonate derivative, leptomycin derivative, streptonigrin derivative, auristatine derivative, duocarmycin derivative, and any combination thereof.

In certain embodiments, the cytostatic is selected from the group consisting of: an anthracine, DNA synthesis inhibitor, DNA-intercalator, DNA-RNA transcription regulator, ansamycin benzoquinone, quinonoid derivative, busulfan, ifosfamide, mechlorethamine, triaziquone, diaziquone, carbazilquinone, indoloquinone E09, diaziridinyl-benzoquinone methyl DZQ, triethylenephosphoramide, nitrosourea compound, and any combination thereof.

In certain embodiments, the cytotoxic nucleoside is selected from the group consisting of: adenosine arabinoside, cytarabine, cytosine arabinoside, 5-fluorouracil, fludarabine, floxuridine, ftorafur, 6-mercaptopurine, and any combination thereof.

In certain embodiments, the tubulin binding agent is selected from the group consisting of: taxoid, nocodazole, rhizoxin, dolastatin, colchicine, colchicinoid, combretastatin, vinca alkaloid, and any combination thereof.

In certain embodiments, the hormone and hormone antagonist is selected from the group consisting of: corticosteroid, progestin, estrogen, antiestrogen, androgen, aromatase inhibitor, 17-(allylamino)-17-demethoxygeldanamycin, 4-amino-I, 8-naphthalimide, apigenin, brefeldin A, cimetidine, dichloromethylene-diphosphonic acid, leuprolide, luteinizing hormone-releasing hormone, pifithrin-a, rapamycin, sex hormone-binding globulin, thapsigargin, and any combination thereof.

In certain embodiments, the anti-angiogenesis agent is selected from the group consisting of: Angiostatin Kl-3, DL-a-difluoromethyl-ornithine, endostatin, fumagillin, genistein, minocycline, staurosporine, (+)-thalidomide, and any combination thereof.

In certain embodiments, the enzyme inhibitor is selected from the group consisting of: S(+)-camptothecin, curcumin, (−)-deguelin, 5,6-diChlorobenz-imidazole I-β-D-ribofuranoside, etoposide, formestane, fostriecin, hispidin, 2-imino-1-imidazolidineacetic acid, mevinolin, trichostatin A, tyrphostin AG 34, tyrphostin AG 879, and any combination thereof.

In certain embodiments, the gene regulator is selected from the group consisting of: 5-aza-2'-deoxycytidine, 5-azacytidine, cholecalciferol, 4-hydroxytamoxifen, melatonin, mifepristone, raloxifene, trans-retinal, retinoic acid, vitamin A acid, 9-cis-retinoic acid, 13-cis-retinoic acid, retinol, tamoxifen, troglitazone, and any combination thereof.

In certain embodiments, the method of producing an antigen-binding protein or fragment thereof further comprises an antibody heavy chain variable ($V_H$) domain. In certain embodiments, the method of producing an antigen-binding protein or fragment thereof further comprises an antibody light chain variable ($V_L$) domain.

In certain embodiments, the antigen-binding protein is a chimeric or humanized antibody. In certain embodiments, the antigen-binding protein is a human antibody. In certain embodiments, the antigen-binding protein is a monoclonal antibody.

In certain embodiments, the antigen-binding protein comprises one or more full-length antibody heavy chains comprising an Fc region. In certain embodiments, the Fc region is a human IgG1 Fc region.

In another aspect, the disclosure provides a pharmaceutical composition comprising any of the antigen-binding proteins or fragments thereof disclosed herein, further comprising a pharmaceutically acceptable carrier.

In another aspect, the disclosure provides a method of treating a disease or disorder in a subject, comprising administering to a subject in need thereof any of the antigen-binding proteins or fragments thereof disclosed herein or the pharmaceutical composition disclosed herein.

In another aspect, the disclosure provides an isolated nucleic acid molecule encoding any of the antigen-binding proteins or fragments thereof disclosed herein.

In another aspect, the disclosure provides an expression vector comprising the nucleic acid molecule disclosed herein.

In another aspect, the disclosure provides a host cell comprising the expression vector disclosed herein.

BRIEF DESCRIPTION OF THE DRAWINGS

FIG. 2 depicts nano DSF measurements of single-engineered parental antibodies. Nano DSF (Differential Scanning fluorimetry) measurements were performed to measure the stability of single-engineered parental antibodies (mutants) with a first position cysteine mutation. Two melting points ($Tm_1$ and $Tm_2$) were measured, corresponding to the melting temperatures at which 50% of two globular regions of the antibodies were unfolded. Engineered antibodies with $Tm_1 \geq 5$ degrees C. lower than an un-engineered antibody control are shown in bold text. All engineered antibodies were comparable or slightly more stable than the control for $Tm_2$.

FIG. 4 depicts a comparison of single-engineered parental antibodies using a heat map. Single-engineered parental antibodies (mutants) with a first position cysteine mutation were analyzed based on four criteria: % mono-PEGylated, % multi-PEGylated, PAR (PEG to antibody ratio), and % un-PEGylated, as measured by Coomassie stain. The shading for each criterion (column) is as follows:

Mono-PEGylated: >60% to <100%—light grey, >30% to <59.9%—unshaded; >5% to <29.9%—dark grey;

Multi-PEGylated: >0% to <15%—light grey, >15.1% to <20%—unshaded, >20.1% to <100%—dark grey;

PAR: >1.7 to <2.5—light grey, >1 to <1.69—unshaded, >0 to <0.99—dark grey;

Un-PEGylated: >0% to <15%—light grey, >15.1% to <20%—unshaded, >2.1% to <100%—dark grey.

Figure 5:
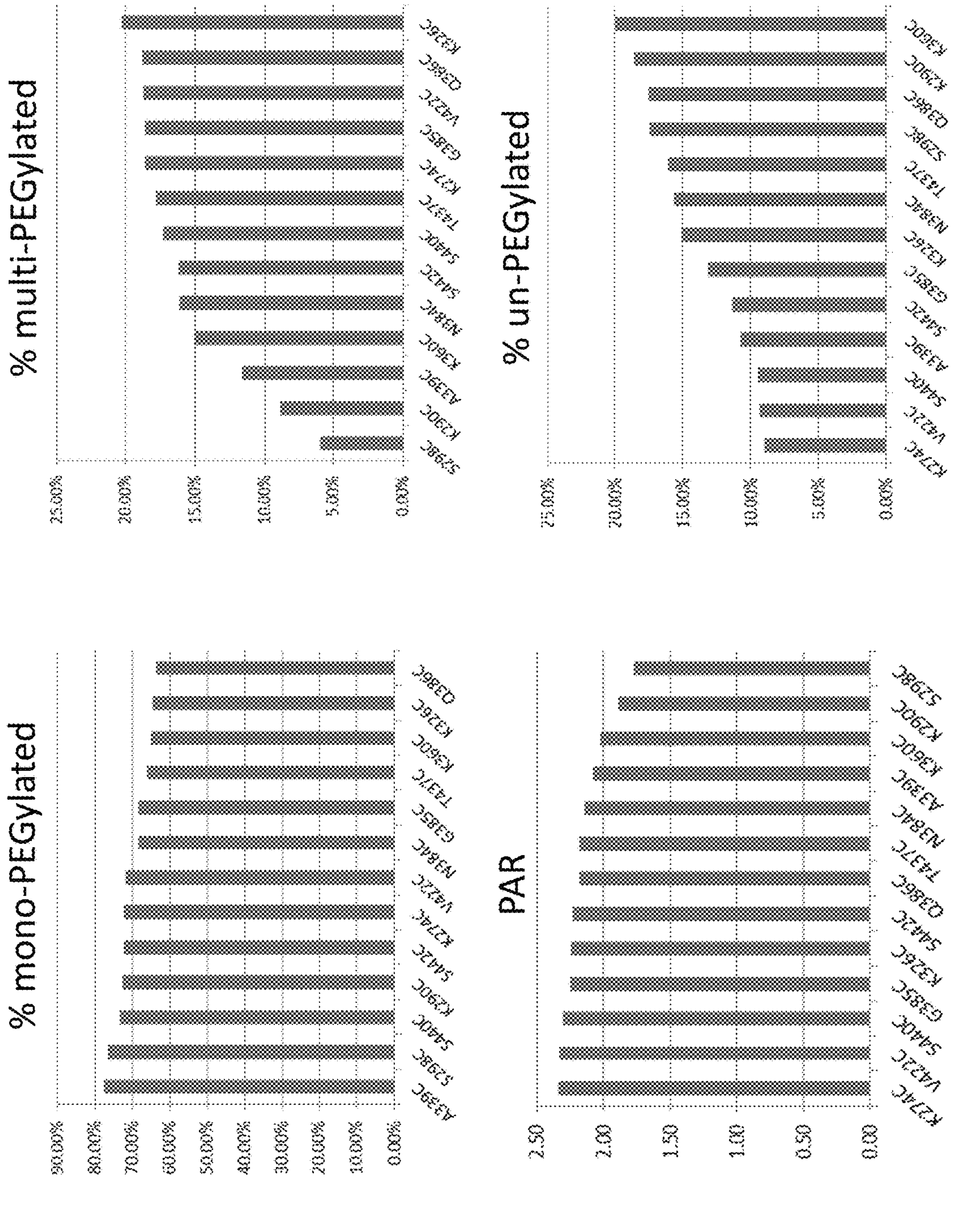

FIG. 5 depicts the top single-engineered parental antibodies selected. Selection of the single-engineered parental antibodies (mutants) with a first position cysteine mutation was based on four criteria: ≥60% mono-PEGylated, ≤20% multi-PEGylated, PAR (PEG to antibody ratio) ≥>1.7, and ≤20% un-PEGylated, as measured by Coomassie stain.

Figure 6:
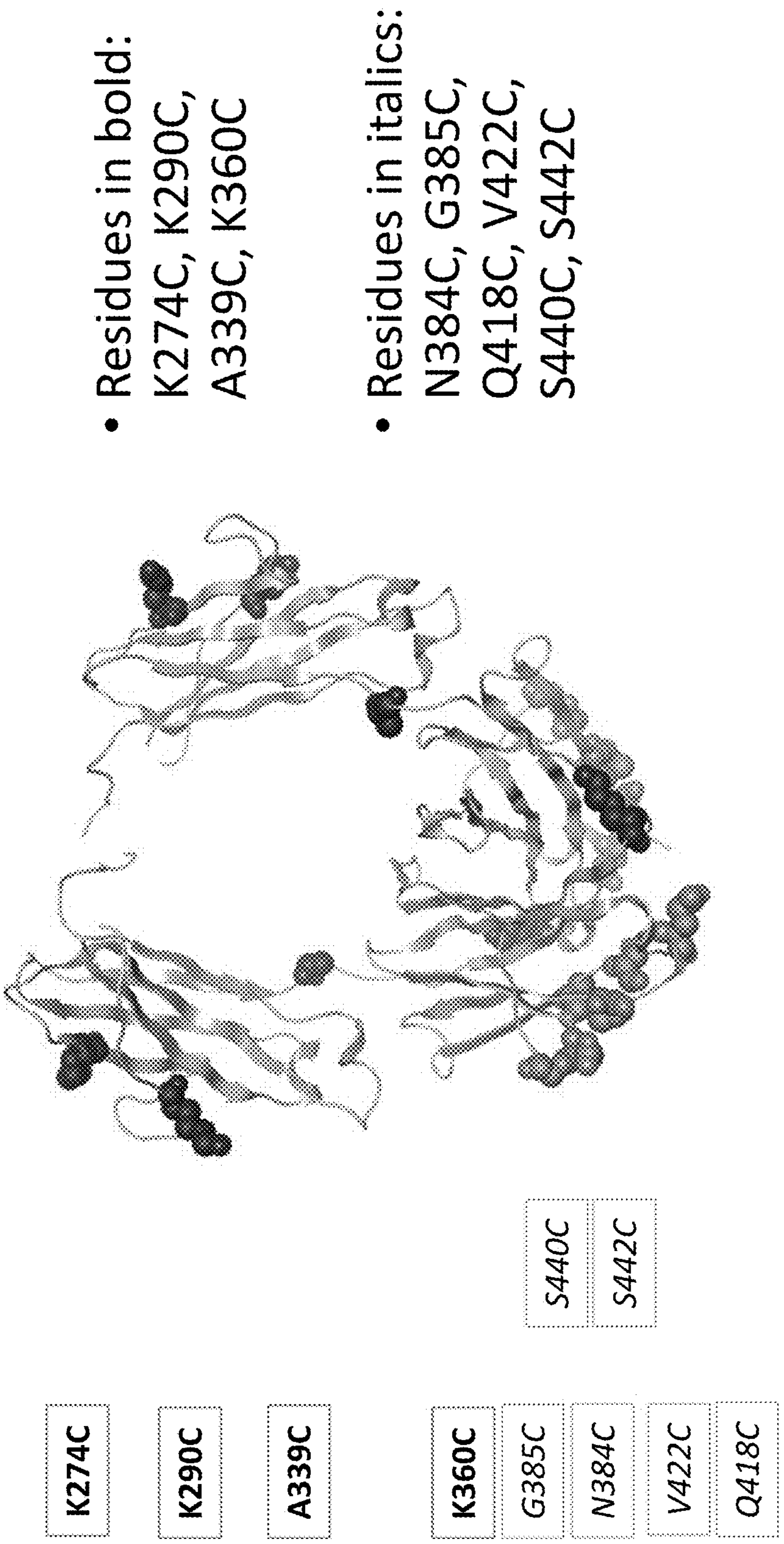

FIG. 6 depicts the top ten single-engineered parental antibodies selected. In bold are depicted first positions K274C, K290C, A339C, K360C and in italics are depicted first positions N384C, G385C, Q418C, V422C, S440C, S442C.

Figure 7:
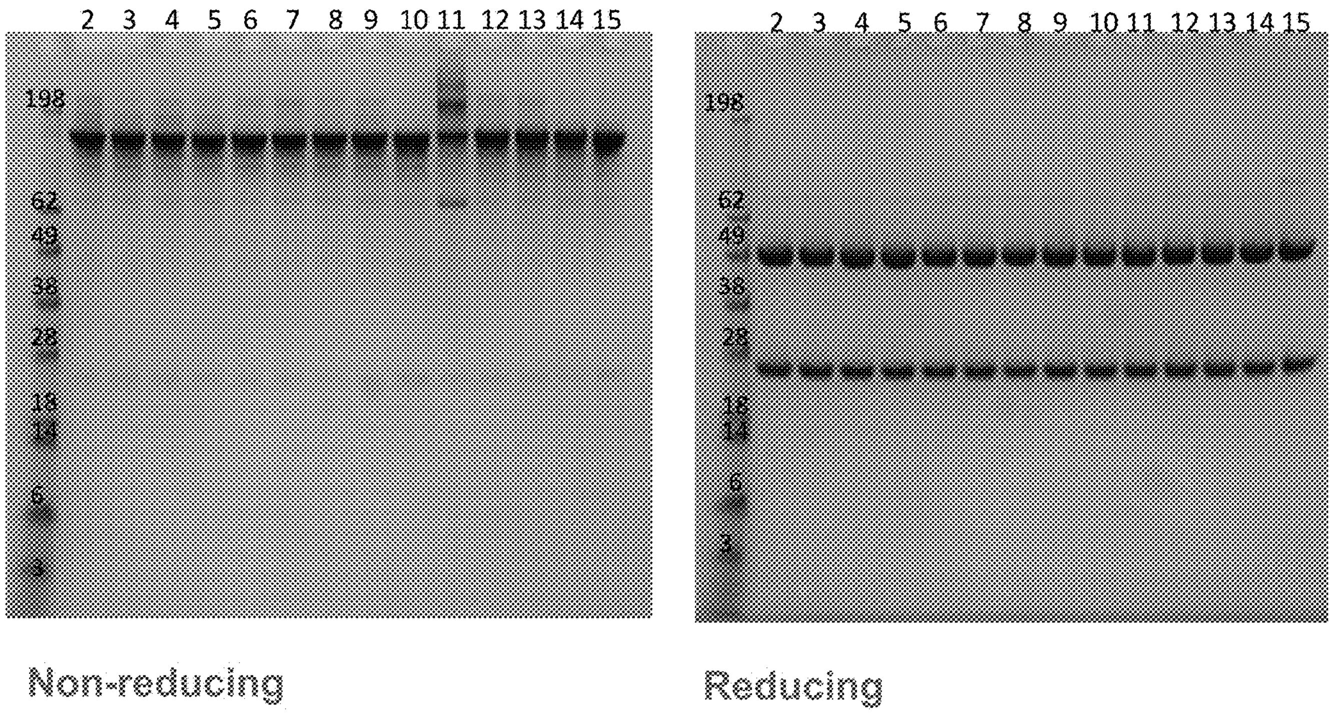

FIG. 7 depicts purified double-engineered antibodies on SDS-PAGE. Double-engineered antibodies (mutants) with a first position cysteine mutation and a second position cysteine mutation were loaded onto SDS-PAGE gels under reducing and non-reducing conditions.

FIG. 8 depicts nano DSF measurements of double-engineered antibodies. Nano DSF (Differential Scanning fluorimetry) measurements were performed to measure the stability of double-engineered antibodies (mutants) with a first position cysteine mutation and a second position cysteine mutation. Two melting points ($Tm_1$ and $Tm_2$) were measured, corresponding to the melting temperatures at which 50% of two globular regions of the antibodies were unfolded. Engineered antibodies with $Tm_1$ and $Tm_2$>2 degrees C. lower (bold text) or <2 degrees C. higher (underlined, italicized text) than an un-engineered antibody control are indicated.

Figure 9:
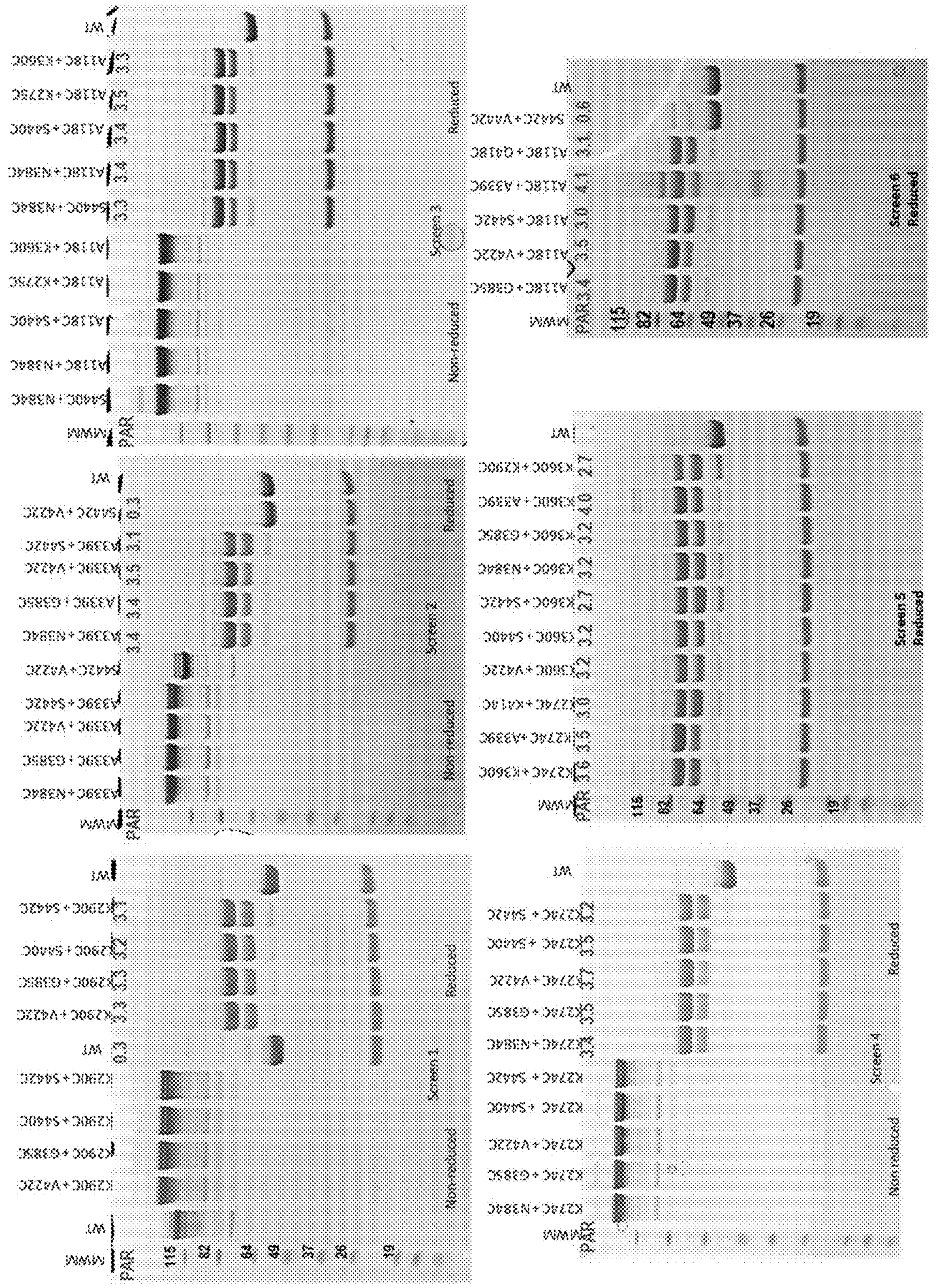

FIG. 9 depicts PEGylation screening of double-engineered antibodies. Double-engineered antibodies (mutants) with a first position cysteine mutation and a second position cysteine mutation were conjugated with PEG and then screened with DTT reductant by loading onto PEG-stained SDS-PAGE with 64 eq DTT for uncapping. Each mutant antibody shown was screened using reducing and non-reducing conditions to determine its PEG to antibody ratio (PAR).

Figure 10:
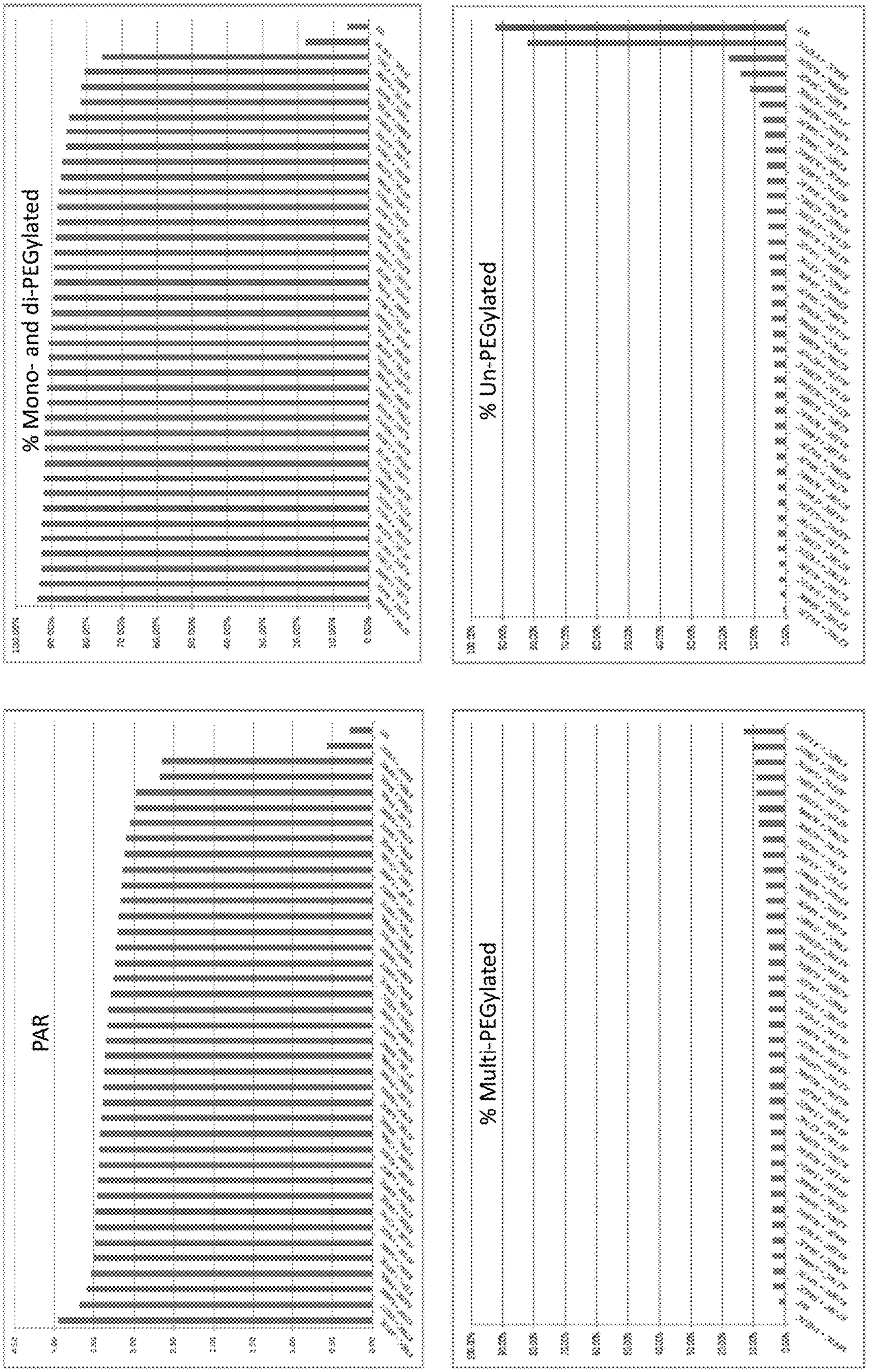

FIG. 10 depicts PEGylation efficiency/selectivity among double-engineered antibodies. Double-engineered antibodies (mutants) with a first position cysteine mutation and a second position cysteine mutation were assessed for four criteria: PAR, % mono- and di-PEGylated, % multi-PEGylated, and % un-PEGylated, as measured by Coomassie stain.

FIG. 11 depicts the top 19 double-engineered antibodies selected. Selection of the double-engineered antibodies (mutants) with a first position cysteine mutation and a second position cysteine mutation was based on four criteria: ≥80% mono- and di-PEGylated, ≤10% multi-PEGylated, PAR ≥3.4, and ≤5% un-PEGylated, as measured by Coomassie stain.

Figure 12:

FIG. 12 depicts the top double-engineered antibodies selected with the first position being K274C.

Figure 13:

FIG. 13 depicts the top double-engineered antibodies selected with the first position being A339C.

Figure 14:
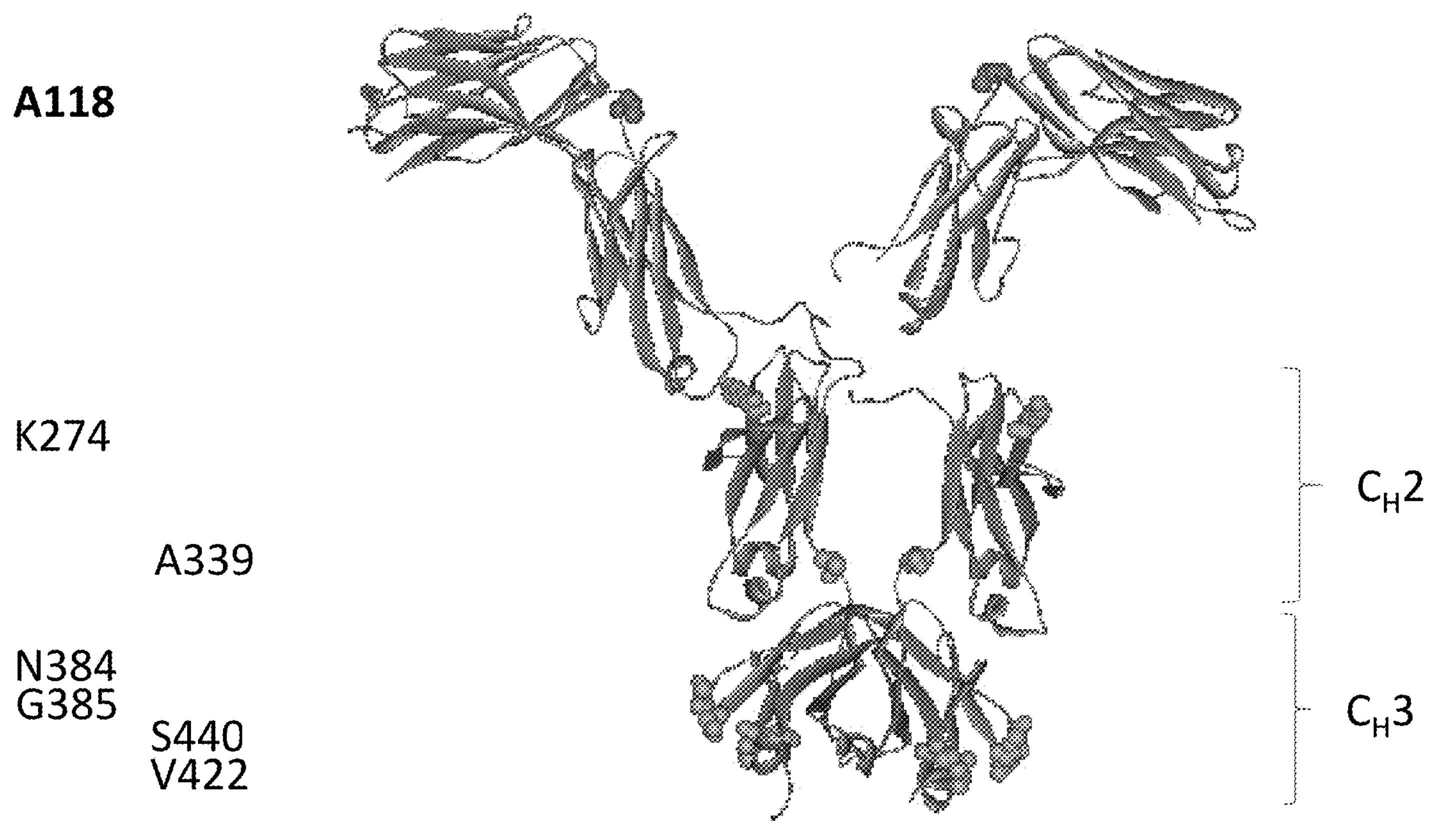

FIG. 14 depicts the top double-engineered antibodies selected with the first position being A118C.

Figure 15:
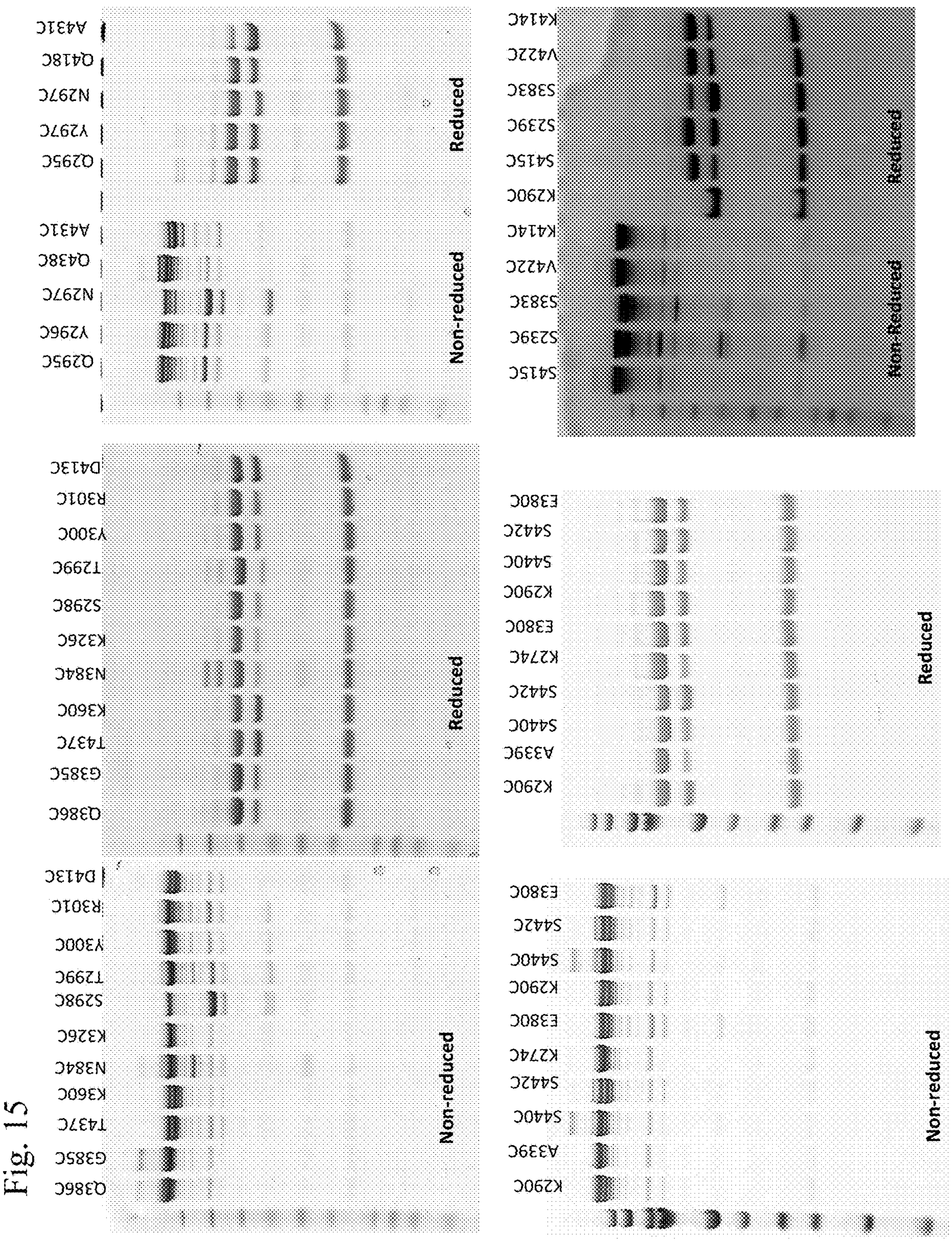

FIG. 15 depicts screening of single-engineered parental antibodies with reductant tris(2-carboxyethyl)phosphine (TCEP). Single-engineered parental antibodies (mutants) with a first position cysteine mutation were screened with TCEP by loading onto PEG-stained SDS-PAGE. Each engineered antibody depicted was screened using reducing and non-reducing conditions.

Figure 16:
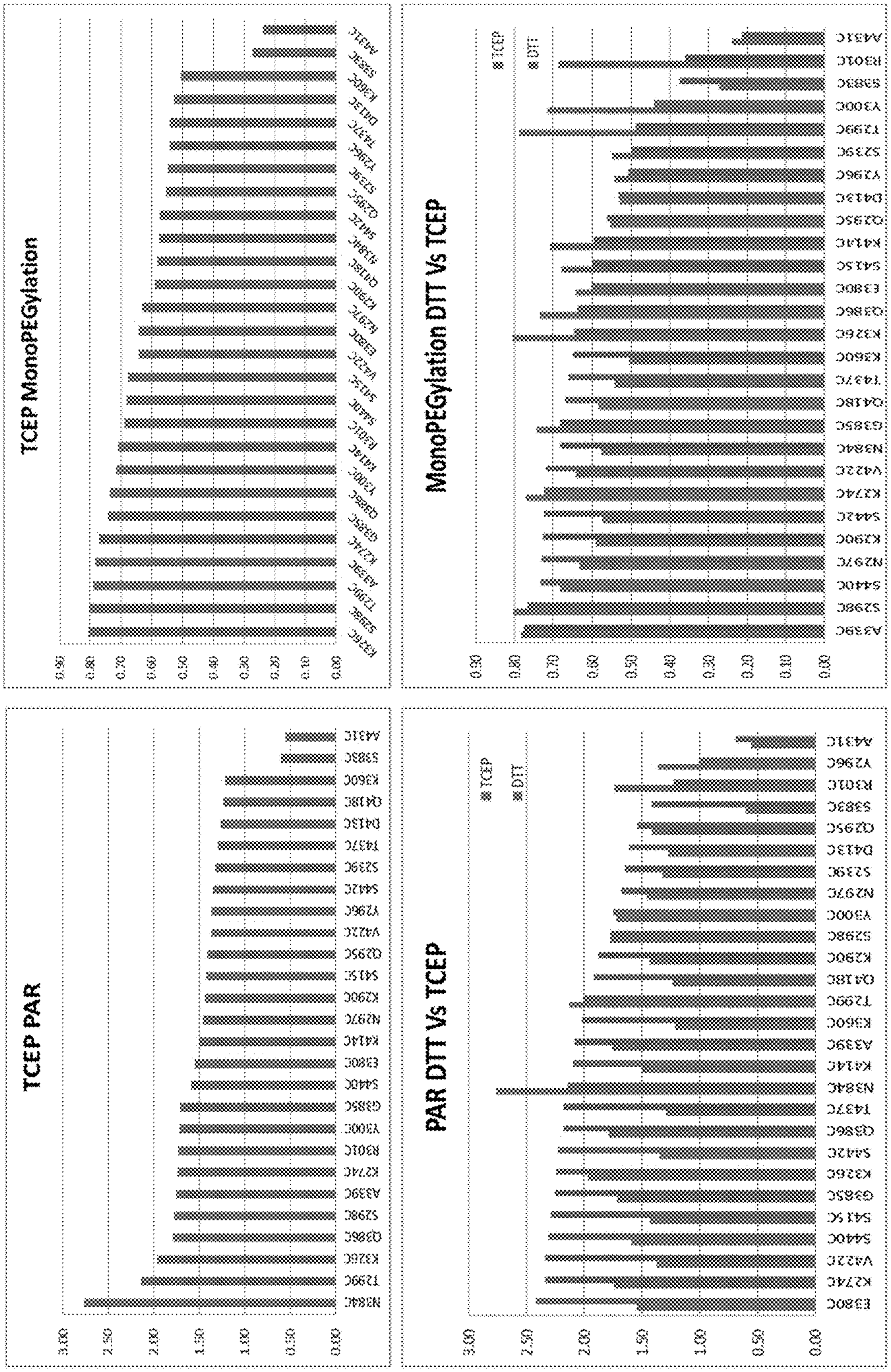
Figure 16:
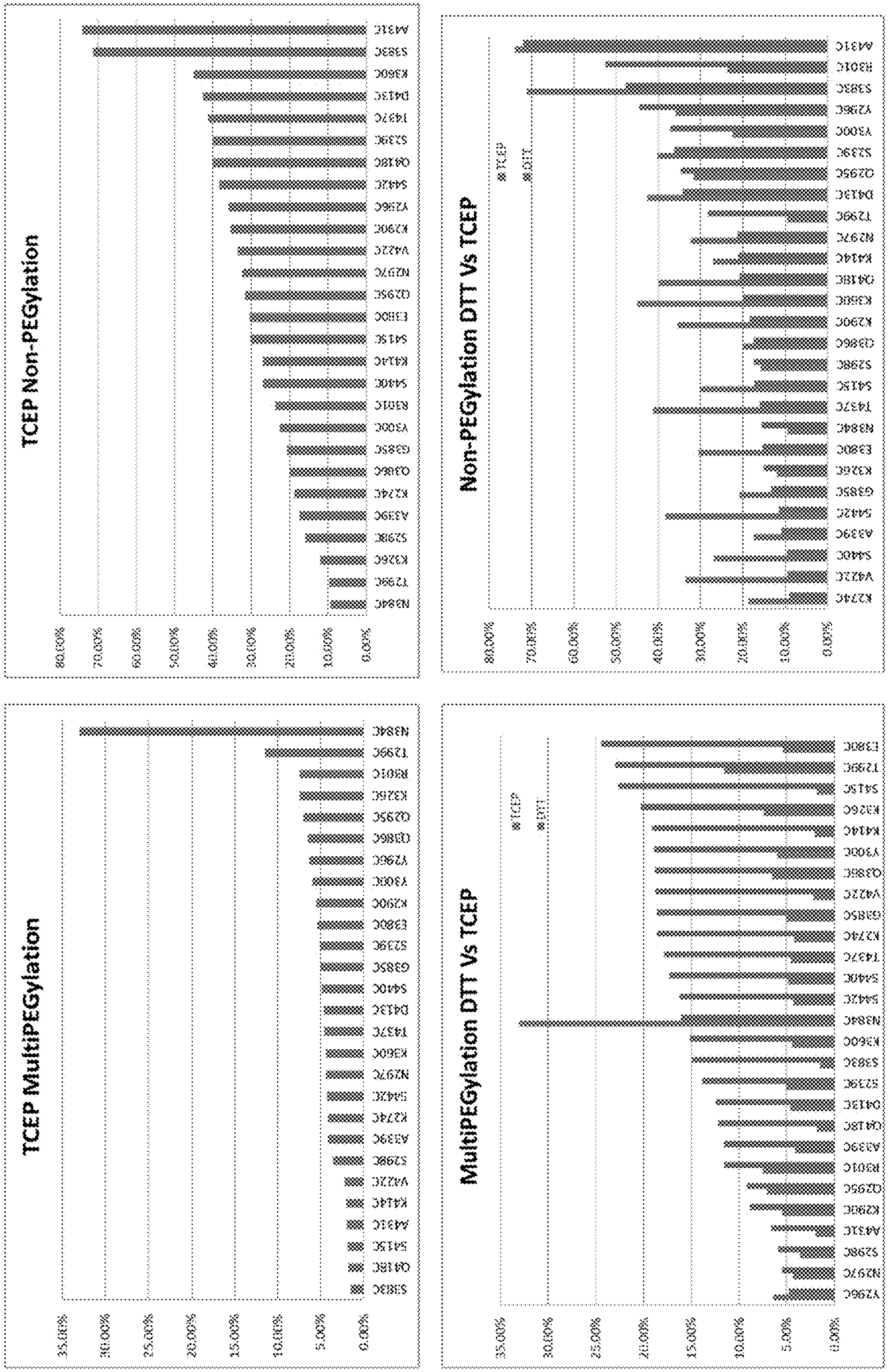

FIG. 16 depicts a comparison between TCEP-treated and DTT-treated single-engineered parental antibodies. Comparison was made on four criteria: mono-PEGylated, multi-PEGylated, PAR (PEG to antibody ratio), and Non-PEGylated, as measured by Coomassie stain.

FIG. 17 depicts a comparison of single-engineered parental antibodies using a heat map for TCEP-treated antibodies. Single-engineered parental antibodies (mutants) with a first position cysteine mutation were analyzed based on four criteria: % mono-PEGylated, % multi-PEGylated, PAR (PEG to antibody ratio), and % un-PEGylated, as measured by Coomassie stain. The shading for each criterion (column) is as follows:

Mono-PEGylated: >60% to <100%—light grey, >30% to <59.9%—unshaded; >5% to <29.9%—dark grey;

Multi-PEGylated: >0% to <15%—light grey, >15.1% to <20%—unshaded, >20.1% to <100%—dark grey;

PAR: >1.7 to <2.5—light grey, >1 to <1.69—unshaded, >0 to <0.99—dark grey;

Un-PEGylated: >0% to <15%—light grey, >15.1% to <20%—unshaded, >2.1% to <100%—dark grey.

Figure 18:
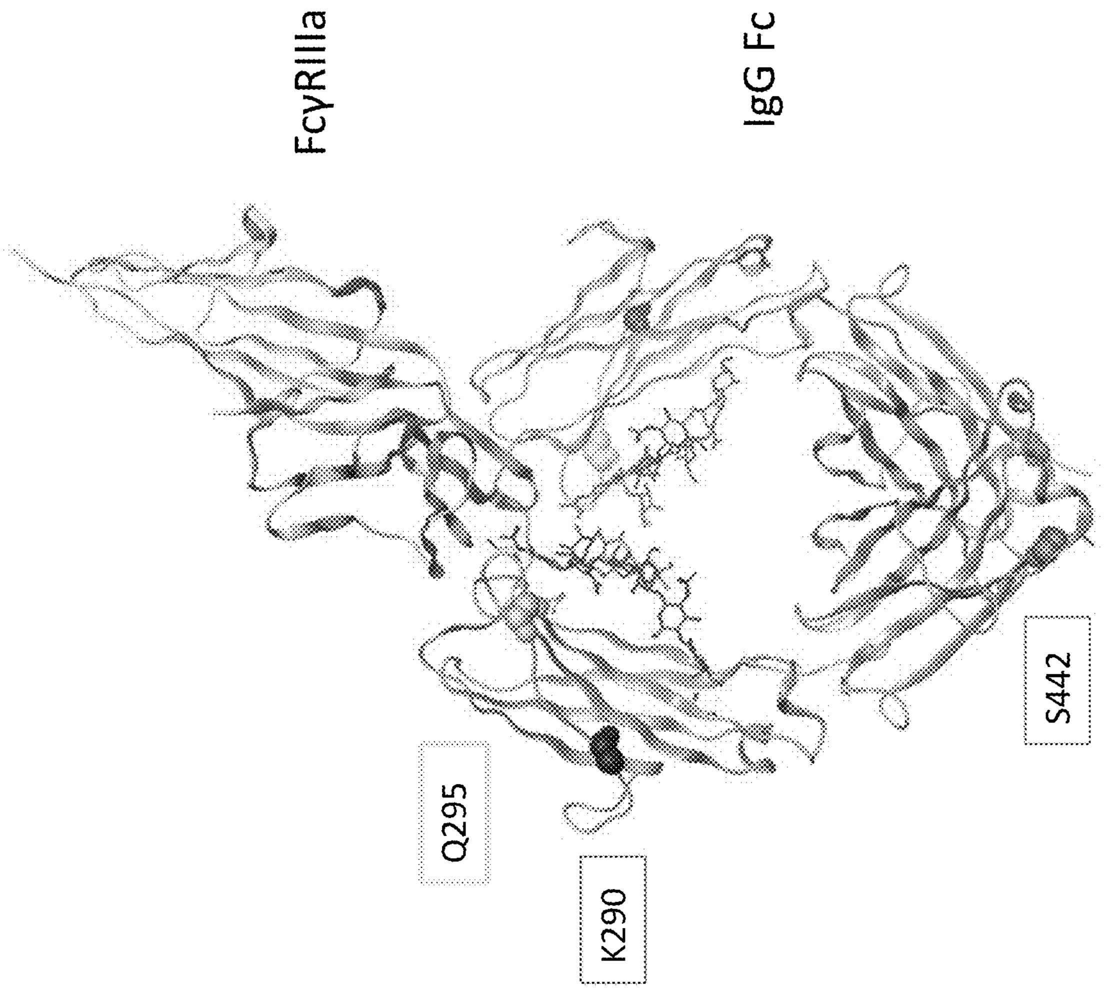

FIG. 18 depicts three single-engineered parental antibody sites used for conjugation and test for effects on FcγRIIIa binding. Sites tested were K290, Q295, and S442.

Figure 19:
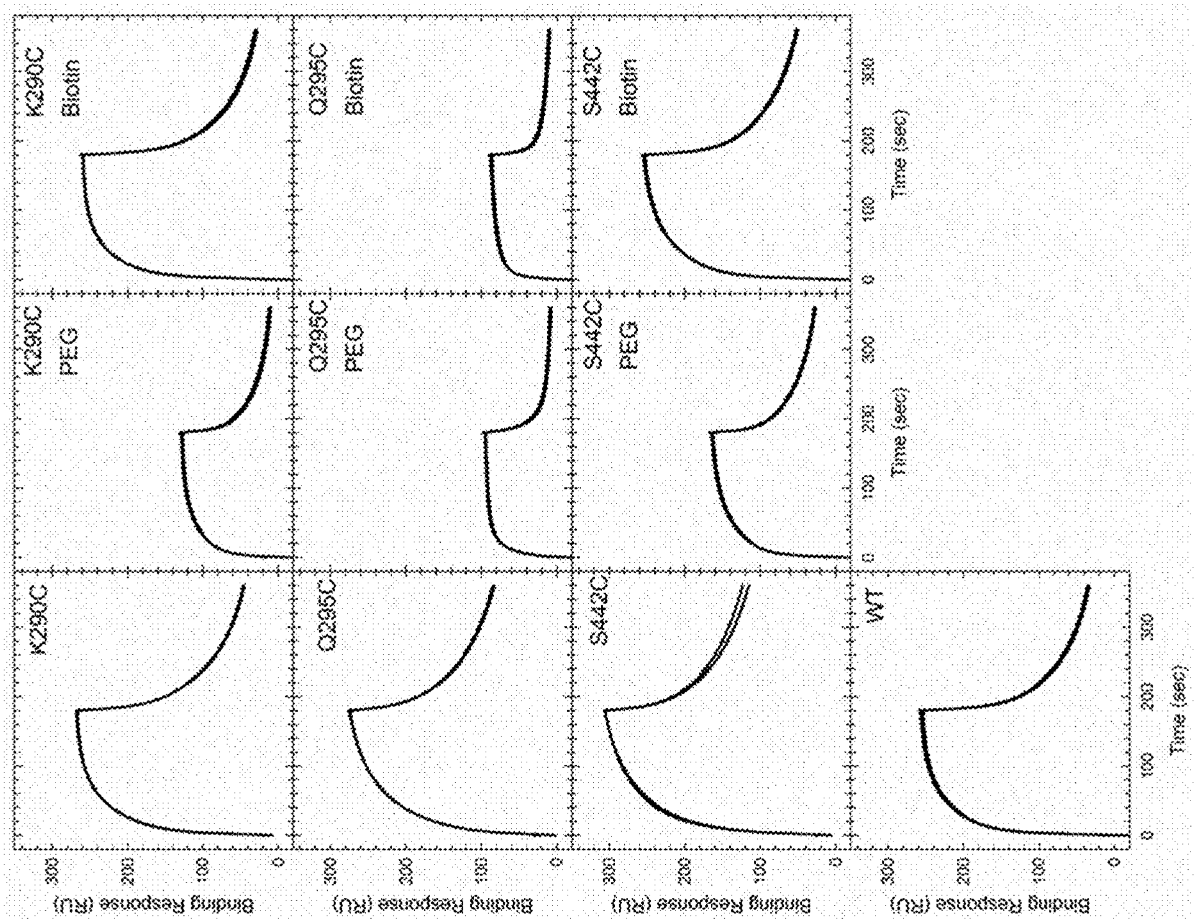

FIG. 19 depicts kinetic sensorgram graphs demonstrating binding of FcγRIIIa to each of the single-engineered parental antibody sites used for conjugation. Sites tested were K290, Q295, and S442. Each site was conjugated with either 2 kDa maleimide PEG or biotin.

Figure 20:
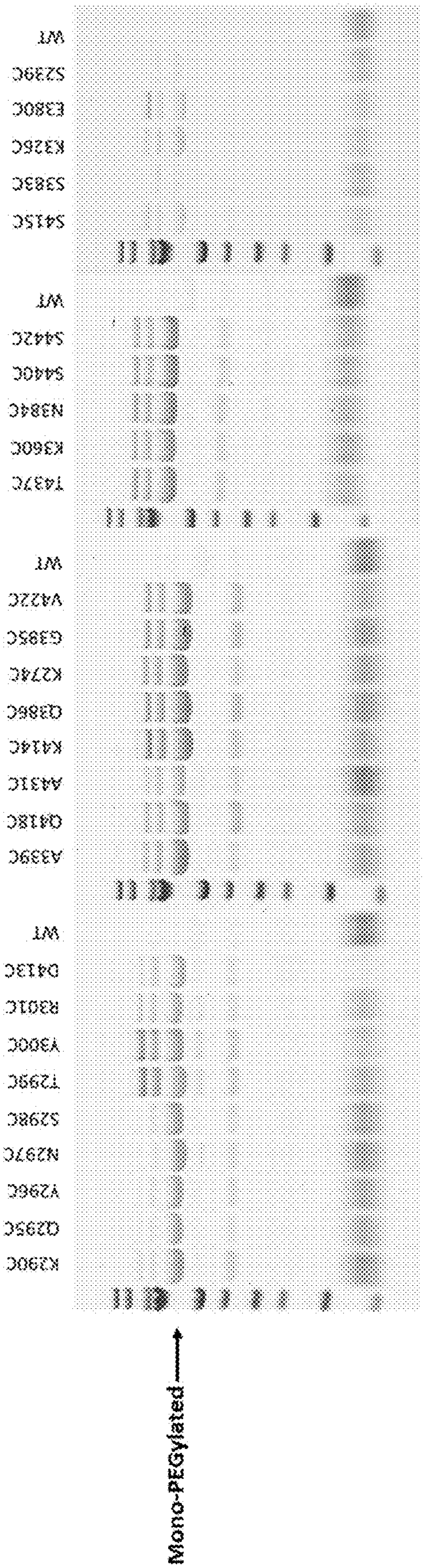

FIG. 20 depicts an SDS-PAGE and PEG staining of single cysteine engineered parental antibodies that have been conjugated to PEG. 27 single cysteine engineered parental antibodies that were PEGylated (13 μg each) were analyzed using 4-12% Bis-Tris NuPAGE under reducing conditions. The gels were stained using PEG staining. The wild-type antibody (WT), which was also PEGylated, was used as a control. PageRuler prestained protein ladder was used as protein molecular weight standards (MW Std).

Figure 21:
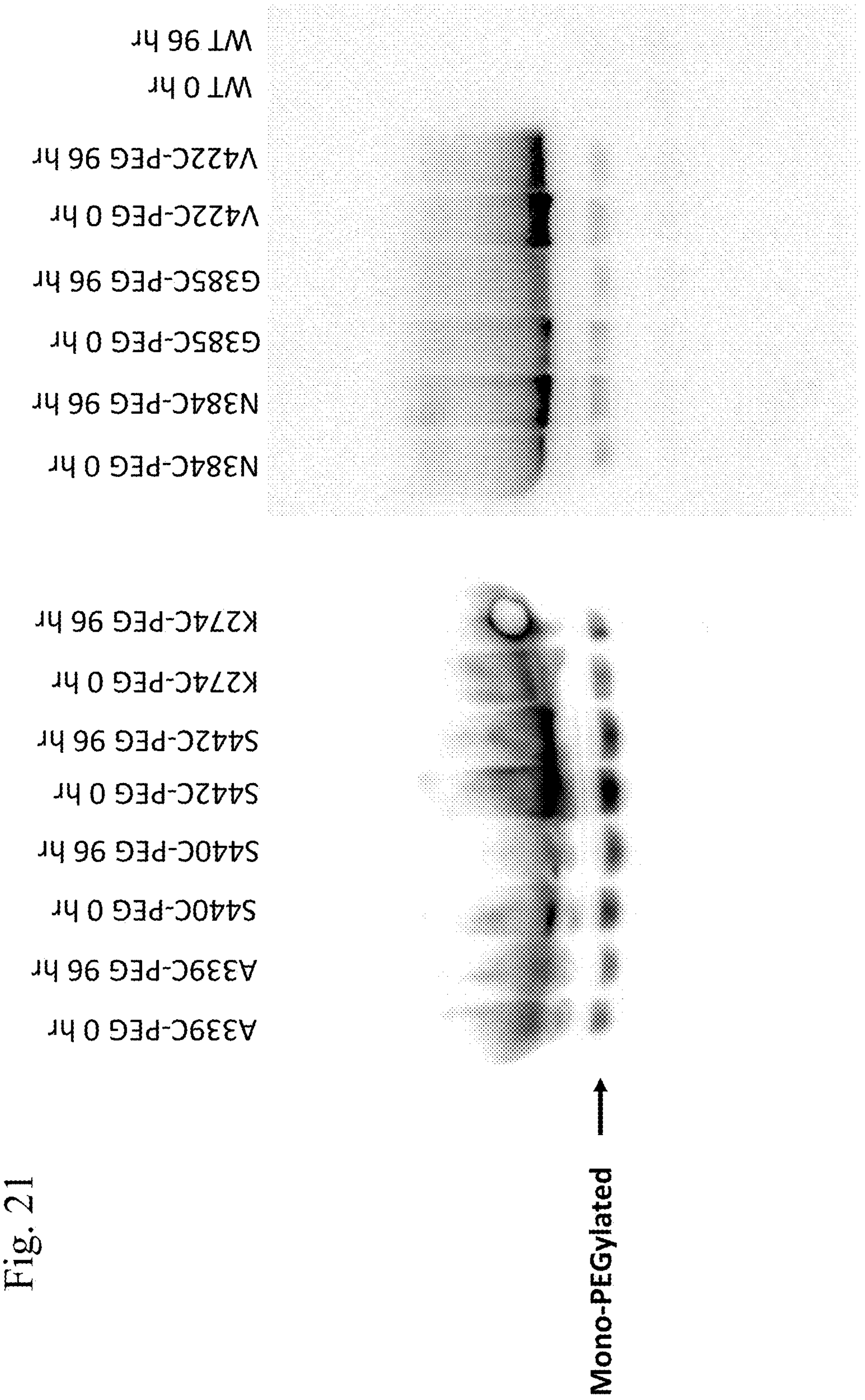

FIG. 21 depicts a western blot against PEGylated antibody samples (0.1 μg) incubated with mouse plasma with an anti-PEG antibody. The mono-PEGylated antibody bands, as shown by arrow, were analyzed using AlphaView software to determine the amount of PEG remained after incubation in plasma for 96 hrs. The diffuse bands above the mono-PEGylated antibody bands are multi-PEGylated species which reacts strongly to the anti-PEG antibody due to the presence of more PEG.

Figure 22:
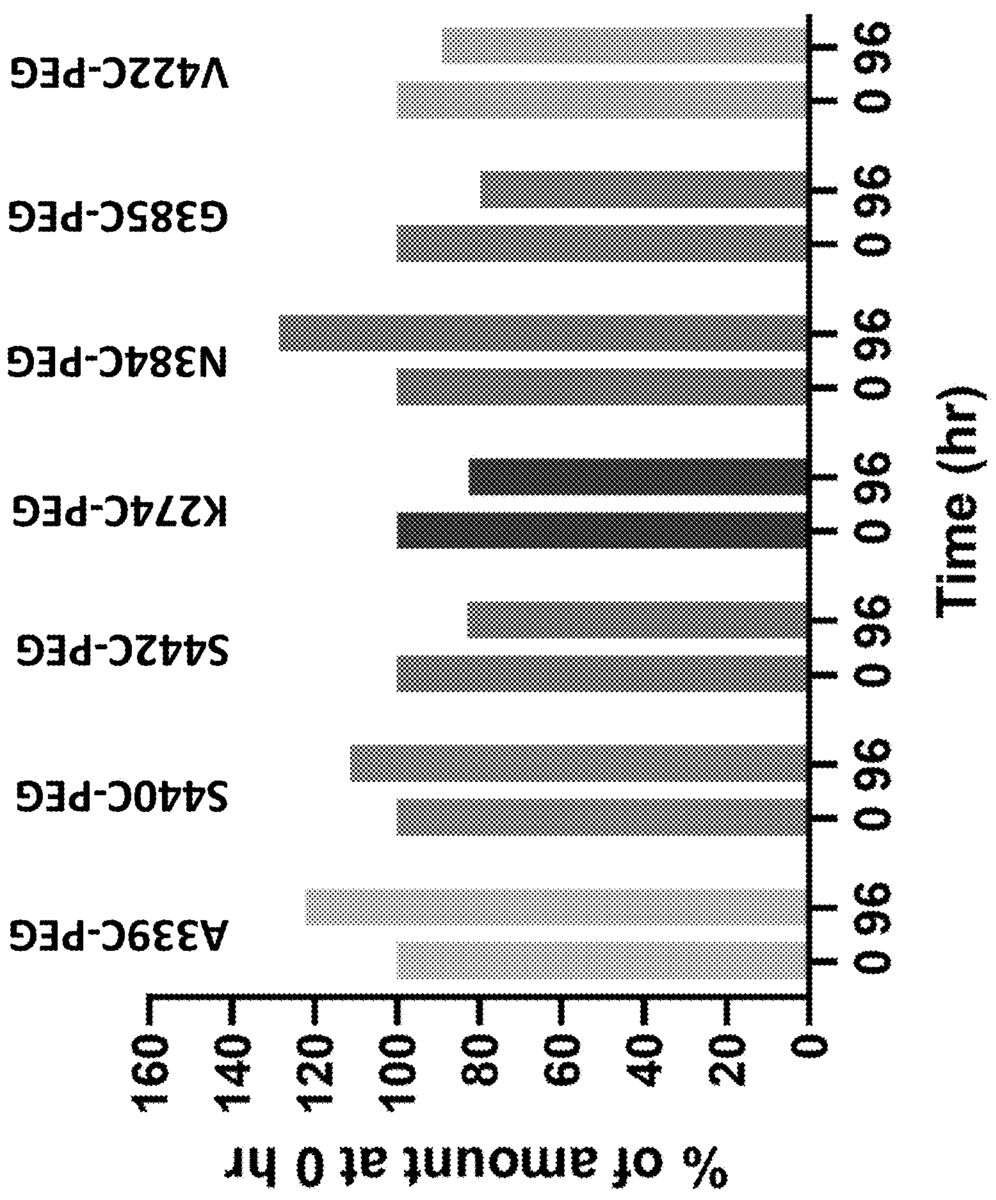

FIG. 22 depicts the quantification of a western blot with an anti-PEG antibody against PEGylated single cysteine mutants. The PEGylated antibodies were incubated with mouse plasma for 0 and 96 hrs before being analyzed using western blot with anti-PEG antibody. The percent of amount at 0 hr represents the band area of mono-PEGylated antibody bands from sample at 96 hrs. divided by that at 0 hr.×100.

Figure 23:
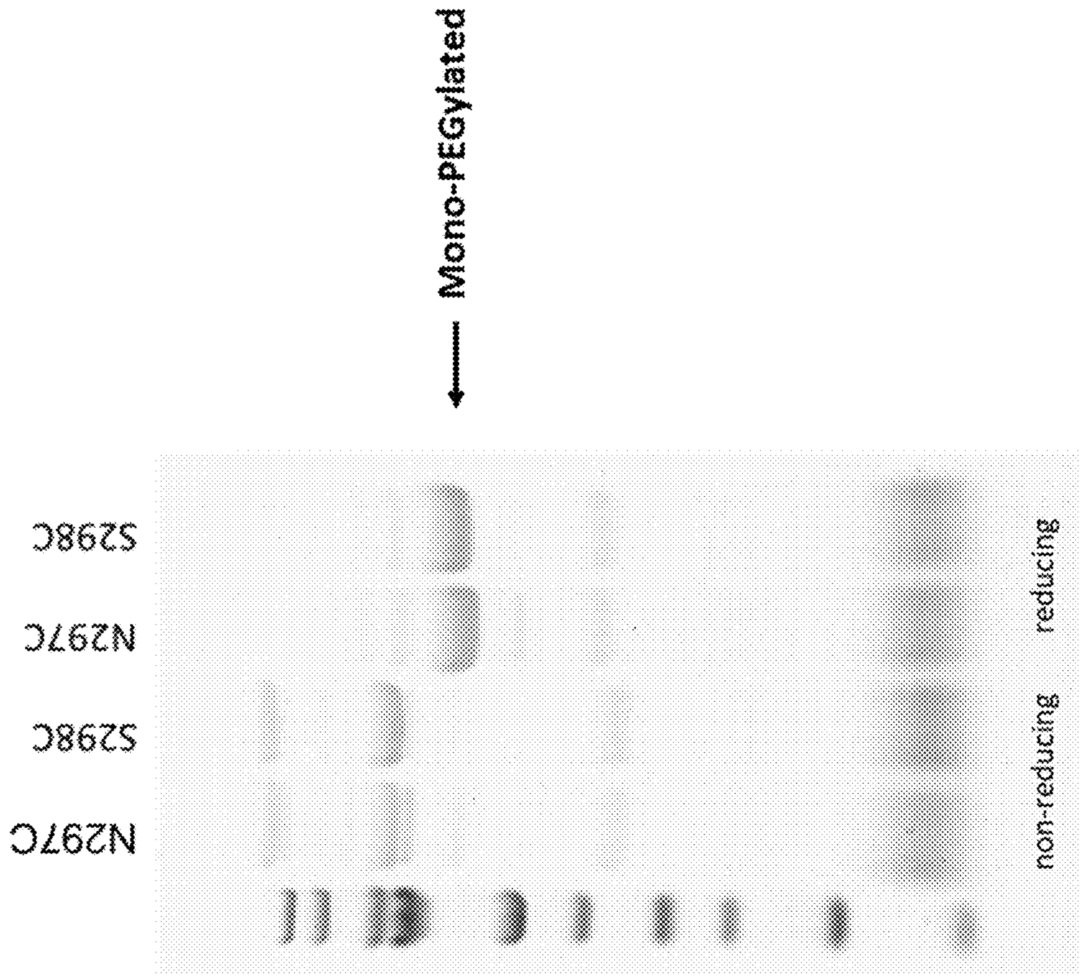

FIG. 23 depicts SDS-PAGE and PEG staining of two single cysteine mutants, N297C and S298C, after PEGylation. 2 single cysteine mutants, N297C and S298C, were PEGylated and analyzed using 4-12% Bis-Tris NuPAGE under non-reducing and reducing conditions. The gel was stained using PEG staining. Significant amounts of half antibody conjugates were detected in the gel under non-reducing condition. PageRuler prestained protein ladder was used as protein molecular weight standards (MW Std).

Figure 24:
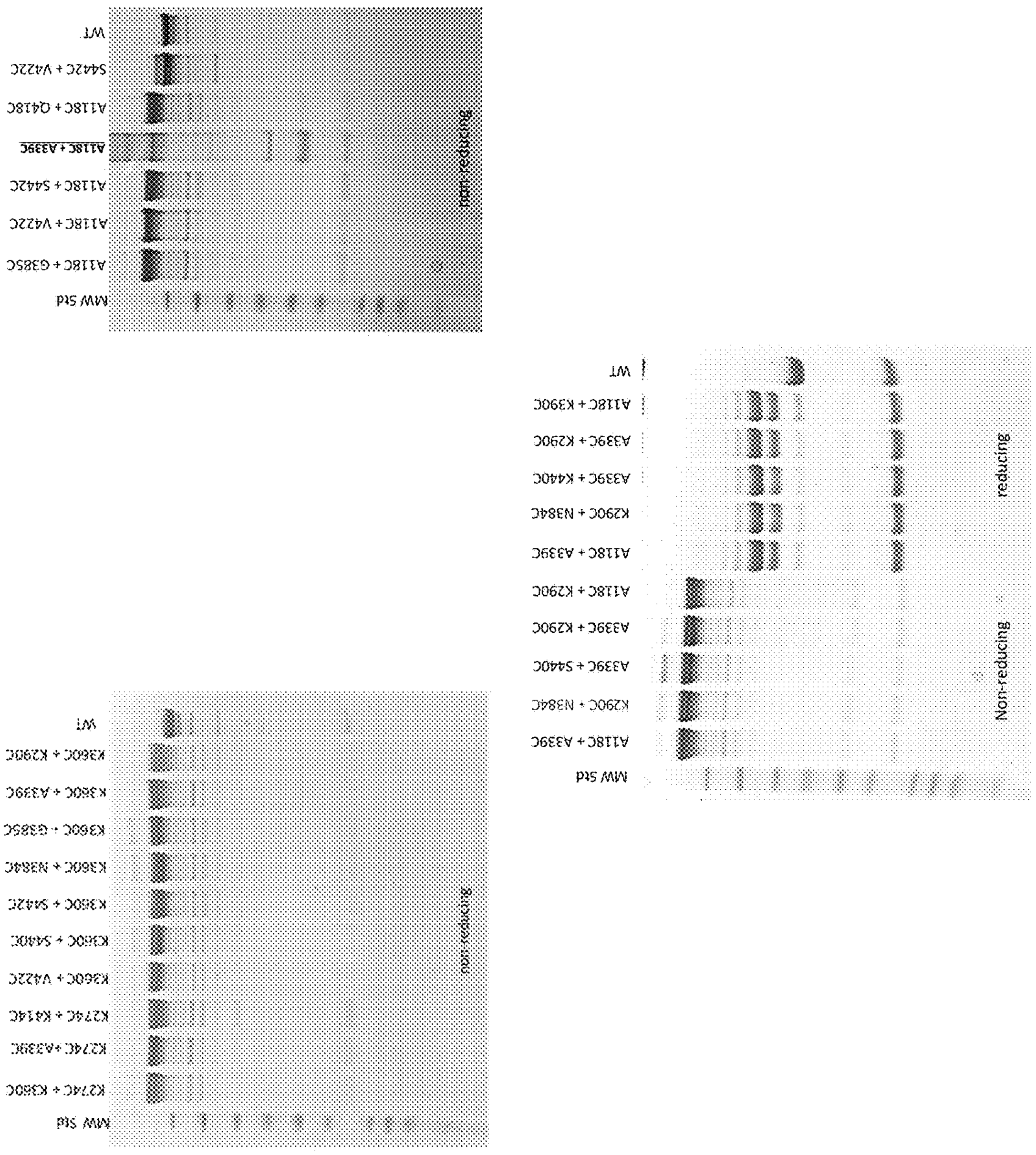

FIG. 24 depicts PEGylation screening of double-engineered antibodies. Double-engineered antibodies (mutants) with a first position cysteine mutation and a second position cysteine mutation were conjugated with PEG and then screened with DTT reductant by loading onto PEG-stained SDS-PAGE with 64 eq DTT for uncapping. Each mutant antibody shown was screened using reducing and non-reducing conditions to determine its PEG to antibody ratio (PAR). One of the mutants, A118C+A339C (highlighted in bold, underlined text), had poor expression and showed diffuse bands after PEGylation. It was re-sequenced and found to have a sequence mismatch. The original mutated clone with correct sequence was re-expressed and PEGylated as shown.

FIG. 25 depicts a heatmap of PEGylated double cysteine mutants. Different colors represent ranges of PAR, mono-&di-PEGylated, multi-PEGylated, and un-PEGylated species. PAR: >3.4 Green<4; >2.5 Yellow<3.3; >0 Red<2.4. Mono-&di-PEGylated: >85% Green<100%; >30% Yellow<84.9%; >5% Red<29.9%. Multi-PEGylated: <10% Green>0%; >10.1% Yellow<20%; >20.1% Red<100%. Un-PEGylated: <6% Green>0%; >6.1% Yellow<10%; >10.1% Red<100%. Selectivity: >0.7 Green<1.0, >051 yellow <0.69, >0 red <0.5.

DETAILED DESCRIPTION

We disclose engineered antibodies that are stable and can be conjugated to a ligand or drug at a ligand/drug to antibody ratio of above 3, making these conjugates suitable for treatment of a variety of indications. Methods of producing these engineered antibodies are also provided.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

As used herein, the term "antigen-binding protein" or "antibody" refers to an immunoglobulin molecule that specifically binds to, or is immunologically reactive with an antigen or epitope, and includes both polyclonal and monoclonal antibodies, as well as functional antibody fragments, including but not limited to fragment antigen-binding (Fab) fragments, $F(ab')_2$ fragments, Fab' fragments, Fv fragments, recombinant IgG (rIgG) fragments, single chain variable fragments (scFv) and single domain antibodies (e.g., sdAb, sdFv, nanobody) fragments. The term "antibody" includes genetically engineered or otherwise modified forms of immunoglobulins, such as intrabodies, peptibodies, chimeric antibodies, fully human antibodies, humanized antibodies, meditope-enabled antibodies, heteroconjugate antibodies (e.g., bispecific antibodies, diabodies, triabodies, tetrabodies, tandem di-scFv, tandem tri-scFv) and the like. Unless otherwise stated, the term "antibody" should be understood to encompass functional antibody fragments thereof.

As used herein, the phrase "parental antigen-binding protein" or "un-engineered antigen-binding protein" refers to an antibody that may be engineered by altering one or more of its amino acid residues to produce a derivative "engineered antigen-binding protein" or "engineered antibody". Such an engineered antigen-binding protein/antibody derived from a parental antigen-binding protein/antibody may be a "single-engineered antigen-binding protein," in which only one amino acid residue is substituted with a different engineered amino acid residue. An engineered antigen-binding protein/antibody derived from a parental antigen-binding protein/antibody may also be a "double-engineered antigen-binding protein," in which an amino acid residue in a first position is substituted with a different engineered amino acid residue and an amino acid residue in a second position is substituted with a different engineered amino acid residue.

As used herein, the phrase "single-engineered parental antigen-binding protein" refers to a parental antigen-binding protein that has been modified with an engineered amino acid residue in a first position, resulting in a single-engineered antigen-binding protein that may be further engineered by altering an amino acid residue in a second position to produce a derivative "double-engineered antigen-binding protein".

As used herein, the phrase "reactive amino acid residue" refers to an amino acid that has a reactive side chain. Reactive amino acid residues include cysteine, lysine, histidine, serine, methionine, tryptophan, tyrosine, aspartate, glutamate, and arginine.

As used herein, the phrase "engineered amino acid residue" refers to an amino acid residue in an antigen-binding protein that has been substituted with a different amino acid residue. As used herein, the phrase "engineered reactive amino acid residue" refers to an amino acid residue in an antigen-binding protein that has been substituted with a different amino acid residue that is a reactive amino acid residue.

As used herein, the term "ligand" is a molecule or atom that is covalently linked to a reactive amino acid residue of an antigen-binding protein either directly or through a linker or through some other reactive moiety. Ligands include, but are not limited to polypeptides, carbohydrates, radionuclides, lipids, nucleic acids, synthetic compounds, and small molecules.

As used herein, the terms "conjugate", "conjugated", and "conjugation" refer to the covalent joining of two or more chemical compounds.

As used herein, the phrase "reactive moiety" or "reactive group" refers to a specific substituent or moiety within a molecule that is responsible for a characteristic chemical reaction of that molecule. The same reactive moiety will undergo the same or similar chemical reaction regardless of the size of the molecule it is a part of.

As used herein, the term "linker" refers to a chemical moiety comprising a covalent bond or a chain of atoms that covalently attaches a polypeptide to a ligand, a drug, a ligand via a ligand, or a drug via a ligand. The linker may be a "cleavable linker" facilitating release of the cytotoxic agent or growth inhibitory agent in the cell. For example, an acid-labile linker, a peptidase-sensitive linker, an esterase labile linker, a photolabile linker or a disulfide-containing linker (See e.g., U.S. Pat. No. 5,208,020) may be used. The linker may be also a "non-cleavable linker" (for example SMCC linker) that might lead to better tolerance in some cases.

As used herein, the phrase "ligand to antibody ratio" or "LAR" refers to the stoichiometric ratio of the number of ligand molecules bound to one antibody. Similarly, the phrase "drug to antibody ratio" or "DAR" refers to the stoichiometric ratio of the number of drug molecules bound to one antibody. The phrase "PEG to antibody ratio" or "PAR" refers to the stoichiometric ratio of the number of PEG molecules bound to one antibody.

As used herein, the phrase "detection probe" refers to a ligand that includes, but is not limited to, a biotin, polyethylene glycol (PEG), fluorescent tag, visualization peptide, and a combination thereof.

As used herein, the term "PEG" or "polyethylene glycol" refers to a polyether compound that has a structure commonly expressed as: $H—(O—CH_2—CH_2)_n—OH$. PEG is also known as polyethylene oxide (PEO) or polyoxyethylene (POE) depending on its molecular weight.

As used herein, the phrase "targeting moiety" refers to a ligand that can act to direct the antibody to which the ligand is conjugated to a particular target. Examples of such targets include, but are not limited to, a cell membrane and a cancer cell.

As used herein, the term "drug" refers to a molecule that causes a change in an organism's physiology or psychology were administered to the organism. Drugs include, but are not limited to: anti-inflammatory, anti-cancer, anti-infective (e.g., antifungal, antibacterial, anti-parasitic, anti-viral, etc.), and anesthetic therapeutic agents. A drug can also be an anti-cancer or cytotoxic agent or a prodrug.

As used herein, the term "prodrug" refers to a precursor or derivative form of a pharmaceutically active agent that is less active, reactive or prone to side effects as compared to the parent drug and is capable of being enzymatically activated or otherwise converted into a more active form in vivo.

As used herein, the phrase "anti-cancer therapeutic agent" or "anti-cancer agent" refers to a molecule which is detrimental to the growth and/or proliferation of neoplastic or tumor or cancer cells and may act to reduce, inhibit or destroy malignancy.

As used herein, the term "cytostatic" refers to a molecule that inhibits cell growth and multiplication.

As used herein, the phrase "cytotoxic nucleoside" refers to a nucleobase or nucleoside analogue that exerts cytotoxic effects by mimicking endogenous nucleosides.

As used herein, the phrase “tubulin binding agent” refers to a molecule that associates directly with the tubulin system.

As used herein, the term “hormone” refers to any member of a class of signaling molecules that are produced by glands in multicellular organisms and that are transported by the circulatory system to target distant organs to regulate physiology and/or behavior. A “hormone antagonist” is a specific type of receptor antagonist which acts upon hormone receptors.

As used herein, the phrase “anti-angiogenesis agent” refers to a molecule that inhibits the physiological process of angiogenesis, through which new blood vessels form from pre-existing vessels.

As used herein, the phrase “enzyme inhibitor” refers to a molecule that inhibits the function of a particular enzyme.

As used herein, the phrase “gene regulator” refers to a molecule that can positively or negatively influence the transcription of a gene.

As used herein, the phrase “monoclonal antibody” refers to an antibody that is made by identical immune cells that are all clones of a unique parent cell. Monoclonal antibodies can have monovalent affinity, in that they bind to the same epitope.

As used herein, the term “library” refers to a defined set of members. If the library references antigen-binding proteins, then the library refers to a defined set of antigen-binding proteins. If the library references amino acid positions, then the library refers to a defined set of positions of amino acids in an antigen-binding protein.

As used herein, the phrase “expression vector” refers to a vehicle by which a DNA or RNA sequence (e.g. a foreign gene) can be introduced into a host cell, so as to transform the host and promote expression (e.g. transcription and translation) of the introduced sequence. Such vectors may comprise regulatory elements, such as a promoter, enhancer, terminator and the like, to cause or direct expression of said polypeptide upon administration to a subject. Examples of promoters and enhancers used in the expression vector for an animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

As used herein, the term “domain” refers to any region of a protein, generally defined on the basis of sequence homologies and often related to a specific structural or functional entity.

As used herein, the phrase “chimeric antibody” refers to an engineered antibody which, in its broadest sense, contains one or more regions from one antibody and one or more regions from one or more other antibodies. In an embodiment, a chimeric antibody comprises a $V_H$ domain and a $V_L$ domain of an antibody derived from a non-human animal, in association with a $C_H$ domain and a $C_L$ domain of another antibody, in an embodiment, a human antibody. As the non-human animal, any animal such as mouse, rat, hamster, rabbit or the like can be used. A chimeric antibody may also denote a multispecific antibody having specificity for at least two different antigens.

As used herein, the phrase “humanized antibody” refers to an antibody which is wholly or partially of non-human origin and which has been modified to replace certain amino acids, for instance in the framework regions of the $V_H$ and $V_L$ domains, in order to avoid or minimize an immune response in humans. The constant domains of a humanized antibody are most of the time human $C_H$ and $C_L$ domains.

As used herein, the term “fragment” refers to a portion or domain of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of a conventional antibody may also be a single domain antibody, such as a heavy chain antibody or VHH.

As used herein, the phrase “cytotoxic therapeutic agent” refers to a substance that inhibits or prevents the function of cells and/or causes destruction of cells. The term “cytotoxic agent” is intended to include chemotherapeutic agents, enzymes, antibiotics, and toxins such as small molecule toxins or enzymatically active toxins of bacterial, fungal, plant or animal origin, including fragments and/or variants thereof, and the various antitumor or anti-cancer agents disclosed below. In some embodiments, the cytotoxic agent is a taxoid, vincas, a maytansinoid or maytansinoid analog such as DM1 or DM4, a small drug, a leptomycin derivative, an auristatin or dolastatin analog, a prodrug, topoisomerase II inhibitors, a DNA alkylating agent, an anti-tubulin agent, a CC-1065 or CC-1065 analog.

As used herein, the phrase “pharmaceutically-acceptable carrier” refers to any and all solvents, dispersion media, coatings, antibacterial and antifungal agents, and the like that are physiologically compatible. Examples of suitable carriers, diluents and/or excipients include one or more of water, amino acids, saline, phosphate buffered saline, buffer phosphate, acetate, citrate, succinate; amino acids and derivates such as histidine, arginine, glycine, proline, glycylglycine; inorganic salts NaCl, calcium chloride; sugars or polyalcohols such as dextrose, glycerol, ethanol, sucrose, trehalose, mannitol; surfactants such as Polysorbate 80, polysorbate 20, poloxamer 188; and the like, as well as combination thereof. In many cases, it will be preferable to include isotonic agents, such as sugars, polyalcohols, or sodium chloride in the composition, and formulation may also contain an antioxidant such as tryptamine and a stabilizing agent such as Tween 20.

As used herein, the term “treating” refers to reversing, alleviating, inhibiting the progress of, or preventing a disease, disorder, or condition, or one or more symptoms of such disease, disorder, or condition. For example, treating cancer means the inhibition of the growth of malignant cells of a tumor and/or the progression of metastases from said tumor. Such treatment can also lead to the regression of tumor growth, i.e., the decrease in size of a measurable tumor. In particular, such treatment leads to the complete regression of the tumor or metastasis.

A. Antigen-Binding Proteins or Antibodies

As will be discussed in more detail below, the generic phrase “antigen-binding protein” or “antibody” comprises five distinct classes of antibody that can be distinguished biochemically. While all five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a “Y” configuration wherein the light chains bracket the heavy chains starting at the mouth of the “Y” and continuing through the variable region.

Light chains of immunoglobulin are classified as either kappa or lambda (κ, λ).

Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin isotype subclasses (e.g., IgG1, IgG2, IgG3, IgG4, IgA1, etc.) are well characterized and are known to confer functional specialization. Modified versions of each of these classes and isotypes are readily discernable to the skilled artisan in view of the instant disclosure and, accordingly, are within the scope of the current disclosure.

Both the light and heavy chains are divided into regions of structural and functional homology. The term "region" refers to a part or portion of an immunoglobulin or antibody chain and includes constant region or variable regions, as well as more discrete parts or portions of said regions. For example, light chain variable regions include "complementarity determining regions" or "CDRs" interspersed among "framework regions" or "FRs", as defined herein.

The regions of an immunoglobulin heavy or light chain may be defined as "constant" (C) region or "variable" (V) regions, based on the relative lack of sequence variation within the regions of various class members in the case of a "constant region", or the significant variation within the regions of various class members in the case of a "variable regions". The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, transplacental mobility, Fc receptor binding, complement binding, and the like. The subunit structures and three-dimensional configurations of the constant regions of the various immunoglobulin classes are well known.

The constant and variable regions of immunoglobulin heavy and light chains are folded into domains. The term "domain" refers to a globular region of a heavy or light chain comprising peptide loops (e.g., comprising 3 to 4 peptide loops) stabilized, for example, by β-pleated sheet and/or intrachain disulfide bond. Constant region domains on the light chain of an immunoglobulin are referred to interchangeably as "light chain constant region domains", "$C_L$ regions" or "$C_L$ domains". Constant domains on the heavy chain (e.g. hinge, $C_H1$, $C_H2$ or $C_H3$ domains) are referred to interchangeably as "heavy chain constant region domains", "$C_H$" region domains or "$C_H$ domains". Variable domains on the light chain are referred to interchangeably as "light chain variable region domains", "$V_L$ region domains" or "$V_L$ domains".

Variable domains on the heavy chain are referred to interchangeably as "heavy chain variable region domains", "$V_H$ region domains" or "$V_H$ domains".

By convention the numbering of the variable constant region domains increases as they become more distal from the antigen binding site or amino-terminus of the immunoglobulin or antibody. The N-terminus of each heavy and light immunoglobulin chain is a variable region and at the C-terminus is a constant region; the $C_H3$ and $C_L$ domains actually comprise the carboxy-terminus of the heavy and light chain, respectively. Accordingly, the domains of a light chain immunoglobulin are arranged in a $V_L$-$C_L$ orientation, while the domains of the heavy chain are arranged in the $V_H$-CH1-hinge-$C_H2$-$C_H3$ orientation.

Amino acid positions in a heavy chain constant region, including amino acid positions in the CH1, hinge, $C_H2$, $C_H3$, and $C_L$ domains, may be numbered according to the Kabat index numbering system (see Kabat et al, in "Sequences of Proteins of Immunological Interest", U.S. Dept. Health and Human Services, 5th edition, 1991). Alternatively, antibody amino acid positions may be numbered according to the EU index numbering system (see Kabat et al, ibid). As used herein, the term "$V_H$ domain" includes the amino terminal variable domain of an immunoglobulin heavy chain, and the term "$V_L$ domain" includes the amino terminal variable domain of an immunoglobulin light chain.

As used herein, the term "$C_H1$ domain" includes the first (most amino terminal) constant region domain of an immunoglobulin heavy chain that extends, e.g., from about positions 114-223 in the Kabat numbering system (EU positions 118-215). The $C_H1$ domain is adjacent to the $V_H$ domain and amino terminal to the hinge region of an immunoglobulin heavy chain molecule, and does not form a part of the Fc region of an immunoglobulin heavy chain.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "$C_H2$ domain" includes the portion of a heavy chain immunoglobulin molecule that extends, e.g., from about positions 244-360 in the Kabat numbering system (EU positions 231-340). The $C_H2$ domain is unique in that it is not closely paired with another domain. Rather, two N-linked branched carbohydrate chains are interposed between the two $C_H2$ domains of an intact native IgG molecule. In one embodiment, an antigen-binding protein of the current disclosure comprises a $C_H2$ domain derived from an IgG1 molecule (e.g. a human IgG1 molecule).

As used herein, the term "$C_H3$ domain" includes the portion of a heavy chain immunoglobulin molecule that extends approximately 110 residues from N-terminus of the $C_H2$ domain, e.g., from about positions 361-476 of the Kabat numbering system (EU positions 341-445). The $C_H3$ domain typically forms the C-terminal portion of the antibody. In some immunoglobulins, however, additional domains may extend from $C_H3$ domain to form the C-terminal portion of the molecule (e.g. the $C_H4$ domain in the chain of IgM and the e chain of IgE). In one embodiment, an antigen-binding protein of the current disclosure comprises a $C_H3$ domain derived from an IgG1 molecule (e.g. a human IgG1 molecule). As used herein, the term "$C_L$ domain" includes the constant region domain of an immunoglobulin light chain that extends, e.g. from about Kabat position 107A-216. The $C_L$ domain is adjacent to the $V_L$ domain. In one embodiment, an antigen-binding protein of the current disclosure comprises a $C_L$ domain derived from a kappa light chain (e.g., a human kappa light chain).

As used herein, the term "Fc region" is defined as the portion of a heavy chain constant region beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a $C_H2$ domain, and a $C_H3$ domain.

The term "native Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc can be of human origin and can be any of the immunoglobulins, such as IgG1 or IgG2.

Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc" as used herein is generic to the monomeric, dimeric, and multimeric forms.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like antigen-binding proteins. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

As indicated above, the variable regions of an antibody allow it to selectively recognize and specifically bind epitopes on antigens. That is, the $V_L$ domain and $V_H$ domain of an antibody combine to form the variable region (Fv) that defines a three-dimensional antigen binding site. This quaternary antibody structure forms the antigen binding site present at the end of each arm of the Y. More specifically, the antigen binding site is defined by three complementary determining regions (CDRs) on each of the heavy and light chain variable regions. As used herein, the term "antigen binding site" includes a site that specifically binds (immunoreacts with) an antigen (e.g., a cell surface or soluble antigen). The antigen binding site includes an immunoglobulin heavy chain and light chain variable region and the binding site formed by these variable regions determines the specificity of the antibody. An antigen binding site is formed by variable regions that vary from one antibody to another. The altered antibodies of the current disclosure comprise at least one antigen binding site.

In certain embodiments, antigen-binding proteins of the current disclosure comprise at least two antigen binding domains that provide for the association of the antigen-binding protein with the selected antigen. The antigen binding domains need not be derived from the same immunoglobulin molecule. In this regard, the variable region may or be derived from any type of animal that can be induced to mount a humoral response and generate immunoglobulins against the desired antigen. As such, the variable region of the antigen-binding protein may be, for example, of mammalian origin e.g., may be human, murine, rat, goat, sheep, non-human primate (such as cynomolgus monkeys, macaques, etc.), lupine, or camelid (e.g., from camels, llamas and related species). In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the 3-sheet structure. Thus, these framework regions act to form a scaffold that provides for positioning the six CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to the immunoreactive antigen epitope.

Exemplary antigen-binding proteins include antibody variants. As used herein, the term "antibody variant" includes synthetic and engineered forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. In addition, the term "antibody variant" includes multivalent forms of antibodies (e.g., trivalent, tetravalent, etc., antibodies that bind to three, four or more copies of the same antigen.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject antigen-binding proteins typically have at least one binding site specific for a human antigen molecule.

The term "specificity" refers to the ability to specifically bind (e.g., immunoreact with) a given target antigen (e.g., a human target antigen). A antigen-binding protein may be monospecific and contain one or more binding sites which specifically bind a target or a polypeptide may be multispecific and contain two or more binding sites which specifically bind the same or different targets. In certain embodiments, an antigen-binding protein is specific for two different (e.g., non-overlapping) portions of the same target. In certain embodiments, the antigen-binding protein is specific for more than one target. Exemplary antigen-binding proteins (e.g., antibodies) which comprise antigen binding sites that bind to antigens expressed on tumor cells are known in the art and one or more CDRs from such antibodies can be included in an antibody as described herein.

Occasionally, residues from nonhypervariable or framework regions (FR) influence the overall domain structure and hence the combining site. Complementarity Determining Regions or CDRs therefore refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

A.1. Methods of Producing Antibodies

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or immunoglobulin chains, by standard techniques for production of polypeptides. For instance, they can be synthesized using well-known solid phase method using a commercially available peptide synthesis apparatus (such as that made by Applied Biosystems, Foster City, Calif) and following the manufacturer's instructions. Alternatively, antibodies and immunoglobulin chains of the invention can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

The invention further relates to a method of producing an antibody of the invention, which method comprises the steps consisting of: (i) culturing a transformed host cell according to the invention; (ii) expressing said antibody or polypeptide; and (iii) recovering the expressed antibody or polypeptide. Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

A humanized chimeric antibody of the present invention can be produced by obtaining nucleic sequences encoding humanized $V_L$ and $V_H$ domains as previously described, constructing a human chimeric antibody expression vector by inserting them into an expression vector for animal cell having genes encoding human antibody $C_H$ and human antibody $C_L$, and expressing the coding sequence by introducing the expression vector into an animal cell. As the $C_H$ domain of a human chimeric antibody, it may be any region which belongs to human immunoglobulin heavy chains, but those of IgG class are suitable and any one of subclasses belonging to IgG class, such as IgG1, IgG2, IgG3 and IgG4, can also be used. Also, as the $C_L$ of a human chimeric antibody, it may be any region which belongs to human immunoglobulin light chains, and those of kappa class or lambda class can be used.

Methods for producing humanized or chimeric antibodies involve conventional recombinant DNA and gene transfection techniques that are well known in the art (See Morrison S L. et al. (1984) and patent documents U.S. Pat. Nos. 5,202,238; and 5,204,244). Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, the technique disclosed in the application WO2009/032661, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Numerous methods for humanization of an antibody sequence are known in the art; see e.g. the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues. Another alternative technique is known as "guided selection" (Jespers et al. (1994) Biotechnology 12, 899) and can be used to derive from a murine antibody a fully human antibody conserving the epitope and binding characteristics of the parental antibody.

For chimeric antibodies, humanization typically involves modification of the framework regions of the variable region sequences. Amino acid residues that are part of a CDR will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, for instance by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, for instance Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. In an embodiment the YB2/0 cell is used, since ADCC activity of chimeric or humanized antibodies is enhanced when expressed in this cell.

A.2. Modified Antibodies

Modifications and changes may be made in the structure of the antibodies of the present invention, and in the DNA sequences encoding them, and still result in a functional antibody or polypeptide with desirable characteristics. In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate −3.5); asparagine (−3.5); lysine (−3.9); and arginine (−4.5).

A further object of the present invention also encompasses function-conservative variants of the polypeptides of the present invention. For example, certain amino acids may be substituted by other amino acids in a protein structure without appreciable loss of activity. Since the interactive capacity and nature of a protein define its biological functional activity, certain amino acid substitutions can be made in a protein sequence, and of course in its DNA encoding sequence, while nevertheless obtaining a protein with like properties. It is thus contemplated that various changes may be made in the antibody sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein. It is also possible to use well-established technologies, such as alanine-scanning approaches, to identify, in an antibody or polypeptide of the invention, all the amino acids that can be substituted without significant loss of binding to the antigen. Such residues can be qualified as neutral, since they are not involved in antigen binding or in maintaining the structure of the antibody. One or more of these neutral positions can be substituted by alanine or by another amino acid can without changing the main characteristics of the antibody or polypeptide of the invention.

As outlined above, amino acid substitutions are generally therefore based on the relative similarity of the amino acid side-chain substituents, for example, their hydrophobicity, hydrophilicity, charge, size, and the like. Exemplary substitutions which take any of the foregoing characteristics into consideration are well known to those of skill in the art and include: arginine and lysine; glutamate and aspartate; serine and threonine; glutamine and asparagine; and valine, leucine and isoleucine.

A.2.a. Fc Modifications

In certain embodiments, antigen-binding proteins may include an antibody constant region (e.g. an IgG constant region e.g., a human IgG constant region, e.g., a human IgG1 or IgG4 constant region) which mediates one or more effector functions. For example, binding of the Cl-complex to an antibody constant region may activate the complement system. Activation of the complement system is important in the opsonization and lysis of cell pathogens. The activation of the complement system also stimulates the inflammatory response and may also be involved in autoimmune hypersensitivity. Further, antibodies bind to receptors on various cells via the Fc region (Fc receptor binding sites on the antibody Fc region bind to Fc receptors (FcRs) on a cell). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In some embodiments, the antigen-binding proteins (e.g., antibodies or antigen binding fragments thereof) featured in the invention bind to an Fc-gamma receptor. In alternative embodiments, antigen-binding proteins may include a constant region which is devoid of one or more effector functions (e.g., ADCC activity) and/or is unable to bind Fc gamma receptors for IgG.

Certain embodiments include antibodies in which at least one amino acid in one or more of the constant region domains (in addition to the modifications featured in the invention) has been deleted or otherwise altered so as to provide additional desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity, or when compared to an antibody containing only the modifications featured in the invention. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain other embodiments, antigen-binding proteins comprise constant regions derived from different antibody isotypes (e.g., constant regions from two or more of a human IgG1, IgG2, IgG3, or IgG4). In other embodiments, antigen-binding proteins comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, antigen-binding proteins comprise an Fc region or portion thereof from a human IgG4 molecule and a Ser228Pro mutation (EU numbering) in the core hinge region of the molecule.

In certain embodiments, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases, it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well know immunological techniques without undue experimentation.

An Fc domain employed in an antibody featured in the invention is an Fc variant. As used herein, the term “Fc variant” refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant in addition to the variants featured in the invention, may be located at any position (i.e., any EU convention amino acid position) within the Fc domain. In one embodiment, the Fc variant comprises an additional substitution at an amino acid position located in a hinge domain or portion thereof. In another embodiment, the Fc variant comprises an additional substitution at an amino acid position located in a $C_H2$ domain or portion thereof. In another embodiment, the Fc variant comprises an additional substitution at an amino acid position located in a $C_H3$ domain or portion thereof. In another embodiment, the Fc variant comprises an additional substitution at an amino acid position located in a $C_H4$ domain or portion thereof.

The antigen-binding proteins may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455 A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated in its entirety by reference herein. In one exemplary embodiment, an antigen-binding protein may comprise an Fc variant comprising an amino acid substitution at EU position 268 (e.g., H268D or H268E). In another exemplary embodiment, an antigen-binding protein may include an amino acid substitution at EU position 239 (e.g., S239D or S239E) and/or EU position 332 (e.g., I332D or I332Q).

In certain embodiments, an antigen-binding protein may include an Fc variant comprising an amino acid substitution which alters the antigen-independent effector functions of the antibody, in particular the circulating half-life of the antigen-binding protein. Such antigen-binding proteins exhibit either increased or decreased binding to FcRn when compared to antigen-binding proteins lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include applications localized to the brain, kidney, and/or liver. In one exemplary embodiment, the altered antigen-binding proteins (e.g., antibodies or antigen binding fragments thereof) exhibit reduced transport across the epithelium of kidney glomeruli from the vasculature. In another embodiment, the altered antigen-binding proteins (e.g., antibodies or antigen binding fragments thereof) exhibit reduced transport across the blood brain barrier (BBB) from the brain into the vascular space. In one embodiment, an antibody with altered FcRn binding comprises an Fc domain having one or more amino acid substitutions within the “FcRn binding loop” of an Fc domain. The FcRn binding loop is comprised of amino acid residues 280-299 (according to EU numbering).

Exemplary amino acid substitutions which alter FcRn binding activity are disclosed in International PCT Publication No. WO05/047327 which is incorporated in its entirety by reference herein. In certain exemplary embodiments, the antigen-binding proteins (e.g., antibodies or antigen binding fragments thereof) include an Fc domain having one or more of the following substitutions: V284E, H285E, N286D, K290E and S304D (EU numbering). In yet other exemplary embodiments, the binding molecules include a human Fc domain with the double mutation H433K/N434F (see, e.g., U.S. Pat. No. 8,163,881). In other embodiments, antigen-binding proteins, for use in the diagnostic and treatment methods described herein have a constant region, e.g., an IgG1 or IgG4 heavy chain constant region, which is altered to reduce or eliminate glycosylation. For example, antigen-binding proteins (e.g., antibodies or antigen binding fragments thereof) may also include an Fc variant comprising an amino acid substitution which alters the glycosylation of the antibody Fc. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Double-Cysteine Engineered Fc-Containing Binding Polypeptides

In one aspect, the present disclosure provides an isolated Fc domain variant comprising or complexed with (e.g., fused to) at least one binding domain (e.g., at least one binding polypeptide).

In certain embodiments, the Fc domain variant comprises an antibody heavy chain constant ($C_H$) domain comprising an engineered reactive amino acid residue at a first position and an engineered reactive amino acid residue at a second position; wherein, according to the numbering of the EU index of Kabat, the first position is position 274 and the second position is selected from the group consisting of: 339, 360, 384, 385, 422, 440, and any combination thereof.

In certain embodiments, the Fc domain variant comprises an antibody heavy chain constant ($C_H$) domain comprising an engineered reactive amino acid residue at a first position and an engineered reactive amino acid residue at a second position; wherein, according to the numbering of the EU index of Kabat, the first position is position 339 and the second position is selected from the group consisting of: 290, 360, 384, 385, 422, 440, and any combination thereof.

In certain embodiments, the Fc domain variant comprises an antibody heavy chain constant ($C_H$) domain comprising an engineered reactive amino acid residue at a first position and an engineered reactive amino acid residue at a second position; wherein, according to the numbering of the EU index of Kabat, the first position is position 384 and the second position is selected from the group consisting of: 274, 290, 339, and any combination thereof.

In certain embodiments, the Fc domain variant further comprises a $C_H1$ domain comprising an engineered reactive amino acid residue at the second position of 118 in the $C_H1$ domain, according to the numbering of the EU index of Kabat.

In certain embodiments, the Fc domain variant further comprises a $C_H1$ domain, comprising an engineered reactive amino acid residue at a first position of 118 in the $C_H1$ domain, according to the numbering of the EU index of Kabat, and an engineered reactive amino acid residue at a second position selected from the group consisting of: 274, 339, 384, 385, 422, 440, and any combination thereof, according to the numbering of the EU index of Kabat.

In certain embodiments, the engineered reactive amino acid residue is selected from the group consisting of: cysteine, lysine, histidine, serine, methionine, tryptophan, tyrosine, aspartate, glutamate, and arginine. In certain embodiments, the engineered reactive amino acid residue is cysteine.

In certain embodiments, the binding domain comprises one or more antigen binding domains. The antigen binding domains need not be derived from the same molecule as the parental Fc domain (i.e., an Fc domain that does not comprise a first and second engineered reactive amino acid residue). In certain embodiments, the Fc domain variant is present in an antibody.

In one embodiment, an Fc domain variant is present in an antibody or is complexed with an antibody. Any antibody from any source or species can be employed with an Fc domain variant disclosed herein. Suitable antibodies include without limitation, chimeric antibodies, humanized antibodies, or human antibodies. Suitable antibodies include without limitation, full-length antibodies, monoclonal antibodies, polyclonal antibodies, or single-domain antibodies, such as VHH antibodies.

In certain exemplary embodiments, an Fc domain variant may be bound to or complexed with an antigen-binding fragment of an antibody. The term "antigen-binding fragment" refers to a polypeptide fragment of an immunoglobulin or antibody which binds antigen or competes with intact antibody (i.e., with the intact antibody from which they were derived) for antigen binding (i.e., specific binding). Antigen-binding fragments can be produced by recombinant or biochemical methods that are well known in the art. Exemplary antigen-binding fragments include Fv, Fab, Fab', and (Fab')2. In certain exemplary embodiments, a binding polypeptide of the current disclosure comprises an antigen-binding fragment and an Fc domain variant.

In some embodiments, the binding polypeptide comprises a single chain variable region sequence (ScFv). Single chain variable region sequences comprise a single polypeptide having one or more antigen binding sites, e.g., a $V_L$ domain linked by a flexible linker to a VH domain. ScFv molecules can be constructed in a VH-linker-$V_L$ orientation or $V_L$-linker-VH orientation. The flexible hinge that links the $V_L$ and VH domains that make up the antigen binding site includes from about 10 to about 50 amino acid residues. Connecting peptides are known in the art. Binding polypeptides may comprise at least one scFv and/or at least one constant region. In one embodiment, a binding polypeptide of the current disclosure may comprise at least one scFv linked or fused to an Fc domain variant.

In some embodiments, a binding polypeptide of the current disclosure is a multivalent (e.g., tetravalent) antibody which is produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to an Fc domain variant via a flexible linker (e.g., a gly/ser linker). In another embodiment a tetravalent antibody of the current disclosure can be made by fusing an ScFv molecule to a connecting peptide, which is fused to an Fc domain variant to construct an ScFv-Fab tetravalent molecule.

In another embodiment, a binding polypeptide of the current disclosure is an altered minibody. An altered minibody of the current disclosure is a dimeric molecule made up of two polypeptide chains each comprising an ScFv molecule which is fused to an Fc domain variant via a connecting peptide. Minibodies can be made by constructing an ScFv component and connecting peptide components using methods described in the art (see, e.g., U.S. Pat. No. 5,837,821 or WO 94/09817A1). In another embodiment, a tetravalent minibody can be constructed. Tetravalent minibodies can be constructed in the same manner as minibodies, except that two ScFv molecules are linked using a flexible linker. The linked scFv-scFv construct is then joined to an Fc domain variant.

In another embodiment, a binding polypeptide of the current disclosure comprises a diabody. Diabodies are dimeric, tetravalent molecules each having a polypeptide similar to scFv molecules, but usually having a short (less than 10, e.g., about 1 to about 5) amino acid residue linker connecting both variable domains, such that the $V_L$ and VH domains on the same polypeptide chain cannot interact. Instead, the $V_L$ and VH domain of one polypeptide chain interact with the VH and $V_L$ domain (respectively) on a second polypeptide chain (see, for example, WO 02/02781). Diabodies of the current disclosure comprise an scFv-like molecule fused to an Fc domain variant.

In other embodiments, binding polypeptides comprise multi-specific or multivalent antibodies comprising one or more variable domain in series on the same polypeptide chain, e.g., tandem variable domain (TVD) polypeptides. Exemplary TVD polypeptides include the "double head" or "Dual-Fv" configuration described in U.S. Pat. No. 5,989,830. In the Dual-Fv configuration, the variable domains of two different antibodies are expressed in a tandem orientation on two separate chains (one heavy chain and one light chain), wherein one polypeptide chain has two VH domains in series separated by a peptide linker (VH1-linker-VH2) and the other polypeptide chain consists of complementary $V_L$ domains connected in series by a peptide linker ($V_L$1-linker-$V_L$2). In the cross-over double head configuration, the variable domains of two different antibodies are expressed in a tandem orientation on two separate polypeptide chains (one heavy chain and one light chain), wherein one polypeptide chain has two VH domains in series separated by a peptide linker (VH1-linker-VH2) and the other polypeptide chain consists of complementary $V_L$ domains connected in series by a peptide linker in the opposite orientation ($V_L$2-linker-$V_L$1). Additional antibody variants based on the "Dual-Fv" format include the Dual-Variable-Domain IgG (DVD-IgG) bispecific antibody (see U.S. Pat. No. 7,612,181 and the TBT1 format (see US 2010/0226923 A1). In some embodiments, binding polypeptides comprise multi-specific or multivalent antibodies comprising one or more variable domain in series on the same polypeptide chain fused to an Fc domain variant.

In another embodiment, a binding polypeptide comprises a cross-over dual variable domain IgG (CODV-IgG) bispecific antibody based on a "double head" configuration (see US20120251541 A1, which is incorporated by reference herein in its entirety).

In other embodiments, a binding polypeptide comprises a CrossMab or a CrossMab-Fab multispecific format (see WO2009080253 and Schaefer, et al., PNAS (2011), 108: 11187-1191). Antibody variants based on the CrossMab format have a crossover of antibody domains within one arm of a bispecific IgG antibody enabling correct chain association.

In other embodiments, the glycosylated effector-competent polypeptide comprises a multispecific antibody in a T cell engager format. A "T cell engager" refers to binding proteins directed to a host's immune system, more specifically the T cells' cytotoxic activity as well as directed to a tumor target protein. In some embodiments, the isolated effector-competent polypeptide comprises a multispecific antibody in an NK cell engager format. An "NK cell engager" refers to binding proteins comprising monoclonal antibody fragments targeting activating NK cell receptors, antigen-specific targeting regions, and an Fc region (Gauthier, et al. Cell (2019), 177: 1701-13).

A binding polypeptide of the present disclosure, comprising an Fc domain variant described herein, can include the CDR sequences or the variable domain sequences of a known "parent" antibody. In some embodiments, the parent antibody and the antibody of the disclosure can share similar or identical sequences except for modifications to the Fc domain as disclosed herein.

B. Antibody-Ligand Conjugates

Antibody-ligand conjugates can be used for a wide range of applications, including for targeted therapeutics. In target-specific treatments, the antigen-binding portion of the antibody can be directed to a target treatment site to then deliver a ligand-conjugated to the antibody to that site. This ligand can be a drug, such as a biologically active cytotoxic payload. The advantage of using antibody-ligand-conjugated molecules is that they can be designed to discriminate between healthy and diseased tissue. Indeed, such molecules have shown an improved therapeutic index, i.e., higher efficacy and/or lower toxicity profiles than un-targeted antibodies in a clinical setting.

Conventional methods of attaching a ligand to an antibody utilize covalently linking the ligand to reactive amino acids, such as lysine, that already exist on the antibody. As a result, a heterogeneous mixture of antibodies is generated, where the ligand is attached at a number of sites on the antibody. Depending on reaction conditions, the heterogeneous mixture can contain a distribution of antibodies with from 0 to 10, or more, attached ligands. Analytical and preparative methods are inadequate to separate these different antibody-ligand conjugates, resulting in a mixture that is not uniform or well-defined and therefore not predictable in treatment regimens.

Antibodies are large, complex and structurally diverse biomolecules, often with many reactive groups. Their reactivities with linker reagents and ligand-linker intermediates are dependent on factors such as ligand concentration, pH, salt concentration, and the identity of co-solvents. Furthermore, a multi-step conjugation process to existing reactive groups on the antibody may be non-reproducible due to difficulties in controlling the reaction conditions and characterizing reactants and intermediates.

B.1. Antibodies with Ligands Conjugated to Engineered Reactive Amino Acid Residues The introduction of engineered reactive amino acid residues on the surface of antibodies, where the residues are available for conjugation to a ligand but do not perturb antibody folding and assembly or alter antigen binding and effector functions, results in engineered antigen-binding proteins or engineered antibodies, which can be used to prepare defined antibody-ligand conjugate populations.

In certain embodiments of the invention disclosed herein, an engineered amino acid residue is an amino acid residue in an antigen-binding protein that has been substituted with a different amino acid residue. In certain embodiments, an engineered reactive amino acid residue is an amino acid residue in an antigen-binding protein that has been substituted with a different amino acid residue that is a reactive amino acid residue. In certain embodiments, the engineered reactive amino acid residue is cysteine, lysine, histidine, serine, methionine, tryptophan, tyrosine, aspartate, glutamate, or arginine. In certain embodiments, the engineered reactive amino acid residue is lysine. In certain embodiments, the engineered reactive amino acid residue is cysteine.

In certain embodiments of the invention disclosed herein, a parental antigen-binding protein is engineered by altering one or more of its amino acid residues to produce a derivative engineered antigen-binding protein or engineered antibody. Such an engineered antigen-binding protein/antibody derived from a parental antigen-binding protein/antibody may be a single-engineered antigen-binding protein, in which only one amino acid residue is substituted with a different engineered amino acid residue. An engineered antigen-binding protein/antibody derived from a parental antigen-binding protein/antibody may also be a double-engineered antigen-binding protein, in which an amino acid residue in a first position is substituted with a different engineered amino acid residue and an amino acid residue in a second position is substituted with a different engineered amino acid residue.

In certain embodiments, a single-engineered parental antigen-binding protein is an antigen-binding protein that has an engineered amino acid residue in a first position and may be further engineered by altering an amino acid residue in a second position to produce a derivative double-engineered antigen-binding protein.

In certain embodiments, an engineered antigen-binding protein is produced, where an engineered reactive amino acid residue is introduced into between one and five positions in the antigen-binding protein. In certain embodiments, an engineered antigen-binding protein is produced, where an engineered reactive amino acid residue is introduced into a first position in the antigen-binding protein, resulting in a single-engineered antigen-binding protein. In certain embodiments, an engineered antigen-binding protein is produced, where an engineered reactive amino acid residue is introduced into a first position and an engineered reactive amino acid residue is introduced into a second position in the antigen-binding protein, resulting in a double-engineered antigen-binding protein. In certain embodiments, the engineered reactive amino acid is lysine. In certain embodiments, the engineered reactive amino acid is cysteine.

In one aspect of the double-engineered antigen-binding protein or fragment thereof disclosed herein, the double-engineered antigen-binding protein or fragment thereof comprises an antibody heavy chain constant ($C_H$) domain comprising an engineered reactive amino acid residue at a first position and an engineered reactive amino acid residue at a second position; wherein, according to the numbering of the EU index of Kabat, the first position is position 274 and the second position is selected from the group consisting of: 339, 360, 384, 385, 422, 440, and any combination thereof. In certain embodiments, the engineered reactive amino acid residue is cysteine, lysine, histidine, serine, methionine, tryptophan, tyrosine, aspartate, glutamate, or arginine. In certain embodiments, the engineered reactive amino acid residue is lysine. In certain embodiments, the engineered reactive amino acid residue is cysteine.

In another aspect of the double-engineered antigen-binding protein or fragment thereof disclosed herein, the double-engineered antigen-binding protein or fragment thereof comprises an antibody heavy chain constant ($C_H$) domain comprising an engineered reactive amino acid residue at a first position and an engineered reactive amino acid residue at a second position; wherein, according to the numbering of the EU index of Kabat, the first position is position 339 and the second position is selected from the group consisting of: 290, 360, 384, 385, 422, 440, and any combination thereof. In certain embodiments, the engineered reactive amino acid residue is cysteine, lysine, histidine, serine, methionine, tryptophan, tyrosine, aspartate, glutamate, or arginine. In certain embodiments, the engineered reactive amino acid residue is lysine. In certain embodiments, the engineered reactive amino acid residue is cysteine.

In another aspect of the double-engineered antigen-binding protein or fragment thereof disclosed herein, the double-engineered antigen-binding protein or fragment thereof comprises an antibody heavy chain constant ($C_H$) domain comprising an engineered reactive amino acid residue at a first position and an engineered reactive amino acid residue at a second position; wherein, according to the numbering of the EU index of Kabat, the first position is position 118 and the second position is selected from the group consisting of: 274, 339, 384, 385, 422, 440, and any combination thereof. In certain embodiments, the engineered reactive amino acid residue is cysteine, lysine, histidine, serine, methionine, tryptophan, tyrosine, aspartate, glutamate, or arginine. In certain embodiments, the engineered reactive amino acid residue is lysine. In certain embodiments, the engineered reactive amino acid residue is cysteine.

In another aspect of the double-engineered antigen-binding protein or fragment thereof disclosed herein, the double-engineered antigen-binding protein or fragment thereof comprises an antibody heavy chain constant ($C_H$) domain comprising an engineered reactive amino acid residue at a first position and an engineered reactive amino acid residue at a second position; wherein, according to the numbering of the EU index of Kabat, the first position is position 384 and the second position is selected from the group consisting of: 118, 274, 290, 339, and any combination thereof. In certain embodiments, the engineered reactive amino acid residue is cysteine, lysine, histidine, serine, methionine, tryptophan, tyrosine, aspartate, glutamate, or arginine. In certain embodiments, the engineered reactive amino acid residue is lysine. In certain embodiments, the engineered reactive amino acid residue is cysteine.

In certain embodiments, the double-engineered antigen-binding protein or fragment thereof disclosed herein comprises an engineered reactive amino acid residue that is conjugated to a ligand via a reactive moiety. In certain embodiments, the engineered reactive amino acid residue is conjugated to the ligand by a linker. In certain embodiments, the linker is cleavable. In certain embodiments, the linker is non-cleavable. In certain embodiments, the ligand to antibody ratio (LAR) is at least 3.0. In certain embodiments, the LAR is at least 3.1. In certain embodiments, the LAR is at least 3.2. In certain embodiments, the LAR is at least 3.3. In certain embodiments, the LAR is at least 3.4. In certain embodiments, the ligand is PEG and the PEG to antibody ratio (PAR) is at least 3.0. In certain embodiments, the PAR is at least 3.1. In certain embodiments, the PAR is at least 3.2. In certain embodiments, the PAR is at least 3.3. In certain embodiments, the PAR is at least 3.4. In certain embodiments, the ligand is a drug and the drug to antibody ratio (DAR) is at least 3.0. In certain embodiments, the DAR is at least 3.1. In certain embodiments, the DAR is at least 3.2. In certain embodiments, the DAR is at least 3.3. In certain embodiments, the DAR is at least 3.4.

In certain embodiments, the single-engineered antigen-binding protein or fragment thereof disclosed herein comprises an engineered reactive amino acid residue that is conjugated to a ligand via a reactive moiety. In certain embodiments, the engineered reactive amino acid residue is conjugated to the ligand by a linker. In certain embodiments, the linker is cleavable. In certain embodiments, the linker is non-cleavable. In certain embodiments, the ligand to antibody ratio (LAR) is at least 1.5. In certain embodiments, the LAR is at least 1.6. In certain embodiments, the LAR is at least 1.7. In certain embodiments, the LAR is at least 1.8. In certain embodiments, the LAR is at least 1.9. In certain embodiments, the ligand is PEG and the PEG to antibody ratio (PAR) is at least 1.5. In certain embodiments, the PAR is at least 1.6. In certain embodiments, the PAR is at least 1.7. In certain embodiments, the PAR is at least 1.8. In certain embodiments, the PAR is at least 1.9. In certain embodiments, the ligand is a drug and the drug to antibody ratio (DAR) is at least 1.5. In certain embodiments, the DAR is at least 1.6. In certain embodiments, the DAR is at least 1.7. In certain embodiments, the DAR is at least 1.8. In certain embodiments, the DAR is at least 1.9.

In certain embodiments of the engineered antigen-binding protein or fragment thereof disclosed herein, the engineered antigen-binding protein or fragment thereof comprises an antibody heavy chain constant ($C_H$) domain comprising an engineered reactive amino acid residue and further comprises an antibody heavy chain variable ($V_H$) domain. In certain embodiments, the engineered antigen-binding protein or fragment thereof further comprises an antibody light chain variable ($V_L$) domain. In certain embodiments, the engineered antigen-binding protein or fragment thereof is a chimeric antibody. In certain embodiments, the engineered antigen-binding protein or fragment thereof is a humanized antibody. In certain embodiments, the engineered antigen-binding protein or fragment thereof is a human antibody. In certain embodiments, the engineered antigen-binding protein or fragment thereof is a monoclonal antibody. In certain embodiments, the engineered antigen-binding protein or fragment thereof comprises one or more full-length antibody heavy chains comprising an Fc region. In certain embodiments, the Fc region is a human IgG1 Fc region.

In one aspect of the method disclosed herein, the method of producing a double-engineered antigen-binding protein or fragment thereof, comprising an engineered reactive amino acid residue at a first position and an engineered reactive amino acid residue at a second position, comprises: (a) producing a first library of single-engineered parental antigen-binding proteins or fragments thereof, wherein each parental antigen-binding protein or fragment thereof comprises a single engineered reactive amino acid residue; (b) producing a second library of ligand-conjugated single-engineered parental antigen-binding proteins or fragments thereof by conjugating a ligand to the single engineered reactive amino acid residue of each single-engineered parental antigen-binding protein or fragment thereof comprising the first library; (c) producing a third library of engineered positions by screening the second library for a ligand to antibody ratio (LAR) above 1.7, wherein the positions at which the single-engineered parental antigen-binding proteins or fragments thereof with an LAR above 1.7 have an engineered reactive amino acid residue comprise the third library of engineered positions; (d) producing a fourth library of double-engineered antigen-binding proteins or fragments thereof, wherein each antigen-binding protein or fragment thereof comprises an engineered reactive amino acid residue at a first position selected from the third library of engineered positions and an engineered reactive amino acid residue at a second position selected from the third library of engineered positions; and (e) producing a fifth library of ligand-conjugated double-engineered antigen-binding proteins or fragments thereof by conjugating a ligand to the engineered reactive amino acid residue at the first position and the engineered reactive amino acid residue at the second position; and (f) producing a sixth library of double-engineered antigen-binding proteins or fragments thereof by screening the fifth library for an LAR above 3.4.

In certain embodiments, the method of producing a double-engineered antigen-binding protein or fragment thereof, further comprises producing a third library of engineered positions by screening the second library for conjugation of 60% or above of one ligand per single-engineered parental antigen-binding protein or fragment thereof, conjugation of 20% or below of multiple ligands per single-engineered parental antigen-binding protein or fragment thereof, and conjugation of 20% or below of no ligand per single-engineered parental antigen-binding protein or fragment thereof. In certain embodiments, the method of producing a double-engineered antigen-binding protein or fragment thereof, further comprises producing a third library of engineered positions by screening the second library for conjugation of 60% to 95% of one ligand per single-engineered parental antigen-binding protein or fragment thereof, conjugation of 5% to 20% of multiple ligands per single-engineered parental antigen-binding protein or fragment thereof, and conjugation of 5% to 20% of no ligand per single-engineered parental antigen-binding protein or fragment thereof. In certain embodiments, the method of producing a double-engineered antigen-binding protein or fragment thereof, further comprises producing a third library of engineered positions by screening the second library for conjugation of 60% to 90% of one ligand per single-engineered parental antigen-binding protein or fragment thereof, conjugation of 10% to 20% of multiple ligands per single-engineered parental antigen-binding protein or fragment thereof, and conjugation of 10% to 20% of no ligand per single-engineered parental antigen-binding protein or fragment thereof. In certain embodiments, the method of producing a double-engineered antigen-binding protein or fragment thereof, further comprises producing a third library of engineered positions by screening the second library for conjugation of 60% to 85% of one ligand per single-engineered parental antigen-binding protein or fragment thereof, conjugation of 15% to 20% of multiple ligands per single-engineered parental antigen-binding protein or fragment thereof, and conjugation of 15% to 20% of no ligand per single-engineered parental antigen-binding protein or fragment thereof.

In certain embodiments, the method of producing a double-engineered antigen-binding protein or fragment thereof, further comprises producing a sixth library of double-engineered antigen-binding proteins or fragments thereof by screening the fifth library for conjugation of 80% or above of one or two ligands per double-engineered antigen-binding protein or fragment thereof, conjugation of 10% or below of multiple ligands per double-engineered antigen-binding protein or fragment thereof, and conjugation of 5% or below of no ligand per double-engineered antigen-binding protein or fragment thereof. In certain embodiments, the method of producing a double-engineered antigen-binding protein or fragment thereof, further comprises producing a sixth library of double-engineered antigen-binding proteins or fragments thereof by screening the fifth library for conjugation of 80% to 99% of one or two ligands per double-engineered antigen-binding protein or fragment thereof, conjugation of 1% to 10% of multiple ligands per double-engineered antigen-binding protein or fragment thereof, and conjugation of 1% to 5% of no ligand per double-engineered antigen-binding protein or fragment thereof. In certain embodiments, the method of producing a double-engineered antigen-binding protein or fragment thereof, further comprises producing a sixth library of double-engineered antigen-binding proteins or fragments thereof by screening the fifth library for conjugation of 80% to 95% of one or two ligands per double-engineered antigen-binding protein or fragment thereof, conjugation of 2% to 10% of multiple ligands per double-engineered antigen-binding protein or fragment thereof, and conjugation of 2% to 5% of no ligand per double-engineered antigen-binding protein or fragment thereof. In certain embodiments, the method of producing a double-engineered antigen-binding protein or fragment thereof, further comprises producing a sixth library of double-engineered antigen-binding proteins or fragments thereof by screening the fifth library for conjugation of 80% to 90% of one or two ligands per double-engineered antigen-binding protein or fragment thereof, conjugation of 5% to 10% of multiple ligands per double-engineered antigen-binding protein or fragment thereof, and conjugation of 3% to 5% of no ligand per double-engineered antigen-binding protein or fragment thereof.

In certain embodiments, the method of producing a double-engineered antigen-binding protein or fragment thereof, further comprises conjugating a ligand to the engineered reactive amino acid residues of the double-engineered antigen-binding proteins or fragments thereof comprising the sixth library. In certain embodiments, the engineered reactive amino acid residue is cysteine, lysine, histidine, serine, methionine, tryptophan, tyrosine, aspartate, glutamate, or arginine. In certain embodiments, the engineered reactive amino acid residue is cysteine. In certain embodiments, the engineered reactive amino acid residue is lysine. In certain embodiments, the engineered reactive amino acid residue is conjugated to a ligand via a reactive moiety. In certain embodiments, the engineered reactive amino acid residue is conjugated to the ligand by a linker. In certain embodiments, the linker is cleavable. In certain embodiments, the linker is non-cleavable. In certain embodiments, the linker is non-cleavable. In certain embodiments, the LAR is at least 3.0. In certain embodiments, the linker is non-cleavable. In certain embodiments, the LAR is at least 3.1. In certain embodiments, the linker is non-cleavable. In certain embodiments, the LAR is at least 3.2. In certain embodiments, the linker is non-cleavable. In certain embodiments, the LAR is at least 3.3. In certain embodiments, the linker is non-cleavable. In certain embodiments, the LAR is at least 3.4.

In certain embodiments, the method of producing a double-engineered antigen-binding protein or fragment thereof, further comprises screening the first library of single-engineered parental antigen-binding proteins or fragments thereof for thermostability comparable to the thermostability of an un-engineered antigen-binding protein or fragment thereof.

In certain embodiments of the method of producing an engineered antigen-binding protein or fragment thereof, the engineered antigen-binding protein or fragment thereof comprises an antibody heavy chain constant ($C_H$) domain comprising an engineered reactive amino acid residue and further comprises an antibody heavy chain variable ($V_H$) domain. In certain embodiments, the engineered antigen-binding protein or fragment thereof further comprises an antibody light chain variable ($V_L$) domain. In certain embodiments, the engineered antigen-binding protein or fragment thereof is a chimeric antibody. In certain embodiments, the engineered antigen-binding protein or fragment thereof is a humanized antibody. In certain embodiments, the engineered antigen-binding protein or fragment thereof is a human antibody. In certain embodiments, the engineered antigen-binding protein or fragment thereof is a monoclonal antibody. In certain embodiments, the engineered antigen-binding protein or fragment thereof comprises one or more full-length antibody heavy chains comprising an Fc region. In certain embodiments, the Fc region is a human IgG1 Fc region.

B.1.a. Ligands

In certain embodiments, a ligand is an agent (e.g. protein, nucleic acid, lipid, carbohydrate, glycopeptide, or fragment thereof) with biological or other functional activity. In certain embodiments, a modified antigen-binding protein comprising a ligand-conjugated to an antigen-binding protein has at least one additional function or property as compared to the unconjugated antibody.

In certain embodiments, a ligand is conjugated to an antigen-binding protein or antibody to serve a variety of purposes and/or functions, including, but not limited to, serving as a targeting moiety, serving as a diagnostic agent, serving as a proxy for a drug, and/or serving as a drug. In certain embodiments, the ligand is a targeting moiety, which may be a protein, nucleic acid, lipid, carbohydrate, and/or a combination thereof.

In certain embodiments, the ligand comprises targeting moieties that specifically bind to one or more target molecules. Any type of targeting moiety can be employed including, without limitation, proteins, nucleic acids, lipids, carbohydrates (e.g., glycans), and combinations thereof (e.g., glycoproteins, glycopeptides, and glycolipids). In certain embodiments, the targeting moiety is a carbohydrate or glycopeptide. In one embodiment, the targeting moiety is a trivalent glycopeptide (e.g. a trivalent GalNAc glycan containing glycopeptide or a trivalent galactose containing glycopeptide). In a specific embodiment, the trivalent galactose containing polypeptide is lactose$_3$-Cys$_3$Gly$_4$. In certain embodiments, the targeting moiety is a glycan. Targeting moieties can be naturally or non-naturally occurring molecules. Targeting moieties suitable for conjugation may include those containing aminooxy linkers.

The targeting moieties described in the present invention may bind to any type of cell, including animal (e.g., mammalian), plant, or insect cells either in vitro or in vivo, without limitation. The cells may be of endodermal, mesodermal, or ectodermal origins, and may include any cell type. In certain embodiments, the targeting moiety binds to a cell, e.g., a mammalian cell, a facilitates delivery of an antigen-binding protein to the targeted cell, e.g., to improve cell-targeting and/or uptake. Exemplary target cells include, without limitation, immune cells (e.g., lymphocytes such as B cells, T cells, natural killer (NK) cells, basophils, macrophages, or dendritic cells), liver cells (e.g., hepatocytes or non-parenchymal cells such as liver sinusoidal endothelial cells, Kupffer cells, or hepatic stellate cells), tumor cells (e.g., any malignant or benign cell including hepatoma cells, lung cancer cells, sarcoma cells, leukemia cells, or lymphoma cells), vascular cells (e.g., aortic endothelial cells or pulmonary artery endothelial cells), epithelial cells (e.g., simple squamous epithelial cells, simple columnar epithelial cells, pseudostratified columnar epithelial cells, or stratified squamous epithelial cells), or mesenchymal cells (e.g., cells of the lymphatic and circulatory systems, bone, and cartilage cells).

In one embodiment, the antigen-binding protein is internalized by the cell. In another embodiment, the amount of the antigen-binding protein internalized by the cell is greater than the amount of a reference antigen-binding protein lacking a targeting moiety internalized by the cell.

In one embodiment, the targeting moiety binds to a receptor on the target cell. For example, the targeting moiety may comprise a mannose 6 phosphate moiety that binds to a mannose 6 phosphate receptor on the cell. In other exemplary embodiments, the targeting moiety binds to a Siglec on a target cell. Exemplary Siglecs include sialoadhesin (Siglec-1), CD22 (Siglec-2), CD33 (Siglec-3), MAG (Siglec-4), Siglec-5, Siglec-6, Siglec-7, Siglec-8, Siglec-9, Siglec-10, Siglec-11, Siglec-12, Siglec-14, or Siglec-15. In yet other embodiments, the targeting moiety comprises an α2,3-, α2,6-, or α2,8-linked sialic acid residue. In a further embodiment, the targeting moiety comprises an α2,3-siallylactose moiety or an α2,6-siallylactose moiety. Other exemplary receptors include lectin receptors, including but not limited to C-type lectin receptors, galectins, and L-type lectin receptors. Exemplary lectin receptors include: TDEC-205, macrophage mannose receptor (MMR), Dectin-1, Dectin-2, macrophage-inducible C-type lectin (Mincle), dendritic cell-specific ICAM3-grabbing nonintegrin (DC-SIGN, CD209), DC NK lectin group receptor-1 (DNGR-1), Langerin (CD207), CD 169, a lectican, an asialoglycoprotein receptor, DCIR, MGL, a DC receptor, a collectin, a selectin, an NK-cell receptor, a multi-CTLD endocytic receptor, a Reg group (type VII) lectin, chondrolectin, tetranectin, polycystin, attractin (ATRN), eosinophil major basic protein (EMBP), DGCR2, Thrombomodulin, Bimlec, SEEC, and CB CP/Frem 1/QBRICK.

In certain embodiments, the antigen-binding proteins of the current disclosure are conjugated to a ligand comprising a diagnostic agent. In one embodiment, the diagnostic agent is a detectable small molecule label, e.g., fluorophores, chromophores, spin resonance probes, imaging agents, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified antigen-binding protein that undergo structural changes upon binding a substrate (e.g. dansyl probes). Exemplary radiolabels include small molecules containing atoms with one or more low sensitivity nuclei. The radionuclide can be, for example, a gamma, photon, or positron-emitting radionuclide with a half-life suitable to permit activity or detection after the elapsed time between administration and localization to the imaging site.

In one embodiment, the diagnostic agent is a polypeptide. Exemplary diagnostic polypeptides include enzymes with fluorogenic or chromogenic activity, e.g. the ability to cleave a substrate which forms a fluorophore or chromophore as a product (i.e. reporter proteins such as luciferase). Other diagnostic proteins may have intrinsic fluorogenic or chromogenic activity (e.g., green, red, and yellow fluorescent bioluminescent aequorin proteins from bio luminescent marine organisms) or they may comprise a protein containing one or more low-energy radioactive nuclei ($^{13}C$, $^{15}N$, $^{2}H$, $^{125}I$, $^{124}I$, $^{123}I$, $^{99}Tc$, $^{43}K$, $^{52}Fe$, $^{64}Cu$, $^{68}Ga$, $^{111}In$ and the like).

With respect to the use of radiolabeled conjugates in conjunction with the present disclosure, antigen-binding proteins of the current disclosure may be directly labeled (such as through iodination) or may be labeled indirectly through the use of a chelating agent. As used herein, the phrases “indirect labeling” and “indirect labeling approach” both mean that a chelating agent is covalently attached to an antigen-binding protein and at least one radionuclide is associated with the chelating agent. Such chelating agents are typically referred to as bifunctional chelating agents as they bind both the polypeptide and the radioisotope. Exemplary chelating agents comprise 1-isothiocycmatobenzyl-3-methyldiothelene triaminepentaacetic acid (“MX-DTPA”) and cyclohexyl diethylenetriamine pentaacetic acid (“CHX-DTPA”) derivatives. Other chelating agents comprise P-DOTA and EDTA derivatives. Particularly radionuclides for indirect labeling include $^{111}In$ and $^{90}Y$. Most imaging studies utilize 5 mCi $^{111}In$-labeled antibody, because this dose is both safe and has increased imaging efficiency compared with lower doses, with optimal imaging occurring at three to six days after antibody administration. See, for example, Murray, (1985), J. Nuc. Med. 26: 3328 and Carraguillo et al, (1985), J. Nuc. Med. 26: 67. The radionuclide for direct labeling can be, for example, $^{131}I$. Those skilled in the art will appreciate that non-radioactive conjugates may also be assembled depending on the selected agent to be conjugated.

In certain embodiments, the diagnostic agent is a FRET (Fluorescence Resonance Energy Transfer) probe. FRET has been used for a variety of diagnostic applications including cancer diagnostics. A FRET probe may include a cleavable linker (enzyme sensitive or pH linker) connecting the donor and acceptor moieties of the FRET probe, wherein cleavage results in enhanced fluorescence (including near Infrared) (see, e.g., A. Cobos-Correa et. al. Membrane-bound FRET probe visualizes MMP12 activity in pulmonary inflammation, Nature Chemical Biology (2009), 5(9), 628-63; S. Gehrig et. al. Spatially Resolved Monitoring of Neutrophil Elastase Activity with Ratiometric Fluorescent Reporters (2012) Angew. Chem. Int. Ed., 51, 6258-6261).

In certain embodiments, ligands may be functionalized to contain additional groups. For example, the ligand may contain cleavable linkers which release the ligand from the antigen-binding protein under particular conditions. In exemplary embodiments, the ligand may include a linker that is cleavable by cellular enzymes and/or is pH sensitive. Additionally, or alternatively, the ligand may contain a disulfide bond that cleaved by intracellular glutathione upon uptake into the cell.

In yet other embodiments, the ligand may include hydrophilic and biocompatible moieties such as poly(glycine), poly(oxazoline), or PEG moieties.

In other aspects, the ligand is a moiety comprising poly (ethylene glycol) (PEG, PEO, or POE). PEG is an oligomer or polymer of ethylene oxide and has the chemical structure H—(O—CH2-CH2)n-OH wherein the element in parentheses is repeated. PEGylation (or pegylation) is a process in which PEG polymer chains are attached to another molecule (e.g., an antigen-binding protein), which is then described as PEGylated (or pegylated). PEGylation can serve to reduce immunogenicity and antigenicity as well as to increase the hydrodynamic size (size in solution) of the molecule it is attached to, reducing renal clearance and prolonging circulation time. PEGylation can also make molecules more water soluble. In one embodiment of the present invention, the PEG moiety may comprise mono-PEG, bi-PEG, or tri-PEG. In another embodiment, the PEG moiety comprises 3 to 3.5 PEG.

In certain embodiments, the ligand contains an aminooxy group which facilitates conjugation to an antigen-binding protein via a stable oxime linkage.

In other embodiments, the ligand contains a hydrazide and/or N-alkylated hydrazine group to facilitate conjugation to an antigen-binding protein via a stable hydrazone linkage.

The antigen-binding proteins of the present invention may be used to remove toxic compounds and harmful substances into liver in multiple diseases by targeting carbohydrate receptors (e.g., mannose 6-phosphate receptor, mannose receptor, and asialoglycoprotein receptor). Please see: Ganesan, L. P. et al: Rapid and Efficient Clearance of Blood-borne Virus by Liver Sinusoidal Endothelium. PLoS Pathogens 2011, 9: 1; and Monnier, V. M. et al: Glucosepane: a poorly understood advanced glycation end product of growing importance for diabetes and its complications. Clin Chem Lab Med 2014; 52: 21.

The antigen-binding proteins of the present invention may also be used to target tumor cells through targeting different cell receptors including, but not limited to: carbohydrate receptors, Asialoglycoprotein receptor, and Siglecs. Please see: Chen, W. C. et al: In vivo targeting of B-cell lymphoma with glycan ligands of CD22. Blood 2010, 115: 4778; Chen, W. C. et al: Targeting B lymphoma with nanoparticles bearing glycan ligands of CD22. Leuk Lymphoma 2012, 53: 208; Hatakeyama, S. et al: Targeted drug delivery to tumor vasculature by a carbohydrate mimetic peptide. PNAS, 2011, 108: 19587; Hong, F. et al: 0-Glucan Functions as an Adjuvant for Monoclonal Antibody Immunotherapy by Recruiting Tumoricidal Granulocytes as Killer Cells. Cancer Res. 2003, 23: 9023; Kawasakia, N. et al: Targeted delivery of lipid antigen to macrophages via the CD169/sialoadhesin endocytic pathway induces robust invariant natural killer T cell activation. PNAS 2013, 110: 7826; and Medina, S. H. et al: N-acetylgalactosamine-functionalized dendrimers as hepatic cancer cell-targeted carriers. Biomaterials 2011, 32: 4118.

The binding peptides of the present invention may also be used to regulate immune response through various receptors including, but not limited to, carbohydrate receptors, DC-SIGN, or Siglecs.

B.1.b. Drug Proxies

In certain embodiments, the ligand is a detection probe, which may be a biotin, polyethylene glycol (PEG), fluorescence tag, visualization peptide, and/or a combination thereof. In certain embodiments, a detection probe that is conjugated to an antigen-binding protein or antibody serves as a proxy for a drug, in part because the ligand is comparable in size with that of the drug. In certain embodiments, the detection probe is biotin. In certain embodiments, the detection probe is PEG. In certain embodiments, the PEG has a molecular weight of 15,000-20,000 g/mol or 15-20 kDa. In certain embodiments, the PEG has a molecular weight of 10,000-15,000 g/mol or 10-15 kDa. In certain embodiments, the PEG has a molecular weight of 5,000-10,000 g/mol or 5-10 kDa. In certain embodiments, the PEG has a molecular weight of 4,000-5,000 g/mol or 4-5 kDa. In certain embodiments, the PEG has a molecular weight of 3,000-4,000 g/mol or 3-4 kDa. In certain embodiments, the PEG has a molecular weight of 2,000-3,000 g/mol or 2-3 kDa. In certain embodiments, the PEG has a molecular weight of 1,000-2,000 g/mol or 1-2 kDa. In certain embodiments, the PEG has a molecular weight of 900-1,000 g/mol or 0.9-1 kDa. In certain embodiments, the PEG has a molecular weight of 800-900 g/mol or 0.8-0.9 kDa. In certain embodiments, the PEG has a molecular weight of 700-800 g/mol or 0.7-0.8 kDa. In certain embodiments, the PEG has a molecular weight of 600-700 g/mol or 0.6-0.7 kDa. In certain embodiments, the PEG has a molecular weight of 500-600 g/mol or 0.5-0.6 kDa. In certain embodiments, the PEG has a molecular weight of 400-500 g/mol or 0.4-0.5 kDa. In certain embodiments, the PEG has a molecular weight of 300-400 g/mol or 0.3-0.4 kDa.

Using a ligand or detection probe as a proxy for a drug can enable screening antibody-ligand conjugates for desirable properties, including, but not limited to, thermostability, structural integrity, antigen-binding capability, and/or conjugation efficiency. One measure of conjugation efficiency is the ligand to antibody ratio (LAR), the PEG to antibody ratio (PAR), and/or the drug to antibody ratio (DAR).

B.1.c. Drugs

In certain embodiments, the ligand is a drug.

In certain embodiments, the conjugation of a ligand that is a cytotoxic drug to an antibody results in the formation of an antibody with drug cytotoxicity as a second function (i.e. in addition to antigen binding). In certain embodiments, the conjugation of a second antibody to the antibody may confer additional binding properties. In certain embodiments, where the ligand is a genetically encoded therapeutic or diagnostic protein or nucleic acid, the ligand may be synthesized or expressed by either peptide synthesis or recombinant DNA methods that are well known in the art. In certain embodiments, where the ligand is a non-genetically encoded peptide, or drug, the ligand may be synthesized artificially or purified from a natural source.

In certain embodiments, the drug is a prodrug. Prodrugs include, but are not limited to, phosphate-containing prodrugs, amino acid-containing prodrugs, thiophosphate-containing prodrugs, sulfate-containing prodrugs, peptide-containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. One skilled in the art may make chemical modifications to the desired drug or its prodrug in order to make reactions of that compound more convenient for purposes of preparing modified antigen-binding proteins of the current disclosure. The drugs also include derivatives, pharmaceutically acceptable salts, esters, amides, and ethers of the drugs described herein. Derivatives include modifications to drugs identified herein which may improve or not significantly reduce a particular drug's desired therapeutic activity.

In certain embodiments, the drug may be an anti-cancer therapeutic agent, anti-inflammatory therapeutic agent, anti-infective therapeutic agent, anesthetic therapeutic agent, cytotoxic therapeutic agent, radionuclide, immunomodulator, cell signaling peptide, growth factor, enzyme, oligonucleotide, photoactive therapeutic agent, and/or a combination thereof.

In certain embodiments, the drug is an anti-cancer therapeutic agent or anti-cancer agent. Examples of such an agent include, but are not limited to, a cytostatic, cytotoxic nucleoside, tubulin binding agent, hormone and hormone antagonist, anti-angiogenesis agent, enzyme inhibitor, gene regulator, proteasome inhibitor, pteridine, diynene, podophyllotoxin, auristatin, geldanamycin, calicheamicin, gramicidin D, maytansanoids, neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, maytansine derivative, anthracycline derivative, bisphosphonate derivative, leptomycin derivative, streptonigrin derivative, auristatine derivative, duocarmycin derivative, and/or any combination thereof.

In certain embodiments, the drug is a cytostatic that may be an anthracine, DNA synthesis inhibitor, DNA-intercalator, DNA-RNA transcription regulator, ansamycin benzoquinone, quinonoid derivative, busulfan, ifosfamide, mechlorethamine, triaziquone, diaziquone, carbazilquinone, indoloquinone E09, diaziridinyl-benzoquinone methyl DZQ, triethylenephosphoramide, nitrosourea compound, and/or any combination thereof.

Exemplary cytostatic anti-cancer agents include alkylating agents such as the anthracycline family of drugs (e.g. adriamycin, carminomycin, cyclosporin-A, chloroquine, methopterin, mithramycin, porfiromycin, streptonigrin, porfiromycin, anthracenediones, and aziridines). Other cytostatic anti-cancer agents include DNA synthesis inhibitors (e.g., methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C), DNA-intercalators or cross-linkers (e.g., bleomycin, carbop latin, carmustine, chlorambucil, cyclophosphamide, cis-diammineplatinum(II) dichloride (cisplatin), melphalan, mitoxantrone, and oxaliplatin), and DNA-RNA transcription regulators (e.g., actinomycin D, daunorubicin, doxorubicin, homoharringtonine, and idarubicin). Other exemplary cytostatic agents that are compatible with the present disclosure include ansamycin benzoquinones, quinonoid derivatives (e.g. quinolones, genistein, bactacyclin), busulfan, ifosfamide, mechlorethamine, triaziquone, diaziquone, carbazilquinone, indoloquinone E09, diaziridinyl-benzoquinone methyl DZQ, triethylenephosphoramide, and nitrosourea compounds (e.g. carmustine, lomustine, semustine).

In certain embodiments, the drug is a cytotoxic nucleoside that may be an adenosine arabinoside, cytarabine, cytosine arabinoside, 5-fluorouracil, fludarabine, floxuridine, ftorafur, 6-mercaptopurine, and/or any combination thereof.

In certain embodiments, the drug is a tubulin binding agent. Exemplary tubulin binding agents include, but are not limited to: taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)).

In certain embodiments, the drug is a hormone and hormone antagonist. Exemplary anti-cancer hormones and hormone antagonists include, but are not limited to: corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. amino gluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-a, rapamycin, sex hormone-binding globulin, and thapsigargin. Exemplary anti-cancer, anti-angiogenesis compounds include, but are not limited to: Angiostatin Kl-3, DL-a-difluoromethyl-ornithine, endostatin, fumagillin, genistein, minocycline, staurosporine, and (+)-thalidomide.

In certain embodiments, the drug is an anti-angiogenesis agent that may be an Angiostatin Kl-3, DL-a-difluoromethyl-ornithine, endostatin, fumagillin, genistein, minocycline, staurosporine, (+)-thalidomide, and/or any combination thereof.

In certain embodiments, the drug is an enzyme inhibitor. Exemplary anti-cancer enzyme inhibitors include, but are not limited to: S(+)-camptothecin, curcumin, (−)-deguelin, 5,6-diChlorobenz-imidazole I-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

In certain embodiments, the drug is a gene regulator. Exemplary anti-cancer gene regulators include, but are not limited to: 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Other classes of anti-cancer agents include, but are not limited to: the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like. Still other anti-cancer agents that are compatible with the teachings herein include auristatins (e.g. auristatin E and monomethylauristan E), geldanamycin, calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof. Still other anti-cancer agents that are compatible with the teachings herein include maytansine derivatives, anthracycline derivatives, bisphosphonate derivatives, leptomycin derivatives, streptonigrin derivatives, auristatine derivatives, and duocarmycin derivatives.

Another class of compatible anti-cancer agents that may be used as drugs are radiosensitizing drugs that may be effectively directed to tumor or immunoreactive cells. Such drug moieties enhance the sensitivity to ionizing radiation, thereby increasing the efficacy of radiotherapy. Not to be limited by theory, but an antibody modified with a radiosensitizing drug and internalized by the tumor cell would deliver the radiosensitizer nearer the nucleus where radiosensitization would be maximal. Antibodies which lose the radiosensitizer moiety would be cleared quickly from the blood, localizing the remaining radiosensitization agent in the target tumor and providing minimal uptake in normal tissues. After clearance from the blood, adjunct radiotherapy could be administered by external beam radiation directed specifically to the tumor, radioactivity directly implanted in the tumor, or systemic radioimmunotherapy with the same modified antibody. In one embodiment, the therapeutic agent comprises radionuclides or radio labels with high-energy ionizing radiation that are capable of causing multiple strand breaks in nuclear DNA, leading to cell death. Exemplary high-energy radionuclides include: $^{90}Y$ $^{125}I$, $^{131}I$, $^{123}I$, $^{m}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., PNAS, 95: 13206-10, 1998).

In certain embodiments, the drug is a radioactive isotope. Examples of radioactive isotopes include, but are not limited to, radioactive isotopes suitable for treating cancer, such as $At^{211}$, $Bi^{212}$, $Er^{169}$, $I^{131}$, $I^{125}$, $Y^{90}$, $I^{111}$, $R^{32}$, $Re^{186}$, $Re^{188}$, $Sm^{153}$, $Sr^{89}$, and radioactive isotopes of Lu. Such radioisotopes generally emit mainly beta-radiation. In an embodiment the radioactive isotope is alpha-emitter isotope, more precisely Thorium 227 which emits alpha-radiation.

B.1.d. Proteolysis-Targeting Chimera (PROTAC) Ligands

As defined herein, the phrase "proteolysis-targeting chimera" or "PROTAC" refers to a bifunctional molecule that comprises a protein of interest (POI) ligand (i.e., a ligand that binds a protein of interest) and an E3 ubiquitin ligase (E3) recruiting ligand connected by a linker. PROTACs initiate a degradation cascade by forming a ternary complex with a POI and an E3, bringing the ubiquitination machinery in close proximity for subsequent POI ubiquitination. The polyubiquitinated POI is then recognized and degraded by the 26S proteasome. The 26S proteasome is part of the ubiquitin-proteasome system (UPS) which is the primary mechanism used by eukaryotic cells to regulate protein levels. Accordingly, PROTACs are useful ligands for the targeting and degradation of intracellular proteins. Additional PROTAC disclosure and exemplary PROTACs are described in Pettersson et al. (Drug Discov Today Technol. 2019. 31: 15-27) and Maneiro et al. (ACS Chem Biol. 2020. 15(6): 1306-1312), each of which is incorporated herein by reference.

In certain embodiments, the antigen-binding protein or fragment thereof of the disclosure comprises an engineered reactive amino acid residue that is conjugated to a PROTAC via a reactive moiety. In further embodiments, a linker conjugates the engineered reactive amino acid residue to the PROTAC.

B.1.e. Lysosome Targeting Chimera (LYTAC) Ligands

As defined herein, the phrase "lysosome-targeting chimera" or "LYTAC" refers to a bifunctional molecule that comprises a region capable of binding a cell surface lysosome targeting receptor and a region capable of binding an extracellular domain of a target protein, including, but not limited to, secreted extracellular proteins and the extracellular domain of a membrane-bound protein. Accordingly, LYTACs are useful alternatives to PROTACs described above when the target protein of interest is not intracellular. Additional LYTAC disclosure and exemplary LYTACs are described in Banik et al. (ChemRxiv. 2019), Banik et al. (Nature. 2020. 584: 291-297), WO2015/143091, and WO2020/132100, each of which is incorporated herein by reference. As used herein, the portion of the LYTAC that is capable of binding an extracellular domain of a target protein corresponds to the antigen-binding protein or fragment thereof of the disclosure.

In certain embodiments, the antigen-binding protein or fragment thereof of the disclosure comprises an engineered reactive amino acid residue that is conjugated to a LYTAC via a reactive moiety. In further embodiments, a linker conjugates the engineered reactive amino acid residue to the LYTAC.

In certain embodiments, the region of the LYTAC capable of binding a cell surface lysosome targeting receptor comprises mannose-6-phosphate (M6P) or derivatives thereof, GalNAc (e.g., trivalent GalNAc), and glycopeptides. In certain embodiments, the cell surface lysosome targeting receptor comprises an asialoglycoprotein receptor (ASGPR), a mannose-6-phosphate receptor (M6PR) (including, but not limited to, a cation-independent M6PR), and a sialic acid-binding immunoglobulin-type lectin (Siglec).

B.1.f. Ligand to Antibody Ratio (LAR)

As defined herein, the phrase "ligand to antibody ratio" or "LAR" refers to the stoichiometric ratio of the number of ligand molecules bound to one antibody. If the ligand is a PEG molecule, which can act as a drug proxy, the phrase "PEG to antibody ratio" or "PAR" refers to the stoichiometric ratio of the number of PEG molecules bound to one antibody. If the ligand is a drug, the phrase "drug to antibody ratio" or "DAR" refers to the stoichiometric ratio of the number of drug molecules bound to one antibody.

According to an embodiment, the conjugate according to the invention is characterized by a LAR/PAR/DAR ranging from 1 to 10, for instance from 2 to 5, in particular from 3 to 4. This is generally the case of conjugates including maytansinoid molecules. This LAR/PAR/DAR number can vary with the nature of the antibody and of the drug (i.e. the growth-inhibitory agent) used along with the experimental conditions used for the conjugation (like the ratio growth-inhibitory agent/antibody, the reaction time, the nature of the solvent and of the cosolvent if any). Thus, the contact between the antibody and the growth-inhibitory agent leads to a mixture comprising several conjugates differing from one another by different ligand/PEG/drug to antibody ratios; optionally the naked antibody; optionally aggregates. The LAR/PAR/DAR that is determined is thus a mean value.

A method which can be used to determine the LAR/PAR/DAR consists in measuring spectrophotometrically the ratio of the absorbance at of a solution of substantially purified conjugate at XD and 280 nm. 280 nm is a wavelength generally used for measuring protein concentration, such as antibody concentration. The wavelength kD is selected so as to allow discriminating the drug from the antibody, i.e. as readily known to the skilled person, kD is a wavelength at which the drug has a high absorbance and XD is sufficiently remote from 280 nm to avoid substantial overlap in the absorbance peaks of the drug and antibody. XD may be selected as being 252 nm in the case of maytansinoid molecules. A method of LAR/PAR/DAR calculation may be derived from Antony S. Dimitrov (ed), LLC, 2009, Therapeutic Antibodies and Protocols, vol 525, 445, Springer Science.

LAR/PAR/DAR is calculated as follows. A conjugate comprises generally from 1 to 10 molecule(s) of the maytansinoid attached covalently to the antibody (LAR or DAR). This number can vary with the nature of the antibody and of the maytansinoid used along with the experimental conditions used for the conjugation (like the ratio maytansinoid/antibody, the reaction time, the nature of the solvent and of the cosolvent if any). Thus, the contact between the antibody and the maytansinoid leads to a mixture comprising several conjugates differing from one another by different ligand/PEG/drug to antibody ratios; optionally the naked antibody; optionally aggregates. The LAR/PAR/DAR that is determined is thus a mean value.

The method used herein to determine the LAR consists in measuring spectrophotometrically the ratio of the absorbance at 252 nm and 280 nm of a solution of the substantially purified conjugate. In particular, said LAR can be determined spectrophotometrically using the measured extinction coefficients at respectively 280 and 252 nm for the antibody and for the maytansinoid ($\varepsilon_{D250}$=5,180 $M^{-1}$ $cm^{-1}$ and $\varepsilon_{D252}$=26,159 $M^{-1}$ $cm^{-1}$). The method of calculation is derived from Antony S. Dimitrov (ed), LLC, 2009, Therapeutic Antibodies and Protocols, vol 525, 445, Springer Science and is described in more details below:

The absorbances for the conjugate at $\lambda_D$ ($A_{\lambda D}$) and at 280 nm ($A_{280}$) are measured either on the monomeric peak of the size exclusion chromatography (SEC) analysis (allowing to calculate the "LAR(SEC)" parameter) or using a classic spectrophotometer apparatus (allowing to calculate the "LAR(UV)" parameter). The absorbances can be expressed as follows:

$$A_{\lambda D} = (C_D \times \varepsilon_{D\lambda D}) + (C_A \times \varepsilon_{A\lambda D})$$

$$A_{280} = (C_D \times \varepsilon_{D280}) + (C_A \times \varepsilon_{A280})$$

wherein:

$c_D$ and $c_A$ are respectively the concentrations in the solution of the ligand/drug and of the antibody $\varepsilon_{D\lambda D}$ and $\varepsilon_{D280}$ are respectively the molar extinction coefficients of the ligand/drug at $\lambda_D$ and 280 nm $\varepsilon_{A\lambda D}$ and $\varepsilon_{A280}$ are respectively the molar extinction coefficients of the antibody at $\lambda_D$ and 280 nm.

Resolution of these two equations with two unknowns leads to the following equations:

$$C_D = [(\varepsilon_{A280} \times (\varepsilon_{A\lambda D} \times A_{280})]/[\varepsilon_{D\lambda D} \times \varepsilon_{A280}) - (\varepsilon_{A\lambda D} \times \varepsilon_{D280})]$$

$$C_A = [A_{280} - (C_D \times \varepsilon_{D280})]/\varepsilon_{A280}$$

The average LAR is then calculated from the ratio of the drug concentration to that of the antibody: LAR=$c_D/c_A$.

B.2. Methods for Producing Antibody-Ligand Conjugates

As used herein, the term "reactive moiety" refers to a moiety comprising a portion of or an entire functional group that comprises one or more atoms and one or more bonds that are responsible for characteristic chemical reactions. In example embodiments, a reactive moiety includes, but is not limited to, an aldehyde moiety, an alkyne, an aminooxy moiety, an azide, a hydrazine, a keto moiety, and a thiol. In some embodiments, the reactive moiety is a terminal reactive moiety. In the reacting step, a first reactive moiety reacts with a second reactive moiety to form a ligand-conjugated antigen-binding protein. An "aldehyde" moiety, as used herein, refers to a formyl functional group and is represented by the following structural formula:

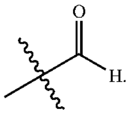

For example, a CMP-sialic acid-derivative comprising a terminal aldehyde moiety includes, but is not limited to, the following structural formulas:

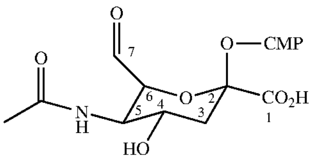

or

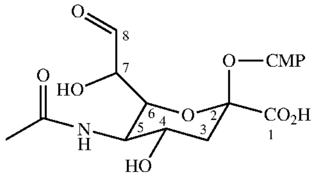

An "alkyne" moiety, as used herein, refers to a carbon-carbon triple bond.

An "aminooxy" moiety, as used herein, refers to a nitrogen-oxygen single bond and is represented by the following structural formula:

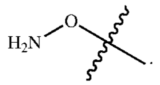

An "azide" moiety, as used herein, refers to an $RN_3$ moiety and may be represented by the following structural formula:

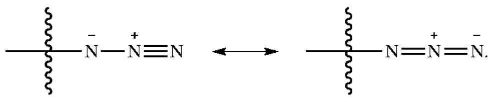

A "hydrazine" moiety, as used herein, refers to at least one nitrogen-nitrogen single bond and is represented by the following structural formula:

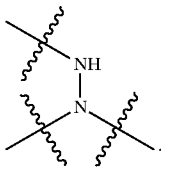 [SMILES: *NN(*)*]

As used herein, an "imine" moiety refers to a carbon-nitrogen double bond and is represented by the following structural formula:

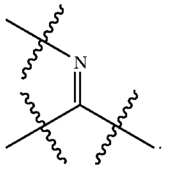 [SMILES: *N=C(*)*]

In some embodiments, a targeting or ligand-conjugated antigen-binding protein comprises an imine. For example, a type of imine includes, but is not limited to, an aldimine, a hydroxylamine, a hydrazone, a ketamine, or an oxime. A "hydrazone" moiety, as used herein, refers to a type of imine and is represented by the following structural formula:

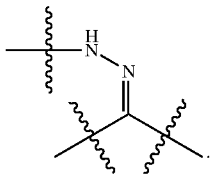 [SMILES: *NN=C(*)*]

In some embodiments, the hydrazone may be a terminal hydrazone. In some embodiments, a hydrazone linkage comprises a hydrazone moiety along with additional functional groups, e.g., a linker or a portion of a linking moiety.

A "keto" or "ketone" moiety, as used herein, comprises a carbonyl functional group and is represented by the following structural formula:

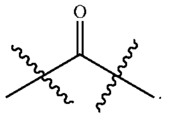 [SMILES: *C(*)=O]

A “maleimide” moiety, as used herein, comprises an unsaturated imide and is represented by the following structural formula:

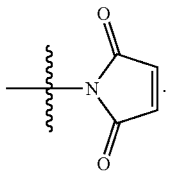 [SMILES: *N1C(=O)C=CC1=O]

An “oxime” moiety is a type of imine and is represented by the following structural formula:

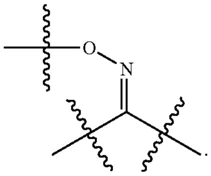 [SMILES: *ON=C(*)*]

A “thiol” refers to a moiety comprising a —SH functional group, which is also referred to as a sulfhydryl group. In some embodiments, a thiol contains a carbon-bonded sulfhydryl group.

The term “terminal” when referring to a reactive moiety, as used herein, describes a group bonded to a terminus of a straight or branched-chain moiety. In some embodiments, the terminal reactive moiety is a substituent of a functional group.

The term “oxidizing agent” refers to a compound or a reagent that accepts or gains electrons from another compound or reagent thereby undergoing a reduction while oxidizing the other compound or reagent. For example, oxidizing agents include, but are not limited to, sodium periodate, periodate oxidase, galactose oxidase, hydrogen peroxide, and copper compounds (e.g., copper(II) sulfate).

The term “ambient temperature” as used herein, is equivalent to the term “room temperature” and denotes the range of temperatures between 20° C. and 26° C. (equivalent to 68° F. and 79° F.), with an average temperature of approximately of 23° C. (73° F.).

Antibody-ligand conjugates may be prepared by in vitro methods known in the art. In order to link a ligand, such as a drug or prodrug to the antibody, a linker or linking group is used. Suitable linking groups are well known in the art and include disulfide groups, thioether groups, acid labile groups, photolabile groups, peptidase labile groups and esterase labile groups. Conjugation of an antibody of the invention with cytotoxic agents or growth inhibitory agents may be made using a variety of bifunctional protein coupling agents including but not limited to N-succinimidyl pyridyldithiobutyrate (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfo-butyric acid (sulfo-SPDB), N-succinimidyl (2-pyridyldithio) propionate (SPDP), succinimidyl (N-maleimidomethyl) cyclohexane-1-carboxylate (SMCC), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026).

The antibodies of the present invention may also be used in Dependent Enzyme Mediated Prodrug Therapy by conjugating the polypeptide to a prodrug-activating enzyme which converts a prodrug (e.g. a peptidyl chemotherapeutic agent, see WO81/01145) to an active anti-cancer drug (See, for example, WO 88/07378 and U.S. Pat. No. 4,975,278). The enzyme component of the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as 0-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. The enzymes can be covalently bound to the polypeptides of the invention by techniques well known in the art such as the use of the heterobifunctional crosslinking reagents discussed above.

In general, the conjugate can be obtained by a process comprising the steps of: (i) bringing into contact an optionally-buffered aqueous solution of a cell-binding agent (e.g. an antibody according to the invention) with solutions of a linker and a cytotoxic compound; (ii) then optionally separating the conjugate which was formed in (i) from the unreacted cell-binding agent.

The aqueous solution of cell-binding agent can be buffered with buffers such as, e.g. potassium phosphate, acetate, citrate or N-2-Hydroxyethylpiperazine-N'-2-ethanesulfonic acid (Hepes buffer). The buffer depends upon the nature of the cell-binding agent. The cytotoxic compound is in solution in an organic polar solvent, e.g. dimethyl sulfoxide (DMSO) or dimethylacetamide (DMA). The reaction temperature is usually comprised between 20 and 40° C. The reaction time can vary from 1 to 24 hours. The reaction between the cell-binding agent and the cytotoxic agent can be monitored by size exclusion chromatography (SEC) with a refractometric and/or UV detector. If the conjugate yield is too low, the reaction time can be extended.

A number of different chromatography methods can be used by the person skilled in the art in order to perform the separation of step (ii): the conjugate can be purified e.g. by SEC, adsorption chromatography (such as ion exchange chromatography, IEC), hydrophobic interaction chromatography (HIC), affinity chromatography, mixed-support chromatography such as hydroxyapatite chromatography, or high-performance liquid chromatography (HPLC). Purification by dialysis or diafiltration can also be used.

After step (i) or (ii), the conjugate-containing solution can be submitted to an additional step (iii) of chromatography, ultrafiltration and/or diafiltration. The conjugate is recovered at the end of these steps in an aqueous solution.

C. Expression of Antigen-Binding Proteins

In one aspect, nucleic acid molecules encoding antigen-binding proteins disclosed herein are provided. Methods of making antigen-binding proteins comprising expressing these nucleic acid molecules or polynucleotides are also provided.

Nucleic acid molecules or polynucleotides encoding the antigen-binding proteins disclosed herein are typically inserted in an expression vector for introduction into host cells that may be used to produce the desired quantity of the claimed antibodies, or fragments thereof. Accordingly, in certain aspects, the disclosure provides expression vectors comprising polynucleotides disclosed herein and host cells comprising these vectors and polynucleotides.

An expression vector is a vehicle for introducing into and expressing a desired gene in a cell. As known to those skilled in the art, such vectors may readily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments, the cloned variable region genes are inserted into an expression vector along with the heavy and light chain constant region genes (e.g., human constant region genes) synthesized as discussed above.

In other embodiments, the antigen-binding proteins may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980, which is incorporated by reference herein in its entirety for all purposes. Those skilled in the art will appreciate that such expression systems may be used to effectively produce the full range of polypeptides disclosed in the instant application.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Plasmid introduction into the host can be by electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, a host cell line used for antibody expression is of mammalian origin. Those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CV-1 (monkey kidney line), COS (a derivative of CV-1 with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (Potelligent® cells) (Biowa, Princeton, N.J.)). In one embodiment, NSO cells may be used. CHO cells are particularly useful. Host cell lines are typically available from commercial services, e.g., the American Tissue Culture Collection, or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the antigen-binding proteins featured in the invention can also be expressed in non-mammalian cells such as bacteria or yeast or plant cells. In this regard it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms, although a number of other strains are commonly available. For expression in *Saccharomyces*, the plasmid YRp7, for example (Stinchcomb et al., Nature, 282:39 (1979); Kingsman et al., Gene, 7:141 (1979); Tschemper et al., Gene, 10:157 (1980)), is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

D. Methods of Administering Antigen-Binding Proteins

Methods of preparing and administering antigen-binding proteins (e.g., antigen-binding proteins disclosed herein) to a subject are well known to or are readily determined by those skilled in the art. The route of administration of the antigen-binding proteins of the current disclosure may be oral, parenteral, by inhalation or topical. The term parenteral as used herein includes intravenous, intraarterial, intraperitoneal, intramuscular, subcutaneous, rectal or vaginal administration. While all these forms of administration are clearly contemplated as being within the scope of the current disclosure, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the modified antibodies can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M or 0.05M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage, and should also be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. Isotonic agents, for example, sugars, polyalcohols, such as mannitol, sorbitol, or sodium chloride may also be included in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a modified antigen-binding protein by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation typically include vacuum drying and freeze-drying, which yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture can include labels or package inserts indicating that the associated compositions are useful for treating a subject suffering from, or predisposed to autoimmune or neoplastic disorders.

Effective doses of the compositions of the present disclosure, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals, including transgenic mammals, can also be treated. Treatment dosages may be titrated using routine methods known to those of skill in the art to optimize safety and efficacy.

For passive immunization with an antigen-binding protein, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example, dosages can be 1 mg/kg body weight or 10 mg/kg body weight or within the range of 1-10 mg/kg, e.g., at least 1 mg/kg. Doses intermediate in the above ranges are also intended to be within the scope of the current disclosure. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen-binding proteins with different binding specificities are administered simultaneously, in which case the dosage of each antibody administered falls within the ranges indicated.

Antigen-binding proteins described herein can be administered on multiple occasions. Intervals between single dosages can be weekly, monthly or yearly. Intervals can also be irregular as indicated by measuring blood levels of modified antigen-binding protein or antigen in the patient. In some methods, dosage is adjusted to achieve a plasma modified antigen-binding protein concentration of 1-1000 μg/ml and in some methods 25-300 μg/ml. Alternatively, antigen-binding proteins can be administered as a sustained release formulation, in which case less frequent administration is required. For antibodies, dosage and frequency vary depending on the half-life of the antibody in the patient. In general, humanized antibodies show the longest half-life, followed by chimeric antibodies and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives. In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug modified antibodies) at relatively short intervals is sometimes required until progression of the disease is reduced or terminated, or until the patient shows partial or complete amelioration of disease symptoms. Thereafter, the patient can be administered a prophylactic regime.

Antigen-binding proteins described herein can optionally be administered in combination with other agents that are effective in treating the disorder or condition in need of treatment (e.g., prophylactic or therapeutic). Effective single treatment dosages (i.e., therapeutically effective amounts) of $^{90}$Y-labeled modified antibodies of the current disclosure range from between about 5 and about 75 mCi, such as between about 10 and about 40 mCi. Effective single treatment non-marrow ablative dosages of $^{131}$I-modified antibodies range from between about 5 and about 70 mCi, such as between about 5 and about 40 mCi. Effective single treatment ablative dosages (i.e., may require autologous bone marrow transplantation) of $^{131}$I-labeled antibodies range from between about 30 and about 600 mCi, such as between about 50 and less than about 500 mCi. In conjunction with a chimeric antibody, owing to the longer circulating half-life vis-a-vis murine antibodies, an effective single treatment non-marrow ablative dosage of $^{131}$I labeled chimeric antibodies ranges from between about 5 and about 40 mCi, e.g., less than about 30 mCi. Imaging criteria for, e.g., an $^{111}$In label, are typically less than about 5 mCi.

While the antigen-binding proteins may be administered as described immediately above, it must be emphasized that in other embodiments antigen-binding proteins may be administered to otherwise healthy patients as a first line therapy. In such embodiments the antigen-binding proteins may be administered to patients having normal or average red marrow reserves and/or to patients that have not, and are not, undergoing one or more other therapies. As used herein, the administration of modified antibodies or fragments thereof in conjunction or combination with an adjunct therapy means the sequential, simultaneous, coextensive, concurrent, concomitant, or contemporaneous administration or application of the therapy and the disclosed antibodies. Those skilled in the art will appreciate that the administration or application of the various components of the combined therapeutic regimen may be timed to enhance the overall effectiveness of the treatment. A skilled artisan (e.g. an experienced oncologist) would be readily be able to discern effective combined therapeutic regimens without undue experimentation based on the selected adjunct therapy and the teachings of the instant specification.

As previously discussed, the antigen-binding proteins of the present disclosure, immunoreactive fragments or recombinants thereof may be administered in a pharmaceutically effective amount for the in vivo treatment of mammalian disorders. In this regard, it will be appreciated that the disclosed antigen-binding proteins will be formulated to facilitate administration and promote stability of the active agent.

Pharmaceutical compositions in accordance with the present disclosure typically include a pharmaceutically acceptable, non-toxic, sterile carrier such as physiological saline, nontoxic buffers, preservatives and the like. For the purposes of the instant application, a pharmaceutically effective amount of the modified antigen-binding protein, immunoreactive fragment or recombinant thereof, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the modified antigen-binding protein will typically be capable of interacting with selected immunoreactive antigens on neoplastic or immunoreactive cells and provide for an increase in the death of those cells. Of course, the pharmaceutical compositions of the present disclosure may be administered in single or multiple doses to provide for a pharmaceutically effective amount of the modified antigen-binding proteins.

In keeping with the scope of the present disclosure, the antigen-binding proteins of the disclosure may be administered to a human or other animal in accordance with the aforementioned methods of treatment in an amount sufficient to produce a therapeutic or prophylactic effect. The antigen-binding proteins of the disclosure can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of antigen-binding proteins described in the current disclosure may prove to be particularly effective.

Pharmaceutical Compositions

The antibodies or immunoconjugates of the invention may be combined with pharmaceutically acceptable excipients, and optionally sustained-release matrices, such as biodegradable polymers, to form therapeutic compositions.

The form of the pharmaceutical compositions, the route of administration, the dosage and the regimen naturally depend upon the condition to be treated, the severity of the illness, the age, weight, and gender of the patient, etc. The pharmaceutical compositions of the invention can be formulated for a topical, oral, parenteral, intranasal, intravenous, intramuscular, subcutaneous or intraocular administration and the like.

In an embodiment, the pharmaceutical compositions contain vehicles which are pharmaceutically acceptable for a formulation capable of being injected. These may be isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical composition can be administrated through drug combination devices.

The doses used for the administration can be adapted as a function of various parameters, and for instance as a function of the mode of administration used, of the relevant pathology, or alternatively of the desired duration of treatment.

To prepare pharmaceutical compositions, an effective amount of the antibody or immunoconjugate of the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and injectable with the appropriate device or system for delivery without degradation. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

A polypeptide, antibody or immunoconjugate of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, glycine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with any of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more concentrated, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibody or immunoconjugate of the invention may be formulated within a therapeutic mixture to comprise about 0.01 to 100 milligrams, per dose or so.

In addition to the antibody or immunoconjugate formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of polypeptides into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles, or biodegradable polylactide or polylactide co glycolide nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MHLVs)). MHLVs generally have diameters of from 25 nm to 4 μm. Sonication of MHLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1—Preparation of Single-Engineered Parental Cysteine Antibodies 29 heavy chain antibody mutants were generated using QuickChange Lightning mutagenesis or Q5 Site Directed Mutagenesis kits following the recommended protocol. Upon generation of the sequences encoding specific single engineered parental cysteine mutation antibodies, the antibodies were expressed in the human embryonic kidney (HEK) cell derived Expi293 cells. Protein expression was performed in a 96-well plate format with 0.5 mL culture media per well and 3 or 5 mL per sample in 96-well plate. The culture media were harvested on day 4 post-transfection. Antibody expression was performed consistent with established Expi293 cell protocols.

Figure 1:
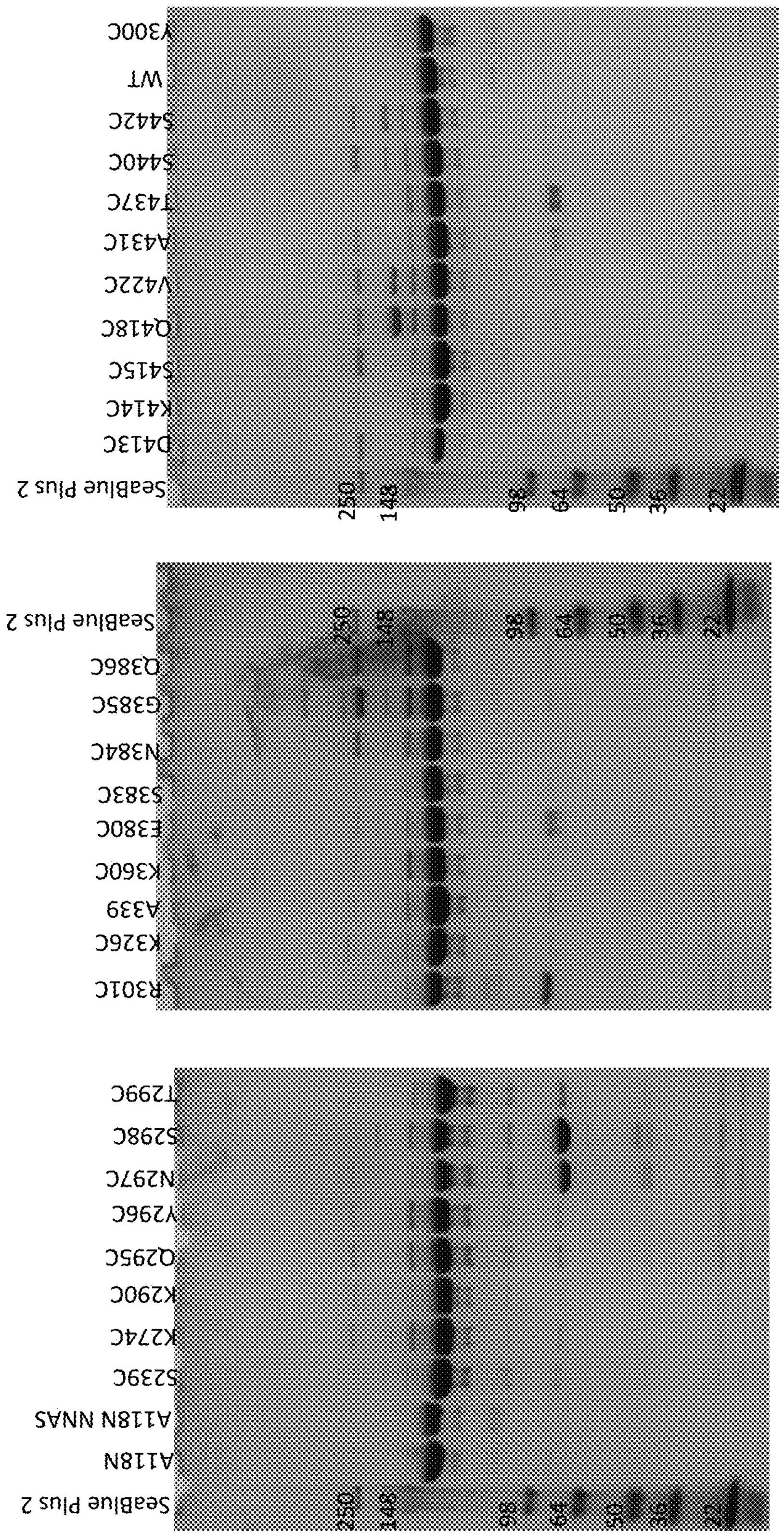
FIG. 1 depicts purified single-engineered parental antibodies on SDS-PAGE. Single-engineered parental antibodies (mutants) with a first position cysteine mutation were loaded onto a 4-12% non-reducing Tris-Glycine SDS-PAGE gel at 4 μg protein/lane.

The antibodies were purified via Protein A-based purification methods. 3 or 5 ml samples were applied to 20 or 80 μl PhyNexus tips on Hamilton Microlab STAR Liquid Handling System. The proteins were captured, washed, and eluted with proprietary PhyNexus buffers (FIG. 1 and Table 1).

TABLE 1

Purified antibody mutants.

| Batch # | Scale (ml) | method | Sample # | Mutant | Yield (mg) | Titer (mg/ml) |
|---|---|---|---|---|---|---|
| 1 | 5 | Hamilton | 1 | K290C | 1.25 | 0.25 |
| 1 | 5 | Hamilton | 2 | Q295C | 1.22 | 0.24 |
| 1 | 5 | Hamilton | 3 | Y296C | 1.23 | 0.25 |
| 1 | 5 | Hamilton | 4 | N297C | 1.29 | 0.26 |
| 1 | 5 | Hamilton | 5 | S298C | 1.11 | 0.22 |
| 1 | 5 | Hamilton | 6 | T299C | 1.28 | 0.26 |
| 1 | 5 | Hamilton | 7 | Y300C | 1.29 | 0.26 |
| 1 | 5 | Hamilton | 8 | R301C | 1.20 | 0.24 |
| 2 | 3 | Hamilton | 1 | K290C | 0.39 | 0.13 |
| 2 | 3 | Hamilton | 2 | N384C | 0.49 | 0.16 |
| 2 | 3 | Hamilton | 3 | S440C | 0.44 | 0.15 |
| 2 | 3 | Hamilton | 4 | S442C | 0.51 | 0.17 |
| 2 | 3 | Hamilton | 5 | S415C | 0.47 | 0.16 |
| 2 | 3 | Hamilton | 6 | S383C | 0.58 | 0.19 |
| 2 | 3 | Hamilton | 7 | K326C | 0.52 | 0.17 |
| 2 | 3 | Hamilton | 8 | E380C | 0.38 | 0.13 |
| 2 | 3 | Hamilton | 9 | S239C | 0.57 | 0.19 |
| 2 | 3 | Hamilton | 10 | A118N NNAS | 0.18 | 0.06 |
| 2 | 3 | Hamilton | 11 | WT | 0.43 | 0.14 |
| 3 | 5 | Protein Maker | 1 | Q295C | 1.29 | 0.26 |
| 3 | 5 | Protein Maker | 2 | Y296C | 1.33 | 0.27 |
| 3 | 5 | Protein Maker | 3 | N297C | 0.92 | 0.18 |
| 3 | 5 | Protein Maker | 4 | S298C | 0.97 | 0.19 |
| 3 | 5 | Protein Maker | 5 | T299C | 1.00 | 0.20 |
| 4 | 5 | Protein Maker | 1 | Y300C | 0.83 | 0.17 |
| 4 | 5 | Protein Maker | 2 | D413C | 0.54 | 0.11 |
| 4 | 5 | Protein Maker | 3 | A339C | 0.52 | 0.10 |
| 4 | 5 | Protein Maker | 4 | Q418C | 0.88 | 0.18 |
| 4 | 5 | Protein Maker | 5 | A118N | 1.01 | 0.20 |
| 4 | 5 | Protein Maker | 6 | A431C | 0.87 | 0.17 |
| 4 | 5 | Protein Maker | 7 | K414C | 1.04 | 0.21 |
| 4 | 5 | Protein Maker | 8 | Q386C | 1.02 | 0.20 |
| 4 | 5 | Protein Maker | 9 | K274C | 1.07 | 0.21 |
| 4 | 5 | Protein Maker | 10 | G385C | 1.06 | 0.21 |
| 4 | 5 | Protein Maker | 11 | V422C | 1.21 | 0.24 |
| 4 | 5 | Protein Maker | 12 | T437C | 0.95 | 0.19 |
| 4 | 5 | Protein Maker | 13 | K360C | 0.93 | 0.19 |
| 4 | 5 | Protein Maker | 14 | N384C | 0.83 | 0.17 |
| 4 | 5 | Protein Maker | 15 | S440C | 0.75 | 0.15 |
| 4 | 5 | Protein Maker | 16 | S442C | 1.11 | 0.22 |
| 4 | 5 | Protein Maker | 17 | S415C | 0.78 | 0.16 |
| 4 | 5 | Protein Maker | 18 | S383C | 1.2 | 0.24 |
| 4 | 5 | Protein Maker | 19 | E380C | 1.01 | 0.20 |
| 4 | 5 | Protein Maker | 20 | S239C | 0.92 | 0.18 |
| 4 | 5 | Protein Maker | 21 | A118N NNAS | 1.56 | 0.31 |
| 4 | 5 | Protein Maker | 22 | wt | 1.17 | 0.23 |

The thermostability of the single-engineered parental cysteine mutants was measured and compared to un-engineered antibody using Nano DSF (FIG. 2).

Nano DSF is a modified differential scanning fluorimetry method to determine protein stability employing intrinsic tryptophan or tyrosine fluorescence. Protein stability is typically addressed by thermal or chemical unfolding experiments. In thermal unfolding experiments, a linear temperature ramp is applied to unfold proteins, whereas chemical unfolding experiments use chemical denaturants in increasing concentrations. The thermal stability of a protein is typically described by the 'melting temperature' or 'Tm', at which 50% of the protein population is unfolded, corresponding to the midpoint of the transition from folded to unfolded. In contrast to conventional DSF methods, nanoDSF uses tryptophan or tyrosine fluorescence to monitor protein unfolding. Both the fluorescence intensity and the fluorescence maximum strongly depend on the close surroundings of the tryptophan. Therefore, the ratio of the fluorescence intensities at 350 nm and 330 nm is suitable to detect any changes in protein structure, for example due to protein unfolding. Its applications include antibody engineering, membrane protein research, quality control and formulation development.

Example 2—Preparation of Conjugated Single-Engineered Parental Cysteine Antibodies Various antibody cysteine mutants were investigated for conjugatability using THIOMAB approach with maleimide PEG (5 kDa). The THIOMAB approach refers to the specific engineering of cysteine residues into the constant region of an antibody. This approach is detailed further in Sochaj et al. (Biotechnology Advances. 2015. 33(6): 775-784), incorporated herein by reference. The conjugation protocol used for obtaining the bold residues in FIG. 6 (K274C, K290C, A339C, K360C) was chosen after initially comparing different methods, such as partial reductions with TCEP and cysteine. Both Coomassie and PEG staining of SDS-PAGE gels was used to detect PEGylation. However, Coomassie staining alone was used for conjugation ranking. Mutants were screened under non-reducing and reducing conditions. Uncapping was performed with 64 eq of DTT (FIG. 3, FIG. 4, FIG. 5, FIG. 6).

27 antibody mutants containing an unpaired cysteine residue were expressed. Mutants were ranked by degree and selectivity of PEGylation, which served as a proxy for drug-based conjugation due to the size of the PEG molecule. The selection criteria are recited below:

≥60% mono-PEGylated

≤20% multi-PEGylated

PEG: Antibody Ratio (PAR) ≥1.7

≤20% un-PEGylated

Based on the above selection criteria, 14 single-engineered cysteine mutants were identified. Among the 14 selected, the following 10 mutants were considered preferred: A339C, S440C, K290C, S442C, K274C, V422C, N384C, G385C, Q418C, K360C.

The method employed to identify preferred mutations was based on the following formula:

$F_{mono}-F_{multi}-F_{un}$ $F_{mono}$=fraction mono-PEGylated, $F_{multi}$=fraction multi-PEGylated, $F_{un}$=fraction un-PEGylated Mutants excluded that did not match the criteria above, or that contain significant free HL (free heavy chain as shown in SDS-PAGE)

PEG staining confirmed that higher molecular weight bands were PEGylation, not aggregation. In other words, these higher molecular weight bands corresponded to higher PEGylation, not PEGylation of higher molecular weight species.

Example 3—Preparation of Double-Engineered Cysteine Antibodies

Based on the results of the above single-engineered cysteine mutant screen, double mutants were generated in the same manner as described in Example 1 except that the expression was performed at 5 or 10 ml scale in 50-ml Bioreactor tubes and HiTrap Protein A columns were used for antibody purification using Protein Maker (Protein BioSolutions). PEG conjugation and PEGylation screening was performed as recited above in Example 2.

The double cysteine mutants proposed are recited below in Table 2.

TABLE 2

Proposed double cysteine mutants

| Screen | Sample # | Mutant |
|---|---|---|
| B | 1 | K290C + N384C |
| B | 2 | K290C + G385C |
| B | 3 | K290C + V422C |
| B | 4 | K290C + S440C |
| B | 5 | K290C + S442C |
| B | 6 | A339C + N384C |
| B | 7 | A339C + G385C |
| B | 8 | A339C + V422C |
| B | 9 | A339C + S440C |
| B | 10 | A339C + S442C |
| B | 11 | A339C + K290C |
| B | 12 | S442C + V422C |
| B | 13 | S440C + N384C |
| B | 14 | A118C + N384C |
| B | 15 | A118C + G385C |
| B | 16 | A118C + V422C |
| B | 17 | A118C + S440C |
| B | 18 | A118C + S442C |
| B | 19 | A118C + K290C |
| B | 20 | A118C + K274C |
| B | 21 | A118C + A339C |
| B | 22 | A118C + K360C |
| B | 23 | A118C + Q418C |
| A | 24 | K274C + N384C |
| A | 25 | K274C + G385C |
| A | 26 | K274C + V422C |
| A | 27 | K274C + S440C |
| A | 28 | K274C + S442C |
| A | 29 | K274C + K360C |
| A | 30 | K274C + A339C |
| A | 31 | K274C + K414C |
| A | 32 | K360C + V422C |
| A | 33 | K360C + S440C |
| A | 34 | K360C + S442C |
| A | 35 | K360C + N384C |
| A | 36 | K360C + G385C |
| A | 37 | K360C + A339C |
| A | 38 | K360C + K290C |

Double cysteine mutants were prepared as follows. Mutagenesis was performed using Q5 or QuickChange Lightning SDM kits. Expression was performed using Expi293 expression in 10-ml bioreactor tubes. Purification was performed using protein A-based purification on 1-ml MabSelect Sure on Protein Maker. This was followed by buffer exchange with Amicon-15 (10 kD cutout). Representative purifications under non-reducing and reducing conditions are shown in FIG. 7, while purification data for all double cysteine mutants are shown in Table 3. Thermostability analysis using nanoDSF is shown in FIG. 8.

TABLE 3

Antibody purification

| Screen/ Sample # | Antibody Mutations | Conc., mg/ml | Volume, ml | Yield, mg | Titer in CM, μg/ml |
|---|---|---|---|---|---|
| | parental antibody | 4.07 | 0.72 | 2.9 | 293 |
| B/1 | K290C + N384C | 2.76 | 0.53 | 1.46 | 146 |
| B/2 | K290C + G385C | 2.6 | 0.86 | 2.2 | 224 |
| B/3 | K290C + V422C | 3.34 | 1.08 | 3.6 | 361 |
| B/4 | K290C + S440C | 2.86 | 0.85 | 2.4 | 243 |
| B/5 | K290C + S442C | 3.92 | 0.84 | 3.3 | 329 |
| B/6 | A339C + N384C | 3.98 | 0.67 | 2.7 | 267 |
| B/7 | A339C + G385C | 3.45 | 0.97 | 3.3 | 335 |
| B/8 | A339C + V422C | 3.77 | 0.91 | 3.4 | 343 |
| B/9 | A339C + S440C | 3.97 | 0.92 | 3.65 | 365 |
| B/10 | A339C + S442C | 3.77 | 0.97 | 3.7 | 366 |
| B/11 | A339C + K290C | 4.54 | 0.82 | 3.72 | 372 |
| B/12 | S442C + V422C | 3.63 | 0.95 | 3.4 | 345 |

TABLE 3-continued

| Antibody purification | | | | | |
|---|---|---|---|---|---|
| Screen/ Sample # | Antibody Mutations | Conc., mg/ml | Volume, ml | Yield, mg | Titer in CM, μg/ml |
| B/13 | S440C + N384C | 1.2 | 2.57 | 3.1 | 308 |
| B/14 | A118C + N384C | 2.26 | 0.61 | 1.4 | 138 |
| B/15 | A118C + G385C | 4.94 | 0.68 | 3.36 | 336 |
| B/16 | A118C + V422C | 5.62 | 0.6 | 3.37 | 337 |
| B/17 | A118C + S440C | 2.73 | 0.65 | 1.8 | 177 |
| B/18 | A118C + S442C | 4.02 | 0.86 | 3.46 | 346 |
| B/19 | A118C + K290C | 5.44 | 0.78 | 4.24 | 424 |
| B/20 | A118C + K274C | 3.22 | 0.59 | 1.9 | 190 |
| B/21 | A118C + A339C | 0.22 | 0.46 | 0.1 | 10 |
| B/22 | A118C + K360C | 2.66 | 0.71 | 1.9 | 189 |
| B/23 | A118C + Q418C | 4.88 | 0.81 | 3.95 | 395 |
| A/24 | K274C + N384C | 4.17 | 0.72 | 3.00 | 300.24 |
| A/25 | K274C + G385C | 3.64 | 0.68 | 2.48 | 247.52 |
| A/26 | K274C + V422C | 8.05 | 0.62 | 4.99 | 499.1 |
| A/27 | K274C + S440C | 4.57 | 0.79 | 3.61 | 361.03 |
| A/28 | K274C + S442C | 4.87 | 0.71 | 3.46 | 345.77 |
| A/29 | K274C + K360C | 4.54 | 0.84 | 3.81 | 381.36 |
| A/30 | K274C + A339C | 4.17 | 0.71 | 2.96 | 296.07 |
| A/31 | K274C + K414C | 5.72 | 0.58 | 3.32 | 331.76 |
| A/32 | K360C + V422C | 5.24 | 0.61 | 3.20 | 319.64 |
| A/33 | K360C + S440C | 6.34 | 0.75 | 4.76 | 475.5 |
| A/34 | K360C + S442C | 5.76 | 0.56 | 3.23 | 322.56 |
| A/35 | K360C + N384C | 5.07 | 0.66 | 3.35 | 334.62 |
| A/36 | K360C + G385C | 4.65 | 0.71 | 3.30 | 330.15 |
| A/37 | K360C + A339C | 5.86 | 0.64 | 3.75 | 375.04 |
| A/38 | K360C + K290C | 1.22 | 0.27 | 0.33 | 32.94 |
| A/39 | WT ctrl | 4.97 | 0.62 | 3.08 | 308.14 |

Example 4—PEGylation Screening of Double-Engineered Cysteine Antibodies

Antibodies with double-engineered cysteine mutants were investigated for conjugatability using THITOMAB approach with maleimide PEG (5 kDa), as in Example 2.

Double cysteine mutants were ranked by degree and selectivity of PEGylation, which served as a proxy for drug-based conjugation due to the size of the PEG molecule (FIG. 9 and FIG. 10). The selection criteria are recited below:

≥8000 mono- and di-PEGylated

≤1000 multi-PEGylated

PEG: Antibody Ratio (PAR) ≥3.4

≤5% un-PEGylated

Based on the above selection criteria, 19 double-engineered cysteine mutants were identified (FIG. 11, FIG. 12, FIG. 13, FIG. 14).

Example 5—Preparation of Conjugated Single-Engineered Parental Cysteine Antibodies with Alternative Reductant TCEP In addition to the previously described DTT reduction to uncap engineered single cysteine residues, TCEP reduction was also investigated. 27 different antibody cysteine mutants were investigated for conjugatability using THIOMAB approach with maleimide PEG (5 kDa) and TCEP. Both Coomassie and PEG staining of SDS-PAGE gels was used to detect PEGylation. However, Coomassie staining alone was used for conjugation ranking. Mutants were screened under non-reducing and reducing conditions (FIG. 15).

Mutants were ranked by different metrics, including conjugation efficiency (PAR) and selectivity (% mono-PEGylated, % un-PEGylated, and % multi-PEGylated heavy chain), as done with previous screening using DTT (FIG. 16 and FIG. 17).

Mutations K326C, T299C, A339C, K274C, G385C, Q386C, Y300C, K414C, S440C, S415C were identified as top 10 mutants with TCEP screening. Compared back to the original DTT screen, four mutants (A339C, K274C, S440C, G385C) are top 10 in conjugation using either TCEP or DTT uncapping.

The data shows that for the conjugation using TCEP, multi-PEGylation and PAR was reduced. The difference in conjugation efficiency between DTT and TCEP uncapping may be due to local hydrophobicity.

Example 6—Conjugation Efficiency Observed Among Single Cysteine Mutants

Figure 3:
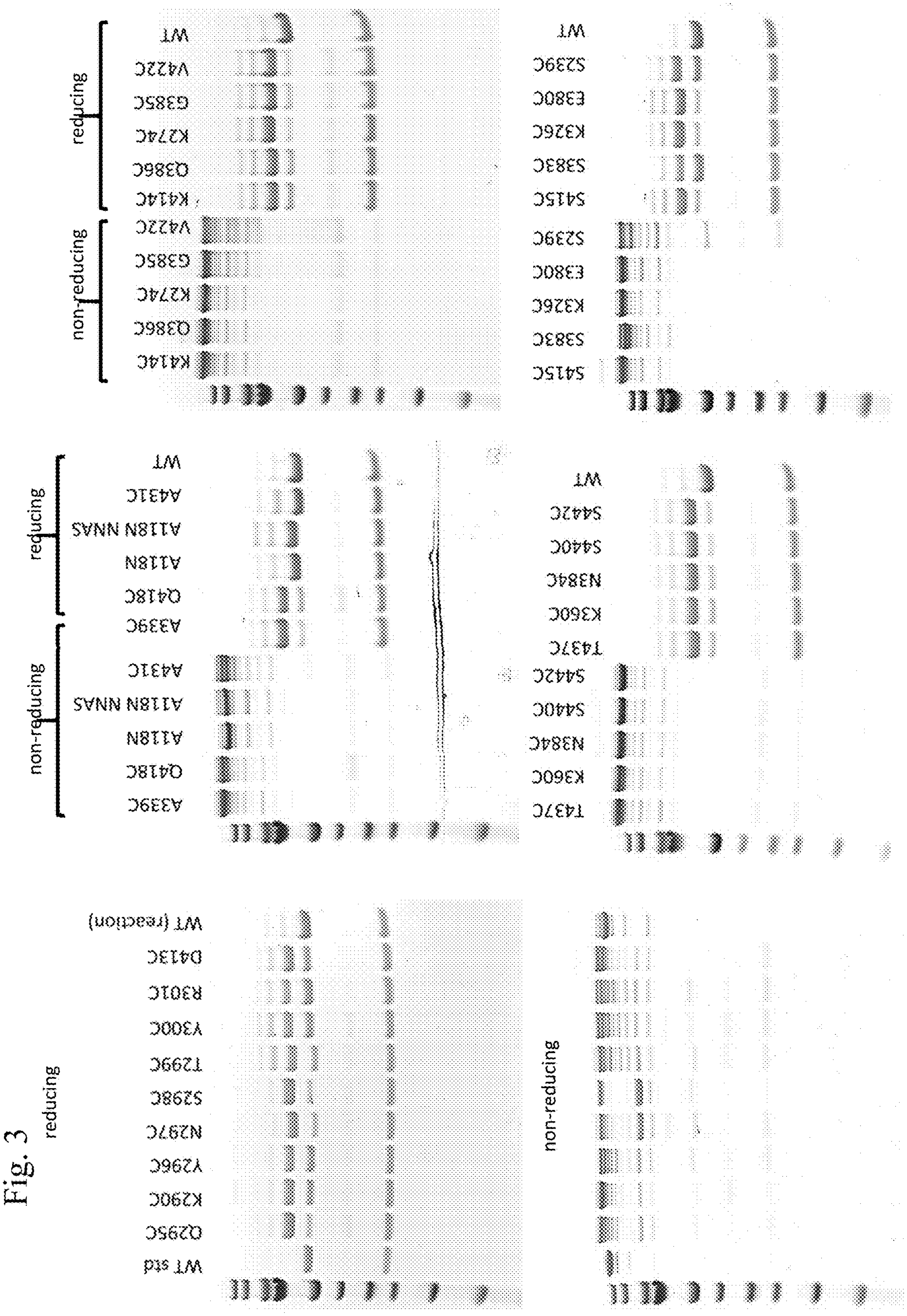
FIG. 3 depicts screening of single-engineered parental antibodies with DTT. Single-engineered parental antibodies (mutants) with a first position cysteine mutation were screened with DTT reductant by loading onto PEG-stained SDS-PAGE with 64 eq DTT for uncapping. Each engineered antibody depicted was screened using reducing and non-reducing conditions.

The conjugatability of these mutants was further investigated using PEGylation. After the antibody mutants were partially reduced with DTT, they were re-oxidized with dehydroascorbic acid (dHAA). The antibodies were then PEGylated and analyzed using SDS-PAGE under both non-reducing and reducing conditions with the gels stained using Coomassie blue (FIG. 3). The PEGylation of same samples was confirmed with reducing SDS-PAGE gels stained with PEG staining (FIG. 20). The mono-PEGylated, un-PEGylated, and multi-PEGylated protein bands were detected on the Coomassie blue stained reducing gels which were scanned using ProteinSimple. The percentage of each species was determined with AlphaView software.

Different single cysteine mutants were PEGylated at different efficiencies (PAR or PEG-to-antibody ratio) and different selectivities which were calculated by subtracting the mono-PEGylated band (desired species) by the un-PEGylated and multi-PEGylated bands (above two PEG conjugated per each of antibody heavy chain, un-desired species)(FIG. 3). Interestingly, there is low protein aggregates found in most of the conjugates as shown by non-reducing SDS-PAGE, although some of them displayed some level of aggregation before conjugation as shown previously (FIG. 1). Significant amounts of half-antibody conjugate species were detected with mutants N297C and N298C under non-reducing SDS-PAGE. This was confirmed by PEG staining (FIG. 23).

Ten top single cysteine mutants were selected from these twenty-seven mutants based on their high conjugation efficiency (PAR >1.7) and selectivity (>60% mono-PEGylated, <20% multi-PEGylated, and <20% un-PEGylated): A339C, S440C, K290C, S442C, K274C, V422C, N384C, G385C, Q418C, and K360C. Although some of other mutants show high PAR, they were excluded from the top list due to their low selectivity or the presence of significant amounts of half antibody conjugates.

Example 7—Effect of Conjugation on FcγRIIa Binding

Three cysteine mutants were PEGylated with 2 kDa maleimide PEG or conjugated with PEG2-biotin linker using DTT uncapping of unpaired cysteine. Specific mutations K290C, Q295C, and S442C were chosen (FIG. 18). Upon conjugation, the antibodies were analyzed for FcγRIIIa binding using a Biacore. Table 4 below shows the number of conjugates per an antibody at each position.

TABLE 4

| Number of PEG conjugates and biotin conjugates per an antibody at each single mutation position | | |
|---|---|---|
| Name | PAR (# 2 kDa PEG/mAb) | Biotin (# PEG2-biotin/mAb) |
| K290C | 2.47 | 1.6 |
| Q295C | 2.32 | 1.8 |
| S442C | 2.87 | 3.6 |

To test FcγRIIIa binding, an anti-HPC4-tag antibody was immobilized on a CM5 sensor chip. A HPC4-tagged FcγRIIIa was then captured by the immobilized anti-HPC4 antibodies (in the presence of $Ca^{2+}$). Triplicate injection of each conjugated single mutant antibody at a constant concentration was then performed. The kinetics were performed with an 180 second association and a 180 second dissociation phase. For analysis, the average of the steady state binding response for each variant was calculated.

As shown in FIG. 19, all three variants show a similar FcγRIIIa binding response as the WT antibody. PEGylation reduced the binding for all three variants and biotin conjugation did not significantly affect the binding of K290C or S442C.

Example 8—Plasma Stability of PEGylated Single Cysteine Mutants

Seven single cysteine mutants (A339C, S440C, S442C, K274C, V422C, N384C, and G385C) were incubated with mouse plasma (0.02 mg/mL, close to initial plasma concentration in mouse injected with 1 mg/kg in vivo). After the samples were incubated at 37° C. in a $CO_2$ incubator for 0 and 96 hours, the samples were analyzed using western blot. The western blot was performed with a recombinant rabbit anti-PEG antibody. The mono-PEGylated bands were analyzed. In the western blot, the top diffuse bands are multi-PEGylated species which react with the anti-PEG antibody strongly due to presence of more PEG. The western blot is show in FIG. 21. The mono-PEGylated bands from the western blot were analyzed and plotted, as shown in FIG. 22. The results show that the PEGylated mutants display stability with at least 75% of PEGylation remained in the protein after incubation in plasma for 96 hours as compared to the samples without incubation.

Example 9—Preparation of Additional Double-Engineered Cysteine Antibodies

Thirty-eight double cysteine mutants were designed based on previous results from PEGylation screening of single cysteine mutants. The top ten single cysteine mutations except for Q418C from PEGylation with DTT reduction as described above were combined with each other or with A118C reported previously (U.S. Pat. No. 7,521,541). They were generated using site-directed mutagenesis and expressed from Expi293 cells. Most of the engineered double cysteine mutants show comparable expression titers except for the double cysteine mutant K360C+K290C which shows at least 4-fold reduced titer (Table 5). The result from SDS-PAGE showed high aggregation for the mutant S440C+N384C (FIG. 7), while SEC-HPLC analysis also detected high aggregates for this double cysteine mutant as well as A339C+S440C. The thermal stability of these mutants was also compared with the wild-type antibody and most of the double cysteine mutants containing the A339C mutation, including A339C+N384C, A339C+G385C, A339C+V422C, A339C+S442C, A118C+A339C, and K274C+A339C, display a thermal transitional temperature (Tm1) at least 2 degrees lower than the wild-type antibody (Table 5).

TABLE 5

| DAR values for double cysteine antibody mutations | | | |
|---|---|---|---|
| mAb | mAb titer, µg/ml * | Stability (nanoDSF Tm1), ° C. ** | SEC, % monomer *** |
| K290C + N384C | 146 | NA | 92.1 |
| K290C + G385C | 224 | 74.1 | 89.4 |
| K290C + V422C | 361 | 72.9 | 92.9 |
| K290C + S440C | 243 | 74.2 | 89.3 |
| K290C + S442C | 329 | 73.3 | 94.4 |
| A339C + N384C | 267 | **66.0** | 89.5 |
| A339C + G385C | 335 | **65.0** | 84.9 |
| A339C + V422C | 343 | **65.9** | 93.6 |
| A339C + S440C | 365 | **NA** | **77.0** |
| A339C + S442C | 366 | **65.5** | 94.0 |
| A339C + K290C | 372 | NA | 96.7 |
| S442C + V422C | 345 | 69.5 | 97.6 |
| S440C + N384C | 308 | 70.2 | **45.7** |
| A118C + N384C | 138 | 67.7 | 93.3 |
| A118C + G385C | 336 | 68.2 | 94.9 |
| A118C + V422C | 337 | 67.9 | 97.4 |
| A118C + S440C | 177 | 69.8 | 89.2 |
| A118C + S442C | 346 | 68.3 | 95.7 |
| A118C + K290C | 424 | NA | NA |
| A118C + K274C | 190 | 69.3 | 95.7 |
| A118C + A339C | 414 | **58.8** | 99.4 |
| A118C + K360C | 189 | 68.3 | 96.0 |
| A118C + Q418C | 395 | 69.0 | 93.9 |
| K274C + N384C | 300 | 69.6 | 87.0 |
| K274C + G385C | 248 | 70.8 | 84.9 |
| K274C + V422C | 499 | 69.9 | 94.3 |
| K274C + S440C | 361 | 71.7 | 85.4 |
| K274C + S442C | 346 | 69.5 | 94.3 |
| K274C + K360C | 381 | 70.4 | 97.4 |
| K274C + A339C | 296 | **66.4** | 97.9 |
| K274C + K414C | 332 | 72.3 | 96.5 |
| K360C + V422C | 320 | 68.6 | 97.3 |
| K360C + S440C | 476 | 69.3 | 90.8 |
| K360C + S442C | 323 | 69.0 | 97.4 |
| K360C + N384C | 335 | 69.0 | 89.0 |
| K360C + G385C | 330 | 68.3 | 90.1 |
| K360C + A339C | 375 | 66.9 | 98.5 |
| K360C + K290C | **33** | 72.5 | 98.1 |
| Wild-type | 293 | 68.5 | 98.1 |

Notes:

* The double cysteine mutant with titer below 130 µg/ml is highlighted in bold underlined text;

** the mutant with Tm1 ≥ 2 degrees below the wild-type antibody is in bold underlined text;

*** the mutants with monomer species below 85% are in bold underlined text.

The above recited double cysteine mutants were screened for conjugation efficiency and selectivity using PEGylation. Different amounts of DTT, dHAA, and PEG were initially investigated for optimal conditions before the PEGylation procedure was applied for screening (data not shown). The mutants were partially reduced using DTT to uncap the engineered double cysteine residues. After re-oxidation, the antibody mutants were conjugated with PEG. The PEGylated mutants were analyzed using SDS-PAGE and stained with Coomassie blue (FIG. 9 and FIG. 24). Most of the mutants showed low aggregation after PEGylation when analyzed under non-reducing conditions. In addition, there was a double cysteine mutant, S442C+V422C, showing no conjugation comparable to wild-type antibody. The PEGylation of this mutant was repeated with similar result. As shown in FIG. 10, the double cysteine mutants show variable conjugation efficiency (PAR). The conjugation selectivity was calculated by subtracting mono- and di-PEGylated bands (desired species) with un-PEGylated and multi-PEGylated bands (over 3 PEG conjugated per each antibody heavy chain) (undesired species) and found variable among the mutants. Out of thirty-eight mutants, there are seventeen mutants which display PAR above 3.4 after conjugation. They also show good selectivity (>0.7) with mono- and di-PEGylated proteins above 85%, multi-PEGylated species below 10%, and un-PEGylated species below 6% (FIG. 11 and FIG. 25, heat map). This selection criteria differs from the selection criteria of Example 4. The top double cysteine mutants include A118C paired with A339C, G385C, K274C, N384C, S440C, or V422C; A339C paired with G385C, K290C, N384C, S440C, or V422C; K274C paired with A339C, G385C, N384C, S440C, or V422C; and K290C paired with N384C.

Example 10—Conjugation of Double Cysteine Mutants with PROTAC Linker

Three top double cysteine mutants were reduced with DTT (120 eq) and re-oxidized with dHAA (30 eq) as described for PEGylation. The partially reduced and re-oxidized antibody mutants were then first conjugated with BCN-PEG3-Maleimide linker at 20 eq and then a PROTAC linker, PROTAC BRD4 Degrader-5-CO-PEG3-N3, at 20 eq as described by Manerio et al. (ACS Chem Biol. 2020. 15(6): 1306-1312). The conjugates were analyzed using MALDI-TOF MS for intact protein analysis (linear positive mode). The DARs were calculated by dividing the differences in average masses between the conjugates and non-conjugated mutants by the mass of two linkers. The results are shown below in Table 6. The DAR values were lower than the PAR values for the same double cysteine mutations recited above. The PROTAC linker used in this study was of low quality, which contributed to the lower DAR values. Repeat analysis of these double cysteine mutations with PEGylation confirmed that the lower DAR values are not the result of a loss of activity at the engineered cysteine sites.

TABLE 6

DAR values for double cysteine antibody mutations

| Samples | DAR |
|---|---|
| A118C + A339C PROTAC conjugate | 2.9 ± 0.1 |
| A118C + V422C PROTAC conjugate | 2.4 ± 0.3 |
| K274C + S440C PROTAC conjugate | 2.6 ± 0.1 |

What is claimed is:

1. An antigen-binding protein or antigen-binding fragment thereof, comprising an antigen-binding domain and an antibody heavy chain constant (CH) domain, wherein the antigen-binding protein or antigen-binding fragment thereof is double engineered with a pair of cysteine reactive amino acid residues at positions selected from the group consisting of: A118C and K274C, A118C and A339C, A118C and N384C, A118C and G385C, A118C and V422C, and A118C and S440C, according to the numbering of the EU index of Kabat, wherein the cysteine reactive amino acid residues are conjugated to a ligand via a linker, and wherein the antigen-binding protein comprises a ligand to antibody ratio (LAR) of at least 3.0.

2. The antigen-binding protein or antigen-binding fragment thereof of claim 1, wherein the engineered reactive amino acid residue is conjugated to a ligand via a reactive moiety.

3. The antigen-binding protein or antigen-binding fragment thereof of claim 2, wherein the ligand is a detection probe.

4. The antigen-binding protein or antigen-binding fragment thereof of claim 1, further comprising an antibody heavy chain variable (VH) domain and an antibody light chain variable ($V_L$) domain.

5. A pharmaceutical composition comprising the antigen-binding protein or antigen-binding fragment thereof of claim 1, further comprising a pharmaceutically acceptable carrier.

6. The antigen-binding protein or antigen-binding fragment thereof of claim 2, wherein the antigen-binding protein or antigen-binding fragment thereof further comprises a linker conjugating the engineered reactive amino acid residue to the ligand.

7. The antigen-binding protein or antigen-binding fragment thereof of claim 6, wherein the linker is cleavable.

8. The antigen-binding protein or antigen-binding fragment thereof of claim 6, wherein the linker is non-cleavable.

9. The antigen-binding protein or antigen-binding fragment thereof of claim 2, comprising a ligand to antibody ratio (LAR) of at least 3.4.

10. The antigen-binding protein or antigen-binding fragment thereof of claim 3, wherein the detection probe is selected from the group consisting of: a biotin, polyethylene glycol (PEG), fluorescent tag, visualization peptide, and a combination thereof.

11. The antigen-binding protein or antigen-binding fragment thereof of claim 2, wherein the ligand is a targeting moiety.

12. The antigen-binding protein or antigen-binding fragment thereof of claim 11, wherein the targeting moiety is selected from the group consisting of: a protein, nucleic acid, lipid, carbohydrate, and a combination thereof.

13. The antigen-binding protein or antigen-binding fragment thereof of claim 2, wherein the ligand is a drug.

14. The antigen-binding protein or antigen-binding fragment thereof of claim 13, wherein the antigen-binding protein or antigen-binding fragment thereof comprises a drug to antibody ratio (DAR) of at least 3.0 or at least 3.4.

15. The antigen-binding protein or antigen-binding fragment thereof of claim 4, wherein the antigen-binding protein is a chimeric or humanized or human antibody; and/or the antigen-binding protein is a monoclonal antibody.

16. The antigen-binding protein or antigen-binding fragment thereof of claim 4, wherein the antigen-binding protein comprises one or more full-length antibody heavy chains comprising an Fc region.

17. The antigen-binding protein or antigen-binding fragment thereof of claim 16, wherein the Fc region is a human IgG1 Fc region.

18. The antigen-binding protein or antigen-binding fragment thereof of claim 13, wherein the drug is selected from the group consisting of: an anti-cancer therapeutic agent, anti-inflammatory therapeutic agent, anti-infective therapeutic agent, anesthetic therapeutic agent, cytotoxic therapeutic agent, radionuclide, immunomodulator, cell signaling peptide, growth factor, enzyme, oligonucleotide, photoactive therapeutic agent, and a combination thereof.

19. The antigen-binding protein or antigen-binding fragment thereof of claim 13, wherein the drug is an anti-cancer therapeutic agent selected from the group consisting of: a cytostatic, cytotoxic nucleoside, tubulin binding agent, hormone or hormone antagonist, anti-angiogenesis agent, enzyme inhibitor, gene regulator, proteasome inhibitor, pteridine, diynene, podophyllotoxin, auristatin, geldanamycin, calicheamicin, gramicidin D, maytansanoids, neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, maytansine, anthracycline, bisphosphonate, leptomycin, streptonigrin, duocarmycin, and a combination thereof.

20. The antigen-binding protein or antigen-binding fragment thereof of claim 13, wherein the drug the is a cytostatic selected from the group consisting of: an anthracine, DNA synthesis inhibitor, DNA-intercalator, DNA-RNA transcription regulator, ansamycin benzoquinone, quinonoid, busulfan, ifosfamide, mechlorethamine, triaziquone, diaziquone, carbazilquinone, indoloquinone E09, diaziridinyl-benzoquinone methyl DZQ, triethylenephosphoramide, nitrosourea compound, and a combination thereof.

21. The antigen-binding protein or antigen-binding fragment thereof of claim 13, wherein the drug is a cytotoxic nucleoside selected from the group consisting of: adenosine arabinoside, cytarabine, cytosine arabinoside, 5-fluorouracil, fludarabine, floxuridine, ftorafur, 6-mercaptopurine, and a combination thereof.

22. The antigen-binding protein or antigen-binding fragment thereof of claim 13, wherein the drug is a tubulin binding agent selected from the group consisting of: taxoid, nocodazole, rhizoxin, dolastatin, colchicine, colchicinoid, combretastatin, vinca alkaloid, and a combination thereof.

23. The antigen-binding protein or antigen-binding fragment thereof of claim 13, wherein the drug is a hormone or hormone antagonist selected from the group consisting of: corticosteroid, progestin, estrogen, antiestrogen, androgen, aromatase inhibitor, 17-(allylamino)-17-demethoxygeldanamycin, 4-amino-I, 8-naphthalimide, apigenin, brefeldin A, cimetidine, dichloromethylene-diphosphonic acid, leuprolide, luteinizing hormone-releasing hormone, pifithrin-a, rapamycin, sex hormone-binding globulin, thapsigargin, and a combination thereof.

24. The antigen-binding protein or antigen-binding fragment thereof of claim 13, wherein the drug is an anti-angiogenesis agent selected from the group consisting of: Angiostatin Kl-3, DL-a-difluoromethyl-ornithine, endostatin, fumagillin, genistein, minocycline, staurosporine, (+)-thalidomide, and a combination thereof.

25. The antigen-binding protein or antigen-binding fragment thereof of claim 13, wherein the drug is an enzyme inhibitor selected from the group consisting of: S (+)-camptothecin, curcumin, (−)-deguelin, 5,6-di Chlorobenzimidazole I-β-D-ribofuranoside, etoposide, formestane, fostriecin, hispidin, 2-imino-1-imidazolidineacetic acid, mevinolin, trichostatin A, tyrphostin AG 34, tyrphostin AG 879, and a combination thereof.

26. The antigen-binding protein or antigen-binding fragment thereof of claim 13, wherein the drug is a gene regulator selected from the group consisting of: 5-aza-2'-deoxycytidine, 5-azacytidine, cholecalciferol, 4-hydroxytamoxifen, melatonin, mifepristone, raloxifene, trans-retinal, retinoic acid, vitamin A acid, 9-cis-retinoic acid, 13-cis-retinoic acid, retinol, tamoxifen, troglitazone, and a combination thereof.

27. The antigen-binding protein or antigen-binding fragment thereof of claim 1, wherein the antigen-binding protein or antigen-binding fragment thereof is double engineered with a pair of cysteine reactive amino acid residues at positions A118C and K274C, according to the numbering of the EU index of Kabat.

28. The antigen-binding protein or antigen-binding fragment thereof of claim 1, wherein the antigen-binding protein or antigen-binding fragment thereof is double engineered with a pair of cysteine reactive amino acid residues at positions A118C and A339C, according to the numbering of the EU index of Kabat.

29. The antigen-binding protein or antigen-binding fragment thereof of claim 1, wherein the antigen-binding protein or antigen-binding fragment thereof is double engineered with a pair of cysteine reactive amino acid residues at positions A118C and N384C, according to the numbering of the EU index of Kabat.

30. The antigen-binding protein or antigen-binding fragment thereof of claim 1, wherein the antigen-binding protein or antigen-binding fragment thereof is double engineered with a pair of cysteine reactive amino acid residues at positions A118C and G385C, according to the numbering of the EU index of Kabat.

31. The antigen-binding protein or antigen-binding fragment thereof of claim 1, wherein the antigen-binding protein or antigen-binding fragment thereof is double engineered with a pair of cysteine reactive amino acid residues at positions A118C and V422C, according to the numbering of the EU index of Kabat.

32. The antigen-binding protein or antigen-binding fragment thereof of claim 1, wherein the antigen-binding protein or antigen-binding fragment thereof is double engineered with a pair of cysteine reactive amino acid residues at positions A118C and S440C, according to the numbering of the EU index of Kabat.

33. The antigen-binding protein or antigen-binding fragment thereof of claim 1, wherein the antigen-binding protein or antigen-binding fragment thereof comprises a single domain antibody.

34. The antigen-binding protein or antigen-binding fragment thereof of claim 13, wherein: the drug is a prodrug selected from the group consisting of: a phosphate-containing prodrug, amino acid-containing prodrug, thiophosphate-containing prodrug, sulfate-containing prodrug, peptide-containing prodrug, β-lactam-containing prodrug, phenoxyacetamide-containing prodrug, phenylacetamide-containing prodrug, 5-fluorocytosine prodrug, 5-fluorouridine prodrug, and a combination thereof.

* * * * *